US009056908B2

(12) United States Patent
Culp

(10) Patent No.: US 9,056,908 B2
(45) Date of Patent: Jun. 16, 2015

(54) THERAPEUTIC USE OF ANTI-TWEAK RECEPTOR ANTIBODIES

(75) Inventor: Patricia Culp, Oakland, CA (US)

(73) Assignee: AbbVie Biotherapeutics Inc., Redwood City, CA (US)

(*) Notice: Subject to any disclaimer, the term of this patent is extended or adjusted under 35 U.S.C. 154(b) by 768 days.

(21) Appl. No.: 12/185,689

(22) Filed: Aug. 4, 2008

(65) Prior Publication Data
US 2009/0074762 A1 Mar. 19, 2009

Related U.S. Application Data

(60) Provisional application No. 60/953,745, filed on Aug. 3, 2007, provisional application No. 61/123,623, filed on Apr. 9, 2008.

(51) Int. Cl.
C07K 16/00 (2006.01)
C12P 21/08 (2006.01)
A61K 39/395 (2006.01)
A61K 39/00 (2006.01)
C07K 16/28 (2006.01)
C07K 16/30 (2006.01)

(52) U.S. Cl.
CPC ............ C07K 16/2878 (2013.01); A61K 39/00 (2013.01); C07K 16/00 (2013.01); C07K 2319/55 (2013.01); C07K 16/30 (2013.01); A61K 2039/505 (2013.01); C07K 2316/96 (2013.01); C07K 2317/24 (2013.01); C07K 2317/73 (2013.01); C07K 2317/732 (2013.01); C07K 2317/75 (2013.01); C07K 2317/76 (2013.01); C07K 2317/92 (2013.01); C07K 2317/52 (2013.01)

(58) Field of Classification Search
None
See application file for complete search history.

(56) References Cited

U.S. PATENT DOCUMENTS

| 6,531,447 | B1 | 3/2003 | Ruben et al. |
| 6,727,225 | B2 | 4/2004 | Wiley |
| 6,812,339 | B1 | 11/2004 | Venter et al. |
| 6,824,773 | B2 | 11/2004 | Wiley |
| 7,001,992 | B2 | 2/2006 | Ruben et al. |
| 7,169,387 | B2 | 1/2007 | Rennert |
| 7,208,151 | B2 | 4/2007 | Browning et al. |
| 7,227,007 | B2 | 6/2007 | Matsuda et al. |
| 7,482,430 | B2 | 1/2009 | Wiley |
| 7,482,442 | B2 | 1/2009 | Ruben et al. |
| 7,495,086 | B2 | 2/2009 | Kim et al. |
| 7,507,580 | B2 | 3/2009 | Fox et al. |
| 7,507,807 | B2 | 3/2009 | Wiley |
| 7,517,962 | B2 | 4/2009 | Wiley |
| 2003/0228305 | A1 | 12/2003 | Frantz et al. |
| 2004/0214167 | A9 | 10/2004 | Matsuda et al. |
| 2005/0074842 | A1 | 4/2005 | Kato et al. |
| 2005/0112129 | A1 | 5/2005 | Phillips |
| 2007/0054312 | A1 | 3/2007 | Tang et al. |
| 2007/0083374 | A1 | 4/2007 | Mintz et al. |
| 2007/0105198 | A1 | 5/2007 | Matsuda et al. |
| 2007/0207462 | A1 | 9/2007 | Ichinose et al. |
| 2007/0224201 | A1 | 9/2007 | Wu et al. |
| 2007/0231323 | A1 | 10/2007 | Phillips |
| 2007/0298037 | A1 | 12/2007 | Fox et al. |
| 2008/0004432 | A1 | 1/2008 | Ruben et al. |
| 2008/0008714 | A1 | 1/2008 | Browning et al. |
| 2008/0187544 | A1 | 8/2008 | Burkly et al. |
| 2008/0279853 | A1 | 11/2008 | Burkly et al. |
| 2008/0286271 | A1 | 11/2008 | Ashkenazi et al. |
| 2008/0292622 | A1 | 11/2008 | Burkly et al. |
| 2009/0137035 | A1 | 5/2009 | Wiley |
| 2009/0137036 | A1 | 5/2009 | Kim et al. |
| 2009/0148900 | A1 | 6/2009 | Ruben et al. |
| 2009/0186409 | A1 | 7/2009 | Frantz et al. |

FOREIGN PATENT DOCUMENTS

| EP | 1354950 A1 | 10/2003 |
| EP | 2080812 A1 | 7/2009 |
| WO | 98/54206 A1 | 12/1998 |
| WO | 98/55508 A2 | 12/1998 |
| WO | 99/61471 A2 | 12/1999 |
| WO | 00/42073 A1 | 7/2000 |
| WO | 01/45730 A2 | 6/2001 |
| WO | 01/70979 A2 | 9/2001 |
| WO | 02/22166 A2 | 3/2002 |
| WO | 02/053737 A1 | 7/2002 |
| WO | 03/057160 A2 | 7/2003 |
| WO | 03/077939 A1 | 9/2003 |
| WO | 2004/030615 A2 | 4/2004 |
| WO | 2004/112829 A2 | 12/2004 |
| WO | 2005/010045 A1 | 2/2005 |
| WO | 2005/037865 A2 | 4/2005 |
| WO | 2005/080972 A1 | 9/2005 |
| WO | 2005/092383 A1 | 10/2005 |
| WO | 2006/047172 A1 | 5/2006 |
| WO | 2006/096487 A2 | 9/2006 |
| WO | 2006/122187 A2 | 11/2006 |
| WO | 2006/125632 A2 | 11/2006 |
| WO | 2006/130429 A2 | 12/2006 |

(Continued)

OTHER PUBLICATIONS

Paul, Fundamental Immunology, 3rd Edition, 1993, pp. 292-295.*
Rudikoff, Proc. Natl. Acad. Sci. USA, 79(6):1979-1983, Mar. 1982.*
Colman et al., Research in Immunology, 145:33-36, 1994.*
Bendig, Methods: A Companion to Methods in Enzymology, 8:83-93, 1995.*
MacCallum et al., J. Mol. Biol., 262, 732-745, 1996.*
Casset et al., Biochemical and Biophysical Research Communications, 307:198-205, 2003.*
Cancer information from National Institute of Cancer, Apr. 29, 2010, pp. 1-2.*

(Continued)

Primary Examiner — Hong Sang

(57) ABSTRACT

Provided herein are compositions comprising monoclonal antibodies and antigen binding fragments thereof that bind TweakR and methods for their use in treating cancer.

21 Claims, 27 Drawing Sheets

(56) References Cited

FOREIGN PATENT DOCUMENTS

| WO | 2006/138219 | A2 | 12/2006 |
|---|---|---|---|
| WO | 2007/039184 | A2 | 4/2007 |
| WO | 2008/140565 | A2 | 11/2008 |
| WO | 2009/083950 | A2 | 7/2009 |
| WO | 2009/090553 | A2 | 7/2009 |

OTHER PUBLICATIONS

Vogelstein et al., Nature Medicine, 2004, 10(8): 789-799.*

Akahori, Takahiro et al. "Significance of TWEAK/Fn14 pathway in human pancreatic cancer." Proceedings of the American Association for Cancer Research. Apr. 2006; 47:1346. Abstract #5724.

Chicheportiche, Yves et al. "TWEAK, a new secreted ligand in the tumor necrosis factor family that weakly induces apoptosis." J Biol Chem. Dec. 19, 1997;272(51):32401-10.

Culp, Patricia A. et al. "Anti-TweakR antibodies inhibit tumor growth in vivo through dual mechanisms." Proceedings of the American Association for Cancer Research. Apr. 2008; 49:354. Abstract #1511.

Desplat-Jego, Sophie et al. "TWEAK is expressed by glial cells, induces astrocyte proliferation and increases EAE severity." J Neuroimmunol. Dec. 2002;133(1-2):116-23.

Feng, Sheau-Line Y. et al. "The Fn14 immediate-early response gene is induced during liver regeneration and highly expressed in both human and murine hepatocellular carcinomas." Am J Pathol. Apr. 2000;156(4):1253-61.

Han, Haiyong et al. "Identification of differentially expressed genes in pancreatic cancer cells using cDNA microarray." Cancer Res. May 15, 2002;62(10):2890-6.

Jakubowski, Aniela et al. "Dual role for TWEAK in angiogenic regulation." J Cell Sci. Jan. 15, 2002;115(Pt 2):267-74.

Lynch, Carolyn N. et al. "TWEAK induces angiogenesis and proliferation of endothelial cells." J Biol Chem. Mar. 26, 1999;274(13):8455-9.

Meighan-Mantha, Rachel L. et al. "The mitogen-inducible Fn14 gene encodes a type I transmembrane protein that modulates fibroblast adhesion and migration." J Biol Chem. Nov. 12, 1999;274(46):33166-76.

Michaelson, Jennifer S. et al. "Tweak induces mammary epithelial branching morphogenesis." Oncogene. Apr. 14, 2005;24(16):2613-24.

Nakayama, Masafumi et al. "Characterization of murine TWEAK and its receptor (Fn14) by monoclonal antibodies." Biochem Biophys Res Commun. Jul. 11, 2003;306(4):819-25.

Nakayama, Masafumi et al. "Fibroblast growth factor-inducible 14 mediates multiple pathways of TWEAK-induced cell death." J Immunol. Jan. 1, 2003;170(1):341-8.

Tran, Nhan L. et al. "The human Fn14 receptor gene is up-regulated in migrating glioma cells in vitro and overexpressed in advanced glial tumors." Am J Pathol. Apr. 2003;162(4):1313-21.

Wang, S. et al. "Transcriptional profiling suggests that Barrett's metaplasia is an early intermediate stage in esophageal adenocarcinogenesis." Oncogene. Jun. 1, 2006;25(23):3346-56.

Wiley, Steven R. et al. "A novel TNF receptor family member binds TWEAK and is implicated in angiogenesis." Immunity. Nov. 2001;15(5):837-46.

Winkles, Jeffrey A. et al. "TWEAK and Fn14: new molecular targets for cancer therapy?" Cancer Lett. Apr. 8, 2006;235(1):11-7.

Winkles, Jeffrey A. et al. "Role of TWEAK and Fn14 in tumor biology." Front Biosci. Jan. 1, 2007;12:2761-71.

International Search Report and Written Opinion for PCT/US2008/072146, dated Feb. 3, 2009.

Search Report issued by State Intellectual Property Office of the People's Republic of China (SIPO) dated Sep. 23, 2012, cited in counterpart Chinese application No. 200880101522.3.

Kaufman, Eric Neil et al. "Effect of bivalent interaction upon apparent antibody affinity: experimental confirmation of theory using fluorescence photobleaching and implications for antibody binding assays." Cancer Res. Aug. 1, 1992;52(15):4157-67.

* cited by examiner (SEQ ID NO: 1)

```
tcgacccacg cgtccgccca cgcgtccgcc cacgcgtccg ggcgcaggac gtgcactatg
gctcggggct cgctgcgccg gttgctgcgg ctcctcgtgc tggggctctg gctggcgttg
ctgcgctccg tggccgggga gcaagcgcca ggcaccgccc ctgctcccg cggcagctcc
tggagcgcgg acctggacaa gtgcatggac tgcgcgtctt gcaggcgcg accgcacagc
gacttctgcc tgggctgcgc tgcagcacct cctgccccct tccggctgct ttggcccatc
cttggggcg ctctgagcct gaccttcgtg ctggggctgc tttctggctt tttggtctgg
agacgatgcc gcaggagaga gaagttcacc accccatag aggagaccgg cggagagggc
tgcccagctg tggcgctgat ccagtgacaa tgtgcccct gccagccggg gctcgcccac
tcatcattca ttcatccatt ctagagccag tctctgcctc ccagacgcgg cgggagccaa
gctcctccac cacaagggg gtgggggcg gtgaatcacc tctgaggcct gggcccaggg
ttcagggaa ccttccaagg tgtctggttg ccctgcctct ggctccagaa cagaaaggga
gcctcacgct ggctcacaca aaacagctga cactgactaa ggaactgcag catttgcaca
ggggaggggg gtgcctcct tcctagaggc ctgggggcc aggctgactt gggggcaga
cttgacacta ggcccactc actcagatgt cctgaaattc caccacgggg gtcacctgg
ggggttaggg acctattttt aacactaggg ggctggccca ctaggagggc tggccctaag
atacagaccc ccccaactcc ccaaagcggg gaggagatat ttattttggg gagagtttgg
agggagggga gaatttatta ataaaagaat ctttaacttt aaaaaaaaaa aaaaaaaagg
gcggccgctc tagaggatcc ctc
```

FIG. 1A (SEQ ID NO: 2)

```
Met Ala Arg Gly Ser Leu Arg Arg Leu Leu Arg Leu Leu Val Leu Gly
Leu Trp Leu Ala Leu Leu Arg Ser Val Ala Gly Glu Gln Ala Pro Gly
Thr Ala Pro Cys Ser Arg Gly Ser Ser Trp Ser Ala Asp Leu Asp Lys
Cys Met Asp Cys Ala Ser Cys Arg Ala Arg Pro His Ser Asp Phe Cys
Leu Gly Cys Ala Ala Ala Pro Pro Ala Pro Phe Arg Leu Leu Trp Pro
Ile Leu Gly Gly Ala Leu Ser Leu Thr Phe Val Leu Gly Leu Leu Ser
Gly Phe Leu Val Trp Arg Arg Cys Arg Arg Arg Glu Lys Phe Thr Thr
Pro Ile Glu Glu Thr Gly Gly Glu Gly Cys Pro Ala Val Ala Leu Ile
Gln
```

FIG. 1B

VH (SEQ ID NO: 3)

(FR1)　　　　　　　　　　　　　　　(CDR1)　　　　　(FR2)　　　　　　　　(CDR2)
EVQLVESGGGLVQPGGSLRLSCAASGFTFS SYWMS WVRQAPGKGLEWVA EIRLKSDNYATHYAESVKG
(FR3)　　　　　　　　　　　　　　　　　　(CDR3)　　　　　(FR4)
RFTISRDDSKNSLYLQMNSLRAEDTAVYYCTG YYADAMDY WGQGTLVTVSS

VL (SEQ ID NO: 4)

(FR1)　　　　　　　　　　　　(CDR1)　　　　　　　　　　(FR2)　　　　　　　　(CDR2)
DIQMTQSPSSLSASVGDRVTITC RASQSVSTSSYSYMH WYQQKPGKAPKLLIK YASNLES
(FR3)　　　　　　　　　　　　　　　　　(CDR3)　　　　　(FR4)
GVPSRFSGSGSGTDFTLTISSLQPEDFATYYC QHSWEIPYT FGGGTKVEIK

*FIG. 2A*

VH (SEQ ID NO: 5)

(FR1)　　　　　　　　　　　　　　　(CDR1)　　　　　(FR2)　　　　　　　　(CDR2)
EVKLEESGGGLVQPGGSMKLSCVASGFTFS SYWMS WVRQSPEKGLEWVA EIRLKSDNYATHYAESVKG
(FR3)　　　　　　　　　　　　　　　　　　(CDR3)　　　　　(FR4)
KFTISRDDSKSRLYLQMNSLRAEDTGIYYCTG YYADAMDY WGQGTSVTVSS

VL (SEQ ID NO: 6)

(FR1)　　　　　　　　　　　　(CDR1)　　　　　　　　　　(FR2)　　　　　　　　(CDR2)
DIVLTQSPASLAVSLGQRATISC RASQSVSTSSYSYMH WYQQKPGQPPKLLIK YASNLES
(FR3)　　　　　　　　　　　　　　　　　(CDR3)　　　　　(FR4)
GVPARFSGSGSGTDFTLNIHPVEEEDTATYYC QHSWEIPYT FGGGTKLEIK

*FIG. 2B*

VH (SEQ ID NO:7)

```
         (FR1)                              (CDR1)          (FR2)                    (CDR2)
EVKLGESGGGLVQPGGSMKLSCVASGFPFT KYWMN WVRQSPEKGLEWVA EIRLKSDNYATHYAESAKG
         (FR3)                              (CDR3)          (FR4)
RFTISRDDSRSSVYLQMNNLRAEDTAIYYCSP TYADTMDY WGQGTSVTVSS
```

VL (SEQ ID NO:8)

```
         (FR1)                              (CDR1)                    (FR2)                  (CDR2)
DIVLTQSPASLAVSLGQRATISC KASQSVSTSTSYMQ WYQQRPGQSPKLLIK YASKLDS
         (FR3)                              (CDR3)          (FR4)
GVPARFSGSGSGTDFTLNIHPVEEEDTATYYC QHSWEIPYT FGGGTRLEIKR
```

FIG. 2C

VH (SEQ ID NO:9)

```
         (FR1)                              (CDR1)          (FR2)                    (CDR2)
EVKLEESGGGLVQPGGSMKLSCVASGFTFN NYWMS WVRQSPEKGLEWLA EIRLKSDNYATHYAESVKG
         (FR3)                              (CDR3)          (FR4)
KFTISRDDSKSRLYLQMNNLRAENTGIYYCTG GFADYFDY WGQGTTLTVSS
```

VL (SEQ ID NO:10)

```
         (FR1)                              (CDR1)                    (FR2)                  (CDR2)
DIVLTQSPASLTVSLGQRATISC RASQSVSTSSSYSYMQ WYQQRPGQPPKLLIK YATNLDS
         (FR3)                              (CDR3)          (FR4)
GVPARFSGSGSGTDFTLNIHPVEEEDAATYYC QHSWEIPYT FGGGTKLEIKR
```

FIG. 2D

VH (SEQ ID NO:11)

QVQLVQSGAEVKKPGASVKISCKVSGYTFT DFIIA WVKQAPGKGLEWIG EIYPGTGRTYYSEKFRG
          (FR1)              (CDR1)      (FR2)           (CDR2)

KATLTADKSTSTAYMELSSLRSEDTAVYYCAR RTIYYDYDGDY WGQGTTVTVSS
             (FR3)              (CDR3)     (FR4)

VL (SEQ ID NO:12)

DIVMTQSPLSLPVTPGEPASISC RSSKSLLHSNGITYLY WYLQKPGQSPQLLIY QMSNLAS
        (FR1)            (CDR1)        (FR2)         (CDR2)

GVPDRFSSSGSGTDFTLKISRVEAEDVGVYYC AHNLELPWT FGGGTKVEIK
            (FR3)              (CDR3)     (FR4)

FIG. 2E

Heavy Chain: CDR1

| | | |
|---|---|---|
| PDL192 | SYWMS | SEQ ID NO: 13 |
| 19.2.1 | SYWMS | SEQ ID NO: 14 |
| 136.1 | NYWMS | SEQ ID NO: 15 |
| 18.3.3 | KYWMN | SEQ ID NO: 16 |
| ITEM-3 | RYWMS | SEQ ID NO: 17 |
| ITEM-1 | NYWMN | SEQ ID NO: 18 |

*FIG. 3A*

Heavy Chain: CDR2

| | | |
|---|---|---|
| PDL192 | EIRLKSDNYAT-HYAESVKG | SEQ ID NO: 19 |
| 19.2.1 | EIRLKSDNYAT-HYAESVKG | SEQ ID NO: 20 |
| 136.1 | EIRLKSDNYAT-HYAESVKG | SEQ ID NO: 21 |
| 18.3.3 | EIRLKSDNYAT-HYAESAKG | SEQ ID NO: 22 |
| ITEM-3 | EIRVKSDNYATTHYAESVKG | SEQ ID NO: 23 |
| ITEM-1 | EIRLKSNNYAT-HYAESVKG | SEQ ID NO: 24 |

*FIG. 3B*

Heavy Chain: CDR3

| | | |
|---|---|---|
| PDL192 | YYADAMDY | SEQ ID NO: 25 |
| 19.2.1 | YYADAMDY | SEQ ID NO: 26 |
| 136.1 | GFADYFDY | SEQ ID NO: 27 |
| 18.3.3 | TYADTMDY | SEQ ID NO: 28 |
| ITEM-3 | YYADAMDY | SEQ ID NO: 29 |
| ITEM-1 | AYADYFDY | SEQ ID NO: 30 |

*FIG. 3C*

Heavy Chain: FR1

| | | |
|---|---|---|
| PDL192 | EVQLVESGGGLVQPGGSLRLSCAASGFTFS | SEQ ID NO: 31 |
| PDL192-2 | EVKLEESGGGLVQPGGSMKLSCVASGFTFS | SEQ ID NO: 32 |
| 19.2.1 | EVKLEESGGGLVQPGGSMKLSCVASGFTFS | SEQ ID NO: 33 |
| 136.1 | EVKLEESGGGLVQPGGSMKLSCVASGFTFN | SEQ ID NO: 34 |
| 18.3.3 | EVKLGESGGGLVQPGGSMKLSCVASGFPFT | SEQ ID NO: 35 |
| PDL183 | EVQLVESGGGLVQPGGSLRLSCAASGFPFT | SEQ ID NO: 36 |
| PDL183-2 | EVKLGESGGGLVQPGGSMKLSCVASGFTFS | SEQ ID NO: 37 |
| ITEM-3 | EVKLEESGGGLVQPGGSMKLSCVVSGLTFS | SEQ ID NO: 38 |
| ITEM-1 | EVKLEESGGGLVQPGGSMKLSCVASGFSFS | SEQ ID NO: 39 |

*FIG. 3D*

Heavy Chain: FR2

```
PDL192      WVRQAPGKGLEWVA            SEQ ID NO: 40
PDL192-2    WVRQSPEKGLEWVA            SEQ ID NO: 41
19.2.1      WVRQSPEKGLEWVA            SEQ ID NO: 42
136.1       WVRQSPEKGLEWLA            SEQ ID NO: 43
18.3.3      WVRQSPEKGLEWVA            SEQ ID NO: 44
PDL183      WVRQAPGKGLEWVA            SEQ ID NO: 45
PDL183-2    WVRQSPEKGLEWVS            SEQ ID NO: 46
ITEM-3      WVRQSPEKGLEWVA            SEQ ID NO: 47
ITEM-1      WVRQSPEKGLEWVA            SEQ ID NO: 48
```

*FIG. 3E*

Heavy Chain: FR3

```
PDL192      RFTISRDDSKNSLYLQMNSLRAEDTAVYYCTG     SEQ ID NO: 49
PDL192-2    KFTISRDNAKSRLYLQMNSLRAEDTGIYYCAR     SEQ ID NO: 50
19.2.1      KFTISRDDSKSRLYLQMNSLRAEDTGIYYCTG     SEQ ID NO: 51
136.1       KFTISRDDSKSRLYLQMNNLRAENTGIYYCTG     SEQ ID NO: 52
18.3.3      RFTISRDDSRSSVYLQMNNLRAEDTAIYYCSP     SEQ ID NO: 53
PDL183      RFTISRDDSKNTVYLQMNSLRAEDTAVYYCSP     SEQ ID NO: 54
PDL183-2    RFTISRDNARSSLYLQMNNLRAEDTAIYYCAR     SEQ ID NO: 55
ITEM-3      KFTVSRDDSKSRLYLQMSSLRPEDTGIYYCIG     SEQ ID NO: 56
ITEM-1      RFTISRHDSKSSVYLQMNNLRAEDTGIYYCTR     SEQ ID NO: 57
```

*FIG. 3F*

Heavy Chain: FR4

```
PDL192      WGQGTLVTVSS               SEQ ID NO: 58
19.2.1      WGQGTSVTVSS               SEQ ID NO: 59
136.1       WGQGTTLTVSS               SEQ ID NO: 60
18.3.3      WGQGTSVTVSS               SEQ ID NO: 61
PDL183      WGQGTLVTVSS               SEQ ID NO: 62
PDL183-2    WGQGTSVTVSS               SEQ ID NO: 63
ITEM-3      WGQGTSVTVSS               SEQ ID NO: 64
ITEM-1      WGQGTTLTVSS               SEQ ID NO: 65
```

*FIG. 3G*

Light Chain: CDR1

| | | |
|---|---|---|
| PDL192 | RASQSVSTSSYSYMH | SEQ ID NO: 66 |
| 19.2.1 | RASQSVSTSSYSYMH | SEQ ID NO: 67 |
| 136.1 | RASQSVSTSSYSYMQ | SEQ ID NO: 68 |
| 18.3.3 | KASQSVSTSTYSYMQ | SEQ ID NO: 69 |
| ITEM-3 | RASQSVSTSSYSYMH | SEQ ID NO: 70 |
| ITEM-1 | RASQSVSTSTYSYMH | SEQ ID NO: 71 |

*FIG. 4A*

Light Chain: CDR2

| | | |
|---|---|---|
| PDL192 | YASNLES | SEQ ID NO: 72 |
| 19.2.1 | YASNLES | SEQ ID NO: 73 |
| 136.1 | YATNLDS | SEQ ID NO: 74 |
| 18.3.3 | YASKLDS | SEQ ID NO: 75 |
| ITEM-3 | YASKLDS | SEQ ID NO: 76 |
| ITEM-1 | YASNLES | SEQ ID NO: 77 |

*FIG. 4B*

Light Chain: CDR3

| | | |
|---|---|---|
| PDL192 | QHSWEIPYT | SEQ ID NO: 78 |
| 19.2.1 | QHSWEIPYT | SEQ ID NO: 79 |
| 136.1 | QHSWEIPYT | SEQ ID NO: 80 |
| 18.3.3 | QHSWELPYT | SEQ ID NO: 81 |
| ITEM-3 | QHSWEIPWT | SEQ ID NO: 82 |
| ITEM-1 | QHSWEIPYT | SEQ ID NO: 83 |

*FIG. 4C*

Light Chain: FR1

| | | |
|---|---|---|
| PDL192 | DIQMTQSPSSLSASVGDRVTITC | SEQ ID NO: 84 |
| PDL192-2 | DIVLTQSPASLAVSLGQRATISC | SEQ ID NO: 85 |
| 19.2.1 | DIVLTQSPASLAVSLGQRATISC | SEQ ID NO: 86 |
| 136.1 | DIVLTQSPASLTVSLGQRATISC | SEQ ID NO: 87 |
| 18.3.3 | DIVLTQSPASLAVSLGQRATISC | SEQ ID NO: 88 |
| PDL183 | DIVLTQSPGTLSLSPGERATLSC | SEQ ID NO: 89 |
| PDL183-2 | EIVMTQSPASLAVSLGQRATISC | SEQ ID NO: 90 |
| ITEM-3 | DIVLTQSPASLVVSLGQRATISC | SEQ ID NO: 91 |
| ITEM-1 | DIVLTQSPASLVVSLGQRATISC | SEQ ID NO: 92 |

*FIG. 4D*

Light Chain: FR2

| | | |
|---|---|---|
| PDL192 | WYQQKPGKAPKLLIK | SEQ ID NO: 93 |
| PDL192-2 | WYQQKPGQPPKLLIY | SEQ ID NO: 94 |
| 19.2.1 | WYQQKPGQPPKLLIK | SEQ ID NO: 95 |
| 136.1 | WYQQRPGQPPKLLIK | SEQ ID NO: 96 |
| 18.3.3 | WYQQRPGQSPKLLIK | SEQ ID NO: 97 |
| PDL183 | WVQQKPGQAPRLLIK | SEQ ID NO: 98 |
| PDL183-2 | WYQQRPGQSPKLLIY | SEQ ID NO: 99 |
| ITEM-3 | WYQQKPGQPPKLLIK | SEQ ID NO: 100 |
| ITEM-1 | WYQQKPGQPPKILIK | SEQ ID NO: 101 |

*FIG. 4E*

Light Chain: FR3

| | | |
|---|---|---|
| PDL192 | GVPSRFSGSGSGTDFTLTISSLQPEDFATYYC | SEQ ID NO: 102 |
| PDL192-2 | GVPARFSGSGSGTDFTLNIHPVEEEDTATYYC | SEQ ID NO: 103 |
| 19.2.1 | GVPARFSGSGSGTDFTLNIHPVEEEDTATYYC | SEQ ID NO: 104 |
| 136.1 | GVPARFSGSGSGTDFTLNIHPVEEEDAATYYC | SEQ ID NO: 105 |
| 18.3.3 | GVPARFSGSGSGTDFTLNIHPVEEEDTATYYC | SEQ ID NO: 106 |
| PDL183 | GVPARFSGSGSGTDFTLTISRLEPEDFAVYYC | SEQ ID NO: 107 |
| PDL183-2 | GIPDRFSGSGSGTDFTLNIHPVQEEDTATYYC | SEQ ID NO: 108 |
| ITEM-3 | GVPARFSGSGSGTDFTLNIHPVEEEDTATYYC | SEQ ID NO: 109 |
| ITEM-1 | GVPARFSGSGSGTDFTLNIHPVEEEDTATYYC | SEQ ID NO: 110 |

*FIG. 4F*

Light Chain: FR4

| | | |
|---|---|---|
| PDL192 | FGGGTKVEIKR | SEQ ID NO: 111 |
| PDL192-2 | FGGGTKLEIKR | SEQ ID NO: 112 |
| 19.2.1 | FGGGTKLEIKR | SEQ ID NO: 113 |
| 136.1 | FGGGTKLEIKR | SEQ ID NO: 114 |
| 18.3.3 | FGGGTRLEIKR | SEQ ID NO: 115 |
| PDL183 | FGQGTKVEIKR | SEQ ID NO: 116 |
| PDL183-2 | FGGGTRLEIKR | SEQ ID NO: 117 |
| ITEM-3 | FGGGTKMEIKR | SEQ ID NO: 118 |
| ITEM-1 | FGGGTKLEIKR | SEQ ID NO: 119 |

*FIG. 4G*

Consensus Sequences for Anti-Tweak R Antibodies

| | |
|---|---|
| Variable Heavy CDR1 | XYWMX (SEQ ID NO. 120) |
| Variable Heavy CDR2 | EIRLKSDNYATHYAESXKG (SEQ ID NO. 121) |
| Variable Heavy CDR3 | XXADXXDY (SEQ ID NO. 122) |
| Variable Heavy FR1 | EVXLXESGGGLVQPGGSXXLSCXASGFXFX (SEQ ID NO. 123) |
| Variable Heavy FR2 | WVRQXPXKGLEWXA (SEQ ID NO. 124) |
| Variable Heavy FR3 | XFTISRDXXXXXXYLQMNXLRAEXTXXYYCXX (SEQ ID NO. 125) |
| Variable Heavy FR4 | WGQGTXXTVSS (SEQ ID NO. 126) |
| Variable Light CDR1 | XASQSVSTSXYSYMX (SEQ ID NO. 127) |
| Variable Light CDR2 | YAXXLXS (SEQ ID NO. 128) |
| Variable Light CDR3 | QHSWEXPYT (SEQ ID NO. 129) |
| Variable Light FR1 | XIXXTQSPXSLXXSXGXRXTIXC (SEQ ID NO. 130) |
| Variable Light FR2 | WYQQXPGXXPKLLIK (SEQ ID NO. 131) |
| Variable Light FR3 | GXPXRFSGSGSGTDFTLXIXXXXXEDXAXYYC (SEQ ID NO. 132) |
| Variable Light FR4 | FGXGTXXEIKR (SEQ ID NO. 133) |

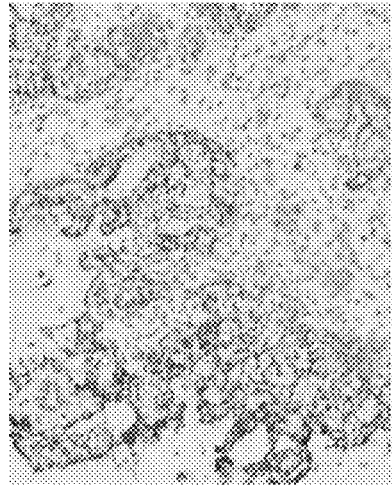
FIG. 7B — Pancreatic Cancer
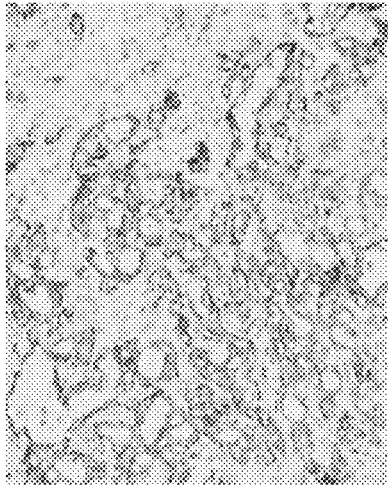
FIG. 7D — Pancreatic Cancer
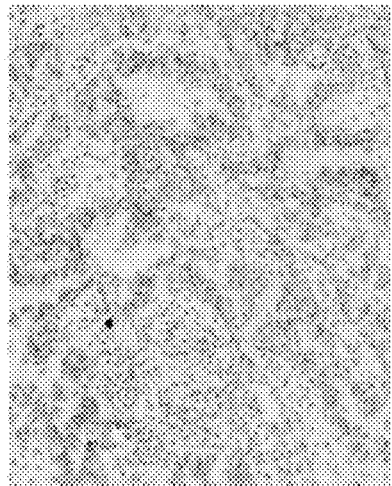
FIG. 7A — Lung Adenocarcinoma
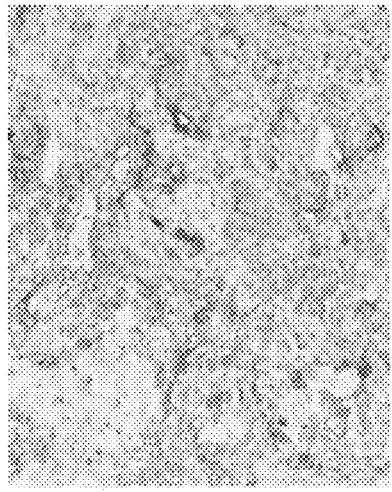
FIG. 7C — Lung Squamous Cell Carcinoma

SEQUENCE LISTING

<160> NUMBER OF SEQ ID NOS: 133

<210> SEQ ID NO 1
<211> LENGTH: 1043
<212> TYPE: DNA
<213> ORGANISM: Homo Sapiens

<400> SEQUENCE: 1

```
tcgacccacg cgtccgccca cgcgtccgcc cacgcgtccg ggcgcaggac gtgcactatg      60
gctcggggct cgctgcgccg gttgctgcgg ctcctcgtgc tggggctctg gctggcgttg     120
ctgcgctccg tggccgggga gcaagcgcca ggcaccgccc cctgctcccg cggcagctcc     180
tggagcgcgg acctggacaa gtgcatggac tgcgcgtctt gcagggcgcg accgcacagc     240
gacttctgcc tgggctgcgc tgcagcacct cctgcccct tccggctgct ttggcccatc     300 cttggggcg ctctgagcct gaccttcgtg ctggggctgc tttctggctt tttggtctgg     360
agacgatgcc gcaggagaga gaagttcacc acccccatag aggagaccgg cggagagggc     420
tgcccagctg tggcgctgat ccagtgacaa tgtgcccct gccagccggg gctcgcccac     480
tcatcattca ttcatccatt ctagagccag tctctgcctc ccagacgcgg cgggagccaa     540
gctcctccac cacaagggg gtgggggcg gtgaatcacc tctgaggcct gggcccaggg     600 ttcagggaa ccttccaagg tgtctggttg ccctgcctct ggctccagaa cagaaaggga     660
gcctcacgct ggctcacaca aaacagctga cactgactaa ggaactgcag catttgcaca     720
ggggaggggg gtgccctcct tcctagaggc cctggggggcc aggctgactt ggggggcaga     780
cttgacacta ggccccactc actcagatgt cctgaaattc caccacgggg gtcaccctgg     840
ggggttaggg acctattttt aacactaggg ggctggccca ctaggagggc tggccctaag     900
atacagaccc ccccaactcc ccaaagcggg gaggagatat ttattttggg gagagtttgg     960
aggggaggga gaatttatta ataaaagaat ctttaacttt aaaaaaaaaa aaaaaaaagg    1020
gcggccgctc tagaggatcc ctc                                             1043
```

<210> SEQ ID NO 2

<211> LENGTH: 129
<212> TYPE: PRT
<213> ORGANISM: Homo Sapiens

<400> SEQUENCE: 2

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln

<210> SEQ ID NO 3
<211> LENGTH: 119
<212> TYPE: PRT
<213> ORGANISM: Homo Sapiens

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Glu Ile Arg Leu Lys Ser Asp Asn Tyr Ala Thr His Tyr Ala Glu
50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Gly Tyr Tyr Ala Asp Ala Met Asp Tyr Trp Gly Gln Gly
            100                 105                 110

Thr Leu Val Thr Val Ser Ser
        115

<210> SEQ ID NO 4
<211> LENGTH: 111
<212> TYPE: PRT
<213> ORGANISM: Homo Sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

```
Ser Tyr Ser Tyr Met His Trp Tyr Gln Gln Lys Pro Gly Lys Ala Pro
        35                  40                  45

Lys Leu Leu Ile Lys Tyr Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Trp
                 85                  90                  95

Glu Ile Pro Tyr Thr Phe Gly Gly Gly Thr Lys Val Glu Ile Lys
            100                 105                 110

<210> SEQ ID NO 5
<211> LENGTH: 119
<212> TYPE: PRT
<213> ORGANISM: Mus Musculus

<400> SEQUENCE: 5

Glu Val Lys Leu Glu Glu Ser Gly Gly Gly Leu Val Gln Pro Gly Gly
 1               5                   10                  15

Ser Met Lys Leu Ser Cys Val Ala Ser Gly Phe Thr Phe Ser Ser Tyr
            20                  25                  30

Trp Met Ser Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
 50                  55                  60

Ser Val Lys Gly Lys Phe Thr Ile Ser Arg Asp Asp Ser Lys Ser Arg
 65                  70                  75                  80

Leu Tyr Leu Gln Met Asn Ser Leu Arg Ala Glu Asp Thr Gly Ile Tyr
                 85                  90                  95

Tyr Cys Thr Gly Tyr Tyr Ala Asp Ala Met Asp Tyr Trp Gly Gln Gly
            100                 105                 110

Thr Ser Val Thr Val Ser Ser
        115

<210> SEQ ID NO 6
<211> LENGTH: 111
<212> TYPE: PRT
<213> ORGANISM: Mus Musculus

<400> SEQUENCE: 6

Asp Ile Val Leu Thr Gln Ser Pro Ala Ser Leu Ala Val Ser Leu Gly
 1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Tyr Thr Phe Gly Gly Gly Thr Lys Leu Glu Ile Lys
            100                 105                 110

<210> SEQ ID NO 7
<211> LENGTH: 119
```

```
<212> TYPE: PRT
<213> ORGANISM: Mus Musculus

<400> SEQUENCE: 7

Glu Val Lys Leu Gly Glu Ser Gly Gly Gly Leu Val Gln Pro Gly Gly
1               5                   10                  15

Ser Met Lys Leu Ser Cys Val Ala Ser Gly Phe Pro Phe Thr Lys Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Ala Lys Gly Arg Phe Thr Ile Ser Arg Asp Asp Ser Arg Ser Ser
65                  70                  75                  80

Val Tyr Leu Gln Met Asn Asn Leu Arg Ala Glu Asp Thr Ala Ile Tyr
                85                  90                  95

Tyr Cys Ser Pro Thr Tyr Ala Asp Thr Met Asp Tyr Trp Gly Gln Gly
            100                 105                 110

Thr Ser Val Thr Val Ser Ser
        115

<210> SEQ ID NO 8
<211> LENGTH: 112
<212> TYPE: PRT
<213> ORGANISM: Mus Musculus

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Ser Thr Ser
            20                  25                  30

Thr Tyr Ser Tyr Met Gln Trp Tyr Gln Gln Arg Pro Gly Gln Ser Pro
        35                  40                  45

Lys Leu Leu Ile Lys Tyr Ala Ser Lys Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Leu Pro Tyr Thr Phe Gly Gly Gly Thr Arg Leu Glu Ile Lys Arg
            100                 105                 110

<210> SEQ ID NO 9
<211> LENGTH: 119
<212> TYPE: PRT
<213> ORGANISM: Mus Musculus

<400> SEQUENCE: 9

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Asn Asn Tyr
            20                  25                  30

Trp Met Ser Trp Val Arg Gln Ser Pro Glu Lys Gly Leu Glu Trp Leu
        35                  40                  45

Ala Glu Ile Arg Leu Lys Ser Asp Asn Tyr Ala Thr His Tyr Ala Glu
    50                  55                  60
```

```
Ser Val Lys Gly Lys Phe Thr Ile Ser Arg Asp Asp Ser Lys Ser Arg
 65                  70                  75                  80

Leu Tyr Leu Gln Met Asn Asn Leu Arg Ala Glu Asn Thr Gly Ile Tyr
                 85                  90                  95

Tyr Cys Thr Gly Gly Phe Ala Asp Tyr Phe Asp Tyr Trp Gly Gln Gly
            100                 105                 110

Thr Thr Leu Thr Val Ser Ser
            115

<210> SEQ ID NO 10
<211> LENGTH: 112
<212> TYPE: PRT
<213> ORGANISM: Mus Musculus

<400> SEQUENCE: 10

Asp Ile Val Leu Thr Gln Ser Pro Ala Ser Leu Thr Val Ser Leu Gly
 1               5                  10                  15

Gln Arg Ala Thr Ile Ser Cys Arg Ala Ser Gln Ser Val Ser Thr Ser
                20                  25                  30

Ser Tyr Ser Tyr Met Gln Trp Tyr Gln Gln Arg Pro Gly Gln Pro Pro
            35                  40                  45

Lys Leu Leu Ile Lys Tyr Ala Thr Asn Leu Asp Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Trp
                 85                  90                  95

Glu Ile Pro Tyr Thr Phe Gly Gly Gly Thr Lys Leu Glu Ile Lys Arg
            100                 105                 110

<210> SEQ ID NO 11
<211> LENGTH: 120
<212> TYPE: PRT
<213> ORGANISM: Homo Sapiens

<400> SEQUENCE: 11

Gln Val Gln Leu Val Gln Ser Gly Ala Glu Val Lys Lys Pro Gly Ala
 1               5                  10                  15

Ser Val Lys Ile Ser Cys Lys Val Ser Gly Tyr Thr Phe Thr Asp Phe
                20                  25                  30

Ile Ile Ala Trp Val Lys Gln Ala Pro Gly Lys Gly Leu Glu Trp Ile
            35                  40                  45

Gly Glu Ile Tyr Pro Gly Thr Gly Arg Thr Tyr Tyr Ser Glu Lys Phe
 50                  55                  60

Arg Gly Lys Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Thr Ile Tyr Tyr Asp Tyr Asp Gly Asp Tyr Trp Gly Gln
            100                 105                 110

Gly Thr Thr Val Thr Val Ser Ser
            115                 120

<210> SEQ ID NO 12
<211> LENGTH: 112
<212> TYPE: PRT
<213> ORGANISM: Homo Sapiens
```

```
<400> SEQUENCE: 12

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gly Gly Thr Lys Val Glu Ile Lys
            100                 105                 110

<210> SEQ ID NO 13
<211> LENGTH: 5
<212> TYPE: PRT
<213> ORGANISM: Homo Sapiens

<400> SEQUENCE: 13

Ser Tyr Trp Met Ser
1               5

<210> SEQ ID NO 14
<211> LENGTH: 5
<212> TYPE: PRT
<213> ORGANISM: Mus Musculus

<400> SEQUENCE: 14

Ser Tyr Trp Met Ser
1               5

<210> SEQ ID NO 15
<211> LENGTH: 5
<212> TYPE: PRT
<213> ORGANISM: Mus Musculus

<400> SEQUENCE: 15

Asn Tyr Trp Met Ser
1               5

<210> SEQ ID NO 16
<211> LENGTH: 5
<212> TYPE: PRT
<213> ORGANISM: Mus Musculus

<400> SEQUENCE: 16

Lys Tyr Trp Met Asn
1               5

<210> SEQ ID NO 17
<211> LENGTH: 5
<212> TYPE: PRT
<213> ORGANISM: Mus Musculus

<400> SEQUENCE: 17

Arg Tyr Trp Met Ser
1               5
```

```
<210> SEQ ID NO 18
<211> LENGTH: 5
<212> TYPE: PRT
<213> ORGANISM: Mus Musculus

<400> SEQUENCE: 18

Asn Tyr Trp Met Asn
1               5

<210> SEQ ID NO 19
<211> LENGTH: 19
<212> TYPE: PRT
<213> ORGANISM: Homo Sapiens

<400> SEQUENCE: 19

Glu Ile Arg Leu Lys Ser Asp Asn Tyr Ala Thr His Tyr Ala Glu Ser
1               5                   10                  15

Val Lys Gly

<210> SEQ ID NO 20
<211> LENGTH: 19
<212> TYPE: PRT
<213> ORGANISM: Mus Musculus

<400> SEQUENCE: 20

Glu Ile Arg Leu Lys Ser Asp Asn Tyr Ala Thr His Tyr Ala Glu Ser
1               5                   10                  15

Val Lys Gly

<210> SEQ ID NO 21
<211> LENGTH: 19
<212> TYPE: PRT
<213> ORGANISM: Mus Musculus

<400> SEQUENCE: 21

Glu Ile Arg Leu Lys Ser Asp Asn Tyr Ala Thr His Tyr Ala Glu Ser
1               5                   10                  15

Val Lys Gly

<210> SEQ ID NO 22
<211> LENGTH: 19
<212> TYPE: PRT
<213> ORGANISM: Mus Musculus

<400> SEQUENCE: 22

Glu Ile Arg Leu Lys Ser Asp Asn Tyr Ala Thr His Tyr Ala Glu Ser
1               5                   10                  15

Ala Lys Gly

<210> SEQ ID NO 23
<211> LENGTH: 20
<212> TYPE: PRT
<213> ORGANISM: Mus Musculus

<400> SEQUENCE: 23

Glu Ile Arg Val Lys Ser Asp Asn Tyr Ala Thr Thr His Tyr Ala Glu
1               5                   10                  15

Ser Val Lys Gly
            20

<210> SEQ ID NO 24
<211> LENGTH: 19
```

```
<212> TYPE: PRT
<213> ORGANISM: Mus Musculus

<400> SEQUENCE: 24

Glu Ile Arg Leu Lys Ser Asn Asn Tyr Ala Thr His Tyr Ala Glu Ser
1               5                   10                  15

Val Lys Gly

<210> SEQ ID NO 25
<211> LENGTH: 8
<212> TYPE: PRT
<213> ORGANISM: Homo Sapiens

<400> SEQUENCE: 25

Tyr Tyr Ala Asp Ala Met Asp Tyr
1               5

<210> SEQ ID NO 26
<211> LENGTH: 8
<212> TYPE: PRT
<213> ORGANISM: Mus Musculus

<400> SEQUENCE: 26

Tyr Tyr Ala Asp Ala Met Asp Tyr
1               5

<210> SEQ ID NO 27
<211> LENGTH: 8
<212> TYPE: PRT
<213> ORGANISM: Mus Musculus

<400> SEQUENCE: 27

Gly Phe Ala Asp Tyr Phe Asp Tyr
1               5

<210> SEQ ID NO 28
<211> LENGTH: 8
<212> TYPE: PRT
<213> ORGANISM: Mus Musculus

<400> SEQUENCE: 28

Thr Tyr Ala Asp Thr Met Asp Tyr
1               5

<210> SEQ ID NO 29
<211> LENGTH: 8
<212> TYPE: PRT
<213> ORGANISM: Mus Musculus

<400> SEQUENCE: 29

Tyr Tyr Ala Asp Ala Met Asp Tyr
1               5

<210> SEQ ID NO 30
<211> LENGTH: 8
<212> TYPE: PRT
<213> ORGANISM: Mus Musculus

<400> SEQUENCE: 30

Ala Tyr Ala Asp Tyr Phe Asp Tyr
1               5

<210> SEQ ID NO 31
<211> LENGTH: 30
```

-continued

```
<212> TYPE: PRT
<213> ORGANISM: Homo Sapiens

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 32
<211> LENGTH: 30
<212> TYPE: PRT
<213> ORGANISM: Homo Sapiens

<400> SEQUENCE: 32

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser
            20                  25                  30

<210> SEQ ID NO 33
<211> LENGTH: 30
<212> TYPE: PRT
<213> ORGANISM: Mus Musculus

<400> SEQUENCE: 33

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser
            20                  25                  30

<210> SEQ ID NO 34
<211> LENGTH: 30
<212> TYPE: PRT
<213> ORGANISM: Mus Musculus

<400> SEQUENCE: 34

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Asn
            20                  25                  30

<210> SEQ ID NO 35
<211> LENGTH: 30
<212> TYPE: PRT
<213> ORGANISM: Mus Musculus

<400> SEQUENCE: 35

Glu Val Lys Leu Gly Glu Ser Gly Gly Gly Leu Val Gln Pro Gly Gly
1               5                   10                  15

Ser Met Lys Leu Ser Cys Val Ala Ser Gly Phe Pro Phe Thr
            20                  25                  30

<210> SEQ ID NO 36
<211> LENGTH: 30
<212> TYPE: PRT
<213> ORGANISM: Homo Sapiens

<400> SEQUENCE: 36

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Pro Phe Thr
            20                  25                  30
```

<210> SEQ ID NO 37
<211> LENGTH: 30
<212> TYPE: PRT
<213> ORGANISM: Homo Sapiens

<400> SEQUENCE: 37

```
Glu Val Lys Leu Glu Ser Gly Gly Gly Leu Val Gln Pro Gly Gly
1               5                   10                  15

Ser Met Lys Leu Ser Cys Val Ala Ser Gly Phe Thr Phe Ser
            20                  25                  30
```

<210> SEQ ID NO 38
<211> LENGTH: 30
<212> TYPE: PRT
<213> ORGANISM: Mus Musculus

<400> SEQUENCE: 38

```
Glu Val Lys Leu Glu Glu Ser Gly Gly Gly Leu Val Gln Pro Gly Gly
1               5                   10                  15

Ser Met Lys Leu Ser Cys Val Val Ser Gly Leu Thr Phe Ser
            20                  25                  30
```

<210> SEQ ID NO 39
<211> LENGTH: 30
<212> TYPE: PRT
<213> ORGANISM: Mus Musculus

<400> SEQUENCE: 39

```
Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ser Phe Ser
            20                  25                  30
```

<210> SEQ ID NO 40
<211> LENGTH: 14
<212> TYPE: PRT
<213> ORGANISM: Homo Sapiens

<400> SEQUENCE: 40

```
Trp Val Arg Gln Ala Pro Gly Lys Gly Leu Glu Trp Val Ala
1               5                   10
```

<210> SEQ ID NO 41
<211> LENGTH: 14
<212> TYPE: PRT
<213> ORGANISM: Homo Sapiens

<400> SEQUENCE: 41

```
Trp Val Arg Gln Ser Pro Glu Lys Gly Leu Glu Trp Val Ala
1               5                   10
```

<210> SEQ ID NO 42
<211> LENGTH: 14
<212> TYPE: PRT
<213> ORGANISM: Mus Musculus

<400> SEQUENCE: 42

```
Trp Val Arg Gln Ser Pro Glu Lys Gly Leu Glu Trp Val Ala
1               5                   10
```

```
<210> SEQ ID NO 43
<211> LENGTH: 14
<212> TYPE: PRT
<213> ORGANISM: Mus Musculus

<400> SEQUENCE: 43

Trp Val Arg Gln Ser Pro Glu Lys Gly Leu Glu Trp Leu Ala
1               5                   10

<210> SEQ ID NO 44
<211> LENGTH: 14
<212> TYPE: PRT
<213> ORGANISM: Mus Musculus

<400> SEQUENCE: 44

Trp Val Arg Gln Ser Pro Glu Lys Gly Leu Glu Trp Val Ala
1               5                   10

<210> SEQ ID NO 45
<211> LENGTH: 14
<212> TYPE: PRT
<213> ORGANISM: Homo Sapiens

<400> SEQUENCE: 45

Trp Val Arg Gln Ala Pro Gly Lys Gly Leu Glu Trp Val Ala
1               5                   10

<210> SEQ ID NO 46
<211> LENGTH: 14
<212> TYPE: PRT
<213> ORGANISM: Homo Sapiens

<400> SEQUENCE: 46

Trp Val Arg Gln Ser Pro Glu Lys Gly Leu Glu Trp Val Ser
1               5                   10

<210> SEQ ID NO 47
<211> LENGTH: 14
<212> TYPE: PRT
<213> ORGANISM: Mus Musculus

<400> SEQUENCE: 47

Trp Val Arg Gln Ser Pro Glu Lys Gly Leu Glu Trp Val Ala
1               5                   10

<210> SEQ ID NO 48
<211> LENGTH: 14
<212> TYPE: PRT
<213> ORGANISM: Mus Musculus

<400> SEQUENCE: 48

Trp Val Arg Gln Ser Pro Glu Lys Gly Leu Glu Trp Val Ala
1               5                   10

<210> SEQ ID NO 49
<211> LENGTH: 32
<212> TYPE: PRT
<213> ORGANISM: Homo Sapiens

<400> SEQUENCE: 49

Arg Phe Thr Ile Ser Arg Asp Asp Ser Lys Asn Ser Leu Tyr Leu Gln
1               5                   10                  15

Met Asn Ser Leu Arg Ala Glu Asp Thr Ala Val Tyr Tyr Cys Thr Gly
            20                  25                  30
```

<210> SEQ ID NO 50
<211> LENGTH: 32
<212> TYPE: PRT
<213> ORGANISM: Homo Sapiens

<400> SEQUENCE: 50

Lys Phe Thr Ile Ser Arg Asp Asn Ala Lys Ser Arg Leu Tyr Leu Gln
1               5                   10                  15

Met Asn Ser Leu Arg Ala Glu Asp Thr Gly Ile Tyr Tyr Cys Ala Arg
            20                  25                  30

<210> SEQ ID NO 51
<211> LENGTH: 32
<212> TYPE: PRT
<213> ORGANISM: Mus Musculus

<400> SEQUENCE: 51

Lys Phe Thr Ile Ser Arg Asp Asp Ser Lys Ser Arg Leu Tyr Leu Gln
1               5                   10                  15

Met Asn Ser Leu Arg Ala Glu Asp Thr Gly Ile Tyr Tyr Cys Thr Gly
            20                  25                  30

<210> SEQ ID NO 52
<211> LENGTH: 32
<212> TYPE: PRT
<213> ORGANISM: Mus Musculus

<400> SEQUENCE: 52

Lys Phe Thr Ile Ser Arg Asp Asp Ser Lys Ser Arg Leu Tyr Leu Gln
1               5                   10                  15

Met Asn Asn Leu Arg Ala Glu Asn Thr Gly Ile Tyr Tyr Cys Thr Gly
            20                  25                  30

<210> SEQ ID NO 53
<211> LENGTH: 32
<212> TYPE: PRT
<213> ORGANISM: Mus Musculus

<400> SEQUENCE: 53

Arg Phe Thr Ile Ser Arg Asp Asp Ser Arg Ser Val Tyr Leu Gln
1               5                   10                  15

Met Asn Asn Leu Arg Ala Glu Asp Thr Ala Ile Tyr Tyr Cys Ser Pro
            20                  25                  30

<210> SEQ ID NO 54
<211> LENGTH: 32
<212> TYPE: PRT
<213> ORGANISM: Homo Sapiens

<400> SEQUENCE: 54

Arg Phe Thr Ile Ser Arg Asp Asp Ser Lys Asn Thr Val Tyr Leu Gln
1               5                   10                  15

Met Asn Ser Leu Arg Ala Glu Asp Thr Ala Val Tyr Tyr Cys Ser Pro
            20                  25                  30

<210> SEQ ID NO 55
<211> LENGTH: 32
<212> TYPE: PRT
<213> ORGANISM: Homo Sapiens

<400> SEQUENCE: 55

Arg Phe Thr Ile Ser Arg Asp Asn Ala Arg Ser Ser Leu Tyr Leu Gln
1               5                   10                  15

Met Asn Asn Leu Arg Ala Glu Asp Thr Ala Ile Tyr Tyr Cys Ala Arg
            20                  25                  30

<210> SEQ ID NO 56
<211> LENGTH: 32
<212> TYPE: PRT
<213> ORGANISM: Mus Musculus

<400> SEQUENCE: 56

Lys Phe Thr Val Ser Arg Asp Asp Ser Lys Ser Arg Leu Tyr Leu Gln
1               5                   10                  15

Met Ser Ser Leu Arg Pro Glu Asp Thr Gly Ile Tyr Tyr Cys Ile Gly
            20                  25                  30

<210> SEQ ID NO 57
<211> LENGTH: 32
<212> TYPE: PRT
<213> ORGANISM: Mus Musculus

<400> SEQUENCE: 57

Arg Phe Thr Ile Ser Arg His Asp Ser Lys Ser Ser Val Tyr Leu Gln
1               5                   10                  15

Met Asn Asn Leu Arg Ala Glu Asp Thr Gly Ile Tyr Tyr Cys Thr Arg
            20                  25                  30

<210> SEQ ID NO 58
<211> LENGTH: 11
<212> TYPE: PRT
<213> ORGANISM: Homo Sapiens

<400> SEQUENCE: 58

Trp Gly Gln Gly Thr Leu Val Thr Val Ser Ser
1               5                   10

<210> SEQ ID NO 59
<211> LENGTH: 11
<212> TYPE: PRT
<213> ORGANISM: Mus Musculus

<400> SEQUENCE: 59

Trp Gly Gln Gly Thr Ser Val Thr Val Ser Ser
1               5                   10

<210> SEQ ID NO 60
<211> LENGTH: 11
<212> TYPE: PRT
<213> ORGANISM: Mus Musculus

<400> SEQUENCE: 60

Trp Gly Gln Gly Thr Thr Leu Thr Val Ser Ser
1               5                   10

<210> SEQ ID NO 61
<211> LENGTH: 11
<212> TYPE: PRT
<213> ORGANISM: Mus Musculus

<400> SEQUENCE: 61

Trp Gly Gln Gly Thr Ser Val Thr Val Ser Ser
1               5                   10

```
<210> SEQ ID NO 62
<211> LENGTH: 11
<212> TYPE: PRT
<213> ORGANISM: Homo Sapiens

<400> SEQUENCE: 62

Trp Gly Gln Gly Thr Leu Val Thr Val Ser Ser
1               5                   10

<210> SEQ ID NO 63
<211> LENGTH: 11
<212> TYPE: PRT
<213> ORGANISM: Homo Sapiens

<400> SEQUENCE: 63

Trp Gly Gln Gly Thr Ser Val Thr Val Ser Ser
1               5                   10

<210> SEQ ID NO 64
<211> LENGTH: 11
<212> TYPE: PRT
<213> ORGANISM: Mus Musculus

<400> SEQUENCE: 64

Trp Gly Gln Gly Thr Ser Val Thr Val Ser Ser
1               5                   10

<210> SEQ ID NO 65
<211> LENGTH: 11
<212> TYPE: PRT
<213> ORGANISM: Mus Musculus

<400> SEQUENCE: 65

Trp Gly Gln Gly Thr Thr Leu Thr Val Ser Ser
1               5                   10

<210> SEQ ID NO 66
<211> LENGTH: 15
<212> TYPE: PRT
<213> ORGANISM: Homo Sapiens

<400> SEQUENCE: 66

Arg Ala Ser Gln Ser Val Ser Thr Ser Ser Tyr Ser Tyr Met His
1               5                   10                  15

<210> SEQ ID NO 67
<211> LENGTH: 15
<212> TYPE: PRT
<213> ORGANISM: Mus Musculus

<400> SEQUENCE: 67

Arg Ala Ser Gln Ser Val Ser Thr Ser Ser Tyr Ser Tyr Met His
1               5                   10                  15

<210> SEQ ID NO 68
<211> LENGTH: 15
<212> TYPE: PRT
<213> ORGANISM: Mus Musculus

<400> SEQUENCE: 68

Arg Ala Ser Gln Ser Val Ser Thr Ser Ser Tyr Ser Tyr Met Gln
1               5                   10                  15

<210> SEQ ID NO 69
<211> LENGTH: 15
```

```
<212> TYPE: PRT
<213> ORGANISM: Mus Musculus

<400> SEQUENCE: 69

Lys Ala Ser Gln Ser Val Ser Thr Ser Thr Tyr Ser Tyr Met Gln
1               5                   10                  15

<210> SEQ ID NO 70
<211> LENGTH: 15
<212> TYPE: PRT
<213> ORGANISM: Mus Musculus

<400> SEQUENCE: 70

Arg Ala Ser Gln Ser Val Ser Thr Ser Ser Tyr Ser Tyr Met His
1               5                   10                  15

<210> SEQ ID NO 71
<211> LENGTH: 15
<212> TYPE: PRT
<213> ORGANISM: Mus Musculus

<400> SEQUENCE: 71

Arg Ala Ser Gln Ser Val Ser Thr Ser Thr Tyr Ser Tyr Met His
1               5                   10                  15

<210> SEQ ID NO 72
<211> LENGTH: 7
<212> TYPE: PRT
<213> ORGANISM: Homo Sapiens

<400> SEQUENCE: 72

Tyr Ala Ser Asn Leu Glu Ser
1               5

<210> SEQ ID NO 73
<211> LENGTH: 7
<212> TYPE: PRT
<213> ORGANISM: Mus Musculus

<400> SEQUENCE: 73

Tyr Ala Ser Asn Leu Glu Ser
1               5

<210> SEQ ID NO 74
<211> LENGTH: 7
<212> TYPE: PRT
<213> ORGANISM: Mus Musculus

<400> SEQUENCE: 74

Tyr Ala Thr Asn Leu Asp Ser
1               5

<210> SEQ ID NO 75
<211> LENGTH: 7
<212> TYPE: PRT
<213> ORGANISM: Mus Musculus

<400> SEQUENCE: 75

Tyr Ala Ser Lys Leu Asp Ser
1               5

<210> SEQ ID NO 76
<211> LENGTH: 7
<212> TYPE: PRT
<213> ORGANISM: Mus Musculus
```

<400> SEQUENCE: 76

Tyr Ala Ser Lys Leu Asp Ser
1               5

<210> SEQ ID NO 77
<211> LENGTH: 7
<212> TYPE: PRT
<213> ORGANISM: Mus Musculus

<400> SEQUENCE: 77

Tyr Ala Ser Asn Leu Glu Ser
1               5

<210> SEQ ID NO 78
<211> LENGTH: 9
<212> TYPE: PRT
<213> ORGANISM: Homo Sapiens

<400> SEQUENCE: 78

Gln His Ser Trp Glu Ile Pro Tyr Thr
1               5

<210> SEQ ID NO 79
<211> LENGTH: 9
<212> TYPE: PRT
<213> ORGANISM: Mus Musculus

<400> SEQUENCE: 79

Gln His Ser Trp Glu Ile Pro Tyr Thr
1               5

<210> SEQ ID NO 80
<211> LENGTH: 9
<212> TYPE: PRT
<213> ORGANISM: Mus Musculus

<400> SEQUENCE: 80

Gln His Ser Trp Glu Ile Pro Tyr Thr
1               5

<210> SEQ ID NO 81
<211> LENGTH: 9
<212> TYPE: PRT
<213> ORGANISM: Mus Musculus

<400> SEQUENCE: 81

Gln His Ser Trp Glu Leu Pro Tyr Thr
1               5

<210> SEQ ID NO 82
<211> LENGTH: 9
<212> TYPE: PRT
<213> ORGANISM: Mus Musculus

<400> SEQUENCE: 82

Gln His Ser Trp Glu Ile Pro Trp Thr
1               5

<210> SEQ ID NO 83
<211> LENGTH: 9
<212> TYPE: PRT
<213> ORGANISM: Mus Musculus

<400> SEQUENCE: 83

```
Gln His Ser Trp Glu Ile Pro Tyr Thr
1               5

<210> SEQ ID NO 84
<211> LENGTH: 23
<212> TYPE: PRT
<213> ORGANISM: Homo Sapiens

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 85
<211> LENGTH: 23
<212> TYPE: PRT
<213> ORGANISM: Homo Sapiens

<400> SEQUENCE: 85

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 86
<211> LENGTH: 23
<212> TYPE: PRT
<213> ORGANISM: Mus Musculus

<400> SEQUENCE: 86

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 87
<211> LENGTH: 23
<212> TYPE: PRT
<213> ORGANISM: Mus Musculus

<400> SEQUENCE: 87

Asp Ile Val Leu Thr Gln Ser Pro Ala Ser Leu Thr Val Ser Leu Gly
1               5                   10                  15

Gln Arg Ala Thr Ile Ser Cys
            20

<210> SEQ ID NO 88
<211> LENGTH: 23
<212> TYPE: PRT
<213> ORGANISM: Mus Musculus

<400> SEQUENCE: 88

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 89
<211> LENGTH: 23
<212> TYPE: PRT
<213> ORGANISM: Homo Sapiens
```

<400> SEQUENCE: 89

Asp Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 90
<211> LENGTH: 23
<212> TYPE: PRT
<213> ORGANISM: Homo Sapiens

<400> SEQUENCE: 90

Glu Ile Val Met Thr Gln Ser Pro Ala Ser Leu Ala Val Ser Leu Gly
1               5                   10                  15

Gln Arg Ala Thr Ile Ser Cys
            20

<210> SEQ ID NO 91
<211> LENGTH: 23
<212> TYPE: PRT
<213> ORGANISM: Mus Musculus

<400> SEQUENCE: 91

Asp Ile Val Leu Thr Gln Ser Pro Ala Ser Leu Val Val Ser Leu Gly
1               5                   10                  15

Gln Arg Ala Thr Ile Ser Cys
            20

<210> SEQ ID NO 92
<211> LENGTH: 23
<212> TYPE: PRT
<213> ORGANISM: Mus Musculus

<400> SEQUENCE: 92

Asp Ile Val Leu Thr Gln Ser Pro Ala Ser Leu Val Val Ser Leu Gly
1               5                   10                  15

Gln Arg Ala Thr Ile Ser Cys
            20

<210> SEQ ID NO 93
<211> LENGTH: 15
<212> TYPE: PRT
<213> ORGANISM: Homo Sapiens

<400> SEQUENCE: 93

Trp Tyr Gln Gln Lys Pro Gly Lys Ala Pro Lys Leu Leu Ile Lys
1               5                   10                  15

<210> SEQ ID NO 94
<211> LENGTH: 15
<212> TYPE: PRT
<213> ORGANISM: Homo Sapiens

<400> SEQUENCE: 94

Trp Tyr Gln Gln Lys Pro Gly Gln Pro Pro Lys Leu Leu Ile Tyr
1               5                   10                  15

<210> SEQ ID NO 95
<211> LENGTH: 15
<212> TYPE: PRT
<213> ORGANISM: Mus Musculus

```
<400> SEQUENCE: 95

Trp Tyr Gln Gln Lys Pro Gly Gln Pro Pro Lys Leu Leu Ile Lys
1               5                   10                  15

<210> SEQ ID NO 96
<211> LENGTH: 15
<212> TYPE: PRT
<213> ORGANISM: Mus Musculus

<400> SEQUENCE: 96

Trp Tyr Gln Gln Arg Pro Gly Gln Pro Pro Lys Leu Leu Ile Lys
1               5                   10                  15

<210> SEQ ID NO 97
<211> LENGTH: 15
<212> TYPE: PRT
<213> ORGANISM: Mus Musculus

<400> SEQUENCE: 97

Trp Tyr Gln Gln Arg Pro Gly Gln Ser Pro Lys Leu Leu Ile Lys
1               5                   10                  15

<210> SEQ ID NO 98
<211> LENGTH: 15
<212> TYPE: PRT
<213> ORGANISM: Homo Sapiens

<400> SEQUENCE: 98

Trp Val Gln Gln Lys Pro Gly Gln Ala Pro Arg Leu Leu Ile Lys
1               5                   10                  15

<210> SEQ ID NO 99
<211> LENGTH: 15
<212> TYPE: PRT
<213> ORGANISM: Homo Sapiens

<400> SEQUENCE: 99

Trp Tyr Gln Gln Arg Pro Gly Gln Ser Pro Lys Leu Leu Ile Tyr
1               5                   10                  15

<210> SEQ ID NO 100
<211> LENGTH: 15
<212> TYPE: PRT
<213> ORGANISM: Mus Musculus

<400> SEQUENCE: 100

Trp Tyr Gln Gln Lys Pro Gly Gln Pro Pro Lys Leu Leu Ile Lys
1               5                   10                  15

<210> SEQ ID NO 101
<211> LENGTH: 15
<212> TYPE: PRT
<213> ORGANISM: Mus Musculus

<400> SEQUENCE: 101

Trp Tyr Gln Gln Lys Pro Gly Gln Pro Pro Lys Ile Leu Ile Lys
1               5                   10                  15

<210> SEQ ID NO 102
<211> LENGTH: 32
<212> TYPE: PRT
<213> ORGANISM: Homo Sapiens

<400> SEQUENCE: 102
```

-continued

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 103
<211> LENGTH: 32
<212> TYPE: PRT
<213> ORGANISM: Homo Sapiens

<400> SEQUENCE: 103

Gly Val Pro Ala Arg Phe Ser Gly Ser Gly Ser Gly Thr Asp Phe Thr
1               5                   10                  15

Leu Asn Ile His Pro Val Glu Glu Glu Asp Thr Ala Thr Tyr Tyr Cys
            20                  25                  30

<210> SEQ ID NO 104
<211> LENGTH: 32
<212> TYPE: PRT
<213> ORGANISM: Mus Musculus

<400> SEQUENCE: 104

Gly Val Pro Ala Arg Phe Ser Gly Ser Gly Ser Gly Thr Asp Phe Thr
1               5                   10                  15

Leu Asn Ile His Pro Val Glu Glu Glu Asp Thr Ala Thr Tyr Tyr Cys
            20                  25                  30

<210> SEQ ID NO 105
<211> LENGTH: 32
<212> TYPE: PRT
<213> ORGANISM: Mus Musculus

<400> SEQUENCE: 105

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30

<210> SEQ ID NO 106
<211> LENGTH: 32
<212> TYPE: PRT
<213> ORGANISM: Mus Musculus

<400> SEQUENCE: 106

Gly Val Pro Ala Arg Phe Ser Gly Ser Gly Ser Gly Thr Asp Phe Thr
1               5                   10                  15

Leu Asn Ile His Pro Val Glu Glu Glu Asp Thr Ala Thr Tyr Tyr Cys
            20                  25                  30

<210> SEQ ID NO 107
<211> LENGTH: 32
<212> TYPE: PRT
<213> ORGANISM: Homo Sapiens

<400> SEQUENCE: 107

Gly Val Pro Ala Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 108
<211> LENGTH: 32

```
<212> TYPE: PRT
<213> ORGANISM: Homo Sapiens

<400> SEQUENCE: 108

Gly Ile Pro Asp Arg Phe Ser Gly Ser Gly Ser Gly Thr Asp Phe Thr
1               5                   10                  15

Leu Asn Ile His Pro Val Gln Glu Glu Asp Thr Ala Thr Tyr Tyr Cys
            20                  25                  30

<210> SEQ ID NO 109
<211> LENGTH: 32
<212> TYPE: PRT
<213> ORGANISM: Mus Musculus

<400> SEQUENCE: 109

Gly Val Pro Ala Arg Phe Ser Gly Ser Gly Ser Gly Thr Asp Phe Thr
1               5                   10                  15

Leu Asn Ile His Pro Val Glu Glu Glu Asp Thr Ala Thr Tyr Tyr Cys
            20                  25                  30

<210> SEQ ID NO 110
<211> LENGTH: 32
<212> TYPE: PRT
<213> ORGANISM: Mus Musculus

<400> SEQUENCE: 110

Gly Val Pro Ala Arg Phe Ser Gly Ser Gly Ser Gly Thr Asp Phe Thr
1               5                   10                  15

Leu Asn Ile His Pro Val Glu Glu Glu Asp Thr Ala Thr Tyr Tyr Cys
            20                  25                  30

<210> SEQ ID NO 111
<211> LENGTH: 11
<212> TYPE: PRT
<213> ORGANISM: Homo Sapiens

<400> SEQUENCE: 111

Phe Gly Gly Gly Thr Lys Val Glu Ile Lys Arg
1               5                   10

<210> SEQ ID NO 112
<211> LENGTH: 11
<212> TYPE: PRT
<213> ORGANISM: Homo Sapiens

<400> SEQUENCE: 112

Phe Gly Gly Gly Thr Lys Leu Glu Ile Lys Arg
1               5                   10

<210> SEQ ID NO 113
<211> LENGTH: 11
<212> TYPE: PRT
<213> ORGANISM: Mus Musculus

<400> SEQUENCE: 113

Phe Gly Gly Gly Thr Lys Leu Glu Ile Lys Arg
1               5                   10

<210> SEQ ID NO 114
<211> LENGTH: 11
<212> TYPE: PRT
<213> ORGANISM: Mus Musculus

<400> SEQUENCE: 114
```

```
Phe Gly Gly Gly Thr Lys Leu Glu Ile Lys Arg
1               5                   10
```

<210> SEQ ID NO 115
<211> LENGTH: 11
<212> TYPE: PRT
<213> ORGANISM: Mus Musculus

<400> SEQUENCE: 115

```
Phe Gly Gly Gly Thr Arg Leu Glu Ile Lys Arg
1               5                   10
```

<210> SEQ ID NO 116
<211> LENGTH: 11
<212> TYPE: PRT
<213> ORGANISM: Homo Sapiens

<400> SEQUENCE: 116

```
Phe Gly Gln Gly Thr Lys Val Glu Ile Lys Arg
1               5                   10
```

<210> SEQ ID NO 117
<211> LENGTH: 11
<212> TYPE: PRT
<213> ORGANISM: Homo Sapiens

<400> SEQUENCE: 117

```
Phe Gly Gly Gly Thr Arg Leu Glu Ile Lys Arg
1               5                   10
```

<210> SEQ ID NO 118
<211> LENGTH: 11
<212> TYPE: PRT
<213> ORGANISM: Mus Musculus

<400> SEQUENCE: 118

```
Phe Gly Gly Gly Thr Lys Met Glu Ile Lys Arg
1               5                   10
```

<210> SEQ ID NO 119
<211> LENGTH: 11
<212> TYPE: PRT
<213> ORGANISM: Mus Musculus

<400> SEQUENCE: 119

```
Phe Gly Gly Gly Thr Lys Leu Glu Ile Lys Arg
1               5                   10
```

<210> SEQ ID NO 120
<211> LENGTH: 5
<212> TYPE: PRT
<213> ORGANISM: Mus Musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 120

```
Xaa Tyr Trp Met Xaa
1               5
```

```
<210> SEQ ID NO 121
<211> LENGTH: 19
<212> TYPE: PRT
<213> ORGANISM: Mus Musculus
<220> FEATURE:
<221> NAME/KEY: misc_feature
<222> LOCATION: (17)..(17)
<223> OTHER INFORMATION: Xaa can be any naturally occurring amino acid

<400> SEQUENCE: 121

Glu Ile Arg Leu Lys Ser Asp Asn Tyr Ala Thr His Tyr Ala Glu Ser
1               5                   10                  15

Xaa Lys Gly

<210> SEQ ID NO 122
<211> LENGTH: 8
<212> TYPE: PRT
<213> ORGANISM: Mus Musculus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 122

Xaa Xaa Ala Asp Xaa Xaa Asp Tyr
1               5

<210> SEQ ID NO 123
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 123

Glu Val Xaa Leu Xaa Glu Ser Gly Gly Gly Leu Val Gln Pro Gly Gly
1               5                   10                  15

Ser Xaa Xaa Leu Ser Cys Xaa Ala Ser Gly Phe Xaa Phe Xaa
            20                  25                  30

<210> SEQ ID NO 124
<211> LENGTH: 14
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 124

Trp Val Arg Gln Xaa Pro Xaa Lys Gly Leu Glu Trp Xaa Ala
1               5                   10

<210> SEQ ID NO 125
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(13)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid

<400> SEQUENCE: 125

Xaa Phe Thr Ile Ser Arg Asp Xaa Xaa Xaa Xaa Xaa Xaa Tyr Leu Gln
1               5                   10                  15

Met Asn Xaa Leu Arg Ala Glu Xaa Thr Xaa Xaa Tyr Tyr Cys Xaa Xaa
            20                  25                  30

<210> SEQ ID NO 126
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(7)
<223> OTHER INFORMATION: Xaa can be any naturally occurring amino acid

<400> SEQUENCE: 126

Trp Gly Gln Gly Thr Xaa Xaa Thr Val Ser Ser
1               5                   10
```

```
<210> SEQ ID NO 127
<211> LENGTH: 15
<212> TYPE: PRT
<213> ORGANISM: Mus Musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 127

Xaa Ala Ser Gln Ser Val Ser Thr Ser Xaa Tyr Ser Tyr Met Xaa
1               5                   10                  15

<210> SEQ ID NO 128
<211> LENGTH: 7
<212> TYPE: PRT
<213> ORGANISM: Mus Musculus
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 128

Tyr Ala Xaa Xaa Leu Xaa Ser
1               5

<210> SEQ ID NO 129
<211> LENGTH: 9
<212> TYPE: PRT
<213> ORGANISM: Mus Musculus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 129

Gln His Ser Trp Glu Xaa Pro Tyr Thr
1               5

<210> SEQ ID NO 130
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
```

```
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 130

Xaa Ile Xaa Xaa Thr Gln Ser Pro Xaa Ser Leu Xaa Xaa Ser Xaa Gly
1               5                   10                  15

Xaa Arg Xaa Thr Ile Xaa Cys
            20

<210> SEQ ID NO 131
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 131

Trp Tyr Gln Gln Xaa Pro Gly Xaa Xaa Pro Lys Leu Leu Ile Lys
1               5                   10                  15

<210> SEQ ID NO 132
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(24)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 132
```

```
Gly Xaa Pro Xaa Arg Phe Ser Gly Ser Gly Thr Asp Phe Thr
1               5                   10                  15

Leu Xaa Ile Xaa Xaa Xaa Xaa Glu Asp Xaa Ala Xaa Tyr Tyr Cys
            20                  25              30

<210> SEQ ID NO 133
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 133

Phe Gly Xaa Gly Thr Xaa Xaa Glu Ile Lys Arg
1               5                   10
```

THERAPEUTIC USE OF ANTI-TWEAK RECEPTOR ANTIBODIES

1. CROSS REFERENCE TO RELATED APPLICATIONS

This application claims benefit under 35 U.S.C. §119(e) to application Ser. No. 60/953,745, filed Aug. 3, 2007 and 61/123,623, filed Apr. 9, 2008, the contents of which are incorporated herein by reference.

2. STATEMENT REGARDING FEDERALLY SPONSORED RESEARCH

Not applicable.

3. BACKGROUND

TWEAK receptor (TweakR), also known as Fn14 or TNFRSF12A, is a member of the tumor necrosis factor receptor superfamily. It is expressed on the surface of cancer cells derived from a variety of solid tumors. Expression of TweakR can be detected on some normal tissues, including the kidney (Bowman's capsule), liver (hepatocytes), and on proliferating endothelial cells and fibroblasts (Meighan-Mantha, et al., 1999, J. Biol. Chem. 1999; 274:33166-33176; and Jakubowski, et al., 2002, J. Cell Sci. 2002; 115:267-274). Expression of TweakR is up-regulated by growth factors in vitro and in vivo in response to tissue injury, regeneration, and inflammation (Feng, et al., 2000, Am. J. Pathol., 156:1253-1261; Wiley, et al., 2001, Immunity, 15:837-846; and Desplat-Jego, et al., 2005, J. Neuroimm., 133:116-123).

DNA and amino acid sequences corresponding to the TweakR have been reported (see, e.g., U.S. Pat. No. 6,531,447, U.S. Pat. No. 6,824,773, U.S. Patent Application Publication No. 2006/0025574, PCT Publication No. WO 98/55508, PCT Publication No. WO 99/61471). Similarly, methods of making and using TweakR antagonists and agonists to modulate angiogenesis associated with immunological disorders and cancer have been reported (see, e.g., U.S. Pat. No. 6,727,225, U.S. Pat. No. 6,824,773, U.S. Pat. No. 7,001,992, U.S. Pat. No. 7,169,387, U.S. Pat. No. 7,208,151, U.S. Patent Application Publication No. 2005/0054047, U.S. Patent Application Publication No. 2005/0208046, U.S. Patent Application Publication No. 2006/0084143, PCT Publication No. WO 00/42073). However, none of these reports have identified monoclonal antibodies that bind to TweakR and exhibit anti-tumor effects. These deficiencies have been addressed, as described herein, by the identification of antibodies that bind to TweakR and characterization of their biological activities. The identification of anti-TweakR monoclonal antibodies has led to the development of compositions for the treatment of solid tumors, and also provides screening tools for diagnostic use.

4. SUMMARY

Provided herein are compositions comprising monoclonal and humanized antibodies or antigen binding fragments thereof that bind human TweakR, and methods for their use in therapy, such as in treating cancer.

The anti-TweakR monoclonal or humanized antibodies can be generated from nucleic acids encoding polypeptides of monoclonal or humanized anti-TweakR antibodies, having 65%, 75%, 85%, 90%, 95%, 97% or 99% or more sequence identity to one or more of the amino acid sequences selected from the group consisting of SEQ ID NOs: 3-12. In other embodiments, the nucleic acid encodes a polypeptide of a monoclonal or humanized anti-TweakR antibody comprising an amino acid sequence selected from the group consisting of SEQ ID NOs: 3-12.

In other embodiments, anti-TweakR monoclonal or humanized antibodies can be derived from polypeptides having 65%, 75%, 85%, 90%, 95%, 97% or 99% or more sequence identity to one or more of the amino acid sequences selected from the group consisting of SEQ ID NOs: 3-12. In some embodiments, the polypeptide comprises one or more of the amino acid sequences selected from the group consisting of SEQ ID NOs: 3-12.

In some embodiments, the compositions comprise anti-TweakR mouse monoclonal antibodies or antibody fragments thereof, wherein said antibody comprises a mature heavy chain variable region comprising an amino acid sequence selected from the group consisting of SEQ ID NOs: 5, 7, or 9 and a mature light chain variable region comprising an amino acid sequence selected from the group consisting of SEQ ID NOs: 6, 8 or 10.

In some embodiments, the compositions comprise anti-TweakR humanized antibodies or antibody fragments thereof, wherein said antibody comprises a mature heavy chain variable region comprising an amino acid sequence selected from the group consisting of SEQ ID NOs: 3 and 11 and a mature light chain variable region comprising an amino acid sequence selected from the group consisting of SEQ ID NOs: 4 and 12.

In some embodiments, the compositions comprise anti-TweakR monoclonal or humanized antibodies or antibody fragments thereof, wherein said antibody comprises a heavy chain complementarity determining region comprising an amino acid sequence selected from the group consisting of SEQ ID NOs: 13-30 and 120-122 and a light chain complementarity region comprising an amino acid sequence selected from the group consisting of SEQ ID NOs: 66-83 and 127-129. Additionally, the compositions can comprise a heavy chain framework region comprising an amino acid sequence selected from the group consisting of SEQ ID NOs: 31-65 and 123-126 and/or a light chain framework region comprising an amino acid sequence selected from the group consisting of SEQ ID NOs. 84-119 and 130-133. The antibodies can comprise all of the complementarity determining regions of the heavy and/or light chain variable domain of an anti-TweakR antibody disclosed herein, optionally, wherein one or more of the framework regions surrounding the complementarity determining regions are also present. In some embodiments, the complementarity determining regions of both heavy and light chain variable regions are present.

In some embodiments, the antibody or antigen binding fragment binds to a human TweakR epitope recognized by the anti-TweakR humanized antibody, PDL192, wherein the epitope comprises an R at position 56 of SEQ ID NO: 2. PDL192 and other antibodies that are capable of binding a TweakR epitope comprising an R at position 56 are capable of killing TweakR expressing cells.

Although anti-TweakR antibodies have been described, the anti-TweakR antibodies described herein have a number of useful characteristics, including triggering apoptosis and/or stimulating antibody-mediated cellular cytotoxicity (ADCC) in cells expressing TweakR. TweakR expressing cells include cancer cells from, bladder cancer, breast cancer, colorectal cancer, lung cancer, melanoma, pancreatic cancer, head and neck cancer, ovarian cancer, stomach cancer, uterine cancer, cervical cancer, esophageal cancer, renal cell carcinoma, glioblastoma, and sarcomas.

Accordingly, the compositions described herein can be used to inhibit the proliferation and/or kill cells expressing TweakR. For example, in some embodiments, the compositions described herein can be used to treat an individual suffering from cancer, including, but not limited to, bladder cancer, breast cancer, colorectal cancer, lung cancer, melanoma, pancreatic cancer, ovarian cancer, renal cancer, head and neck cancer, esophageal cancer, uterine cancer, stomach cancer, cervical cancer, glioblastoma, and sarcomas.

The skilled person will appreciate that one or more specific features of any embodiment described herein can be combined with one or more features of any other embodiment described herein.

5. BRIEF DESCRIPTION OF THE FIGURES

FIG. 1A provides the nucleic acid (SEQ ID NO: 1) and FIG. 1B provides the amino acid sequence of TweakR (SEQ ID NO: 2);

FIG. 2A provides the amino acid sequence of the heavy chain variable region (SEQ ID NO: 3) and light chain variable region (SEQ ID NO: 4) of the humanized anti-TweakR antibody, PDL192;

FIG. 2B provides the amino acid sequence of the heavy chain variable region (SEQ ID NO: 5) and light chain variable region (SEQ ID NO: 6) of the murine anti-TweakR antibody 19.2.1;

FIG. 2C provides the amino acid sequence of the heavy chain variable region (SEQ ID NO: 7) and light chain variable region (SEQ ID NO: 8) of the murine anti-TweakR antibody 18.3.3;

FIG. 2D provides the amino acid sequence of the heavy chain variable region (SEQ ID NO: 9) and light chain variable region (SEQ ID NO: 10) of the murine anti-TweakR antibody 136.1;

FIG. 2E provides the amino acid sequence of the heavy chain variable region (SEQ ID NO: 11) and light chain variable region (SEQ ID NO: 12) of the humanized anti-TweakR antibody, PDL400;

FIG. 3A provides the amino acid sequences of the heavy chain complementarity determining region 1 (CDR1) for the humanized anti-TweakR antibody, PDL192 (SEQ ID NO: 13), murine anti-TweakR antibody, 19.2.1 (SEQ ID NO: 14), murine anti-TweakR antibody, 136.1 (SEQ ID NO: 15), murine anti-TweakR antibody, 18.3.3 (SEQ ID NO: 16), murine anti-TweakR antibody, ITEM-3 (SEQ ID NO: 17), and murine anti-TweakR antibody, ITEM-1 (SEQ ID NO: 18);

FIG. 3B provides the amino acid sequences of the heavy chain CDR2 for the humanized anti-TweakR antibody, PDL192 (SEQ ID NO: 19), murine anti-TweakR antibody, 19.2.1 (SEQ ID NO: 20), murine anti-TweakR antibody, 136.1 (SEQ ID NO: 21), murine anti-TweakR antibody, 18.3.3 (SEQ ID NO: 22), murine anti-TweakR antibody, ITEM-3 (SEQ ID NO: 23), and murine anti-TweakR antibody, ITEM-1 (SEQ ID NO: 24);

FIG. 3C provides the amino acid sequences of the heavy chain CDR3 for the humanized anti-TweakR antibody, PDL192 (SEQ ID NO: 25), murine anti-TweakR antibody, 19.2.1 (SEQ ID NO: 26), murine anti-TweakR antibody, 136.1 (SEQ ID NO: 27), murine anti-TweakR antibody, 18.3.3 (SEQ ID NO: 28), murine anti-TweakR antibody, ITEM-3 (SEQ ID NO: 29), and murine anti-TweakR antibody, ITEM-1 (SEQ ID NO: 30);

FIG. 3D provides the amino acid sequences of the heavy chain framework region 1 (FR1) for the humanized anti-TweakR antibody, PDL192 (SEQ ID NO: 31), humanized anti-TweakR antibody, PDL192-2 (SEQ ID NO: 32), murine anti-TweakR antibody, 19.2.1 (SEQ ID NO: 33), murine anti-TweakR antibody, 136.1 (SEQ ID NO: 34), murine anti-TweakR antibody, 18.3.3 (SEQ ID NO: 35), humanized anti-TweakR antibody, PDL183 (SEQ ID NO: 36), humanized anti-TweakR antibody, PDL183-2 (SEQ ID NO: 37), murine anti-TweakR antibody, ITEM-3 (SEQ ID NO: 38), and murine anti-TweakR antibody, ITEM-1 (SEQ ID NO: 39);

FIG. 3E provides the amino acid sequences of the heavy chain FR2 for the humanized anti-TweakR antibody, PDL192 (SEQ ID NO: 40), humanized anti-TweakR antibody, PDL192-2 (SEQ ID NO: 41), murine anti-TweakR antibody, 19.2.1 (SEQ ID NO: 42), murine anti-TweakR antibody, 136.1 (SEQ ID NO: 43), murine anti-TweakR antibody, 18.3.3 (SEQ ID NO: 44), humanized anti-TweakR antibody, PDL183 (SEQ ID NO: 45), humanized anti-TweakR antibody, PDL183-2 (SEQ ID NO: 46), murine anti-TweakR antibody, ITEM-3 (SEQ ID NO: 47), and murine anti-TweakR antibody, ITEM-1 (SEQ ID NO: 48);

FIG. 3F provides the amino acid sequences of the heavy chain FR3 for the humanized anti-TweakR antibody, PDL192 (SEQ ID NO: 49), humanized anti-TweakR antibody, PDL192-2 (SEQ ID NO: 50), murine anti-TweakR antibody, 19.2.1 (SEQ ID NO: 51), murine anti-TweakR antibody, 136.1 (SEQ ID NO: 52), murine anti-TweakR antibody, 18.3.3 (SEQ ID NO: 53), humanized anti-TweakR antibody, PDL183 (SEQ ID NO: 54), humanized anti-TweakR antibody, PDL183-2 (SEQ ID NO: 55), murine anti-TweakR antibody, ITEM-3 (SEQ ID NO: 56), and murine anti-TweakR antibody, ITEM-1 (SEQ ID NO: 57);

FIG. 3G provides the amino acid sequences of the heavy chain FR4 for the humanized anti-TweakR antibody, PDL192 (SEQ ID NO: 58), murine anti-TweakR antibody, 19.2.1 (SEQ ID NO: 59), murine anti-TweakR antibody, 136.1 (SEQ ID NO: 60), murine anti-TweakR antibody, 18.3.3 (SEQ ID NO: 61), humanized anti-TweakR antibody, PDL183 (SEQ ID NO: 62), humanized anti-TweakR antibody, PDL183-2 (SEQ ID NO: 63), murine anti-TweakR antibody, ITEM-3 (SEQ ID NO: 64), and murine anti-TweakR antibody, ITEM-1 (SEQ ID NO: 65);

FIG. 4A provides the amino acid sequences of the light chain CDR1 for the humanized anti-TweakR antibody, PDL192 (SEQ ID NO: 66), murine anti-TweakR antibody, 19.2.1 (SEQ ID NO: 67), murine anti-TweakR antibody, 136.1 (SEQ ID NO: 68), murine anti-TweakR antibody, 18.3.3 (SEQ ID NO: 69), murine anti-TweakR antibody, ITEM-3 (SEQ ID NO: 70), and murine anti-TweakR antibody, ITEM-1 (SEQ ID NO: 71);

FIG. 4B provides the amino acid sequences of the light chain CDR2 for the humanized anti-TweakR antibody, PDL192 (SEQ ID NO: 72), murine anti-TweakR antibody, 19.2.1 (SEQ ID NO: 73), murine anti-TweakR antibody, 136.1 (SEQ ID NO: 74), murine anti-TweakR antibody, 18.3.3 (SEQ ID NO: 75), murine anti-TweakR antibody, ITEM-3 (SEQ ID NO: 76), and murine anti-TweakR antibody, ITEM-1 (SEQ ID NO: 77);

FIG. 4C provides the amino acid sequences of the light chain CDR3 for the humanized anti-TweakR antibody, PDL192 (SEQ ID NO: 78), murine anti-TweakR antibody, 19.2.1 (SEQ ID NO: 79), murine anti-TweakR antibody, 136.1 (SEQ ID NO: 80), murine anti-TweakR antibody, 18.3.3 (SEQ ID NO: 81), murine anti-TweakR antibody, ITEM-3 (SEQ ID NO: 82), and murine anti-TweakR antibody, ITEM-1 (SEQ ID NO: 83);

FIG. 4D provides the amino acid sequences of the light chain FR1 for the humanized anti-TweakR antibody, PDL192 (SEQ ID NO: 84), humanized anti-TweakR antibody, PDL192-2 (SEQ ID NO: 85), murine anti-TweakR antibody, 19.2.1 (SEQ ID NO: 86), murine anti-TweakR antibody, 136.1 (SEQ ID NO: 87), murine anti-TweakR antibody, 18.3.3 (SEQ ID NO: 88), humanized anti-TweakR antibody, PDL183 (SEQ ID NO: 89), humanized anti-TweakR antibody, PDL183-2 (SEQ ID NO: 90), murine anti-TweakR antibody, ITEM-3 (SEQ ID NO: 91), and murine anti-TweakR antibody, ITEM-1 (SEQ ID NO: 92);

FIG. 4E provides the amino acid sequences of the light chain FR2 for the humanized anti-TweakR antibody, PDL192 (SEQ ID NO: 93), humanized anti-TweakR antibody, PDL192-2 (SEQ ID NO: 94), murine anti-TweakR antibody, 19.2.1 (SEQ ID NO: 95), murine anti-TweakR antibody, 136.1 (SEQ ID NO: 96), murine anti-TweakR antibody, 18.3.3 (SEQ ID NO: 97), humanized anti-TweakR antibody, PDL183 (SEQ ID NO: 98), humanized anti-TweakR antibody, PDL183-2 (SEQ ID NO: 99), murine anti-TweakR antibody, ITEM-3 (SEQ ID NO: 100), and murine anti-TweakR antibody, ITEM-1 (SEQ ID NO: 101);

FIG. 4F provides the amino acid sequences of the light chain FR3 for the humanized anti-TweakR antibody, PDL192 (SEQ ID NO: 102), humanized anti-TweakR antibody, PDL192-2 (SEQ ID NO: 103), murine anti-TweakR antibody, 19.2.1 (SEQ ID NO: 104), murine anti-TweakR antibody, 136.1 (SEQ ID NO: 105), murine anti-TweakR antibody, 18.3.3 (SEQ ID NO: 106), humanized anti-TweakR antibody, PDL183 (SEQ ID NO: 107), humanized anti-TweakR antibody, PDL183-2 (SEQ ID NO: 108), murine anti-TweakR antibody, ITEM-3 (SEQ ID NO: 109), and murine anti-TweakR antibody, ITEM-1 (SEQ ID NO: 110);

FIG. 4G provides the amino acid sequences of the light chain FR4 for the humanized anti-TweakR antibody, PDL192 (SEQ ID NO: 111), humanized anti-TweakR antibody, PDL192-2 (SEQ ID NO: 112), murine anti-TweakR antibody, 19.2.1 (SEQ ID NO: 113), murine anti-TweakR antibody, 136.1 (SEQ ID NO: 114), murine anti-TweakR antibody, 18.3.3 (SEQ ID NO: 115), humanized anti-TweakR antibody, PDL183 (SEQ ID NO: 116), humanized anti-TweakR antibody, PDL183-2 (SEQ ID NO: 117), murine anti-TweakR antibody, ITEM-3 (SEQ ID NO: 118), and murine anti-TweakR antibody, ITEM-1 (SEQ ID NO: 119);

FIG. 5 provides the CDR and FR consensus sequences for anti-TweakR antibodies;

FIG. 6 provides an exemplary gene expression profile of TweakR gene expression in a variety of solid tumors. The X-axis represents individual samples assessed on the gene chip, and the Y-axis indicates the average intensity of TweakR expression for each sample;

FIG. 7A-7D depicts an immunohistological staining of TweakR-expressing tumor cells with the anti-TweakR antibody 29.T10;

Figure 10A:
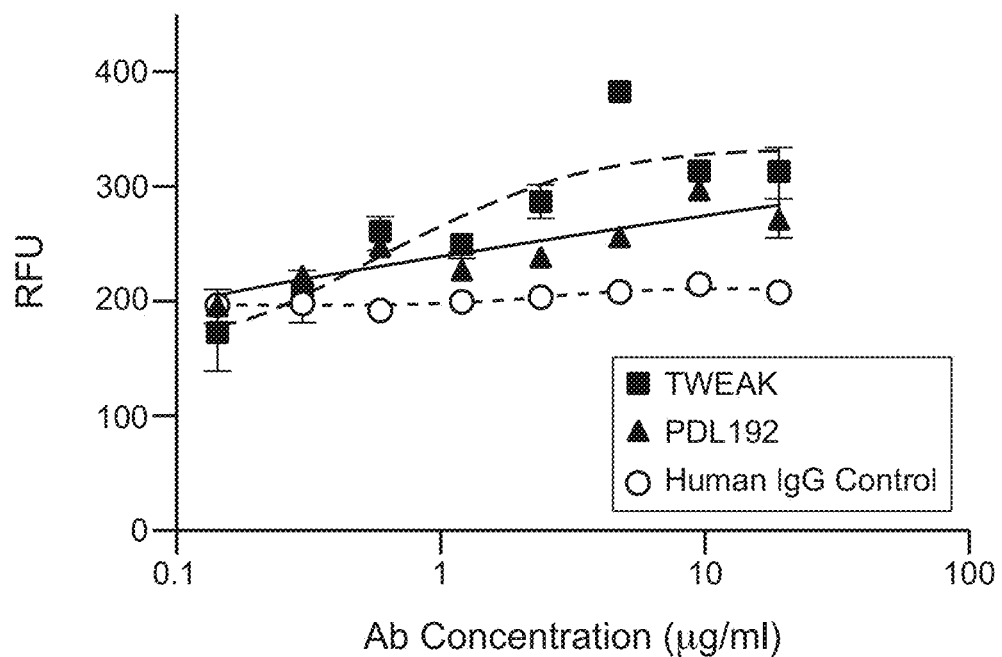
Figure 10B:
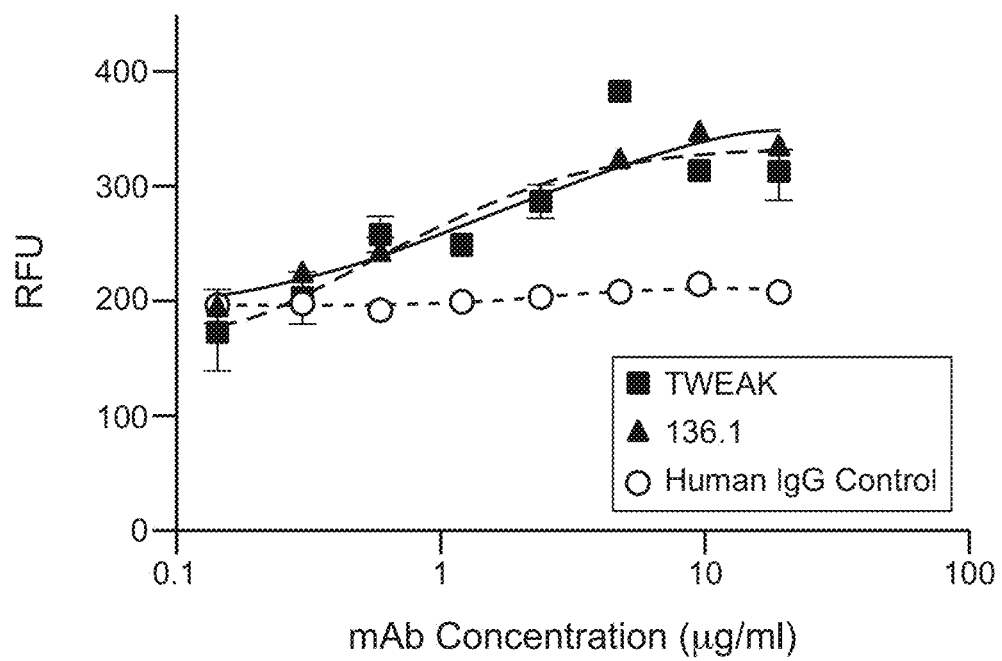
Figure 11:
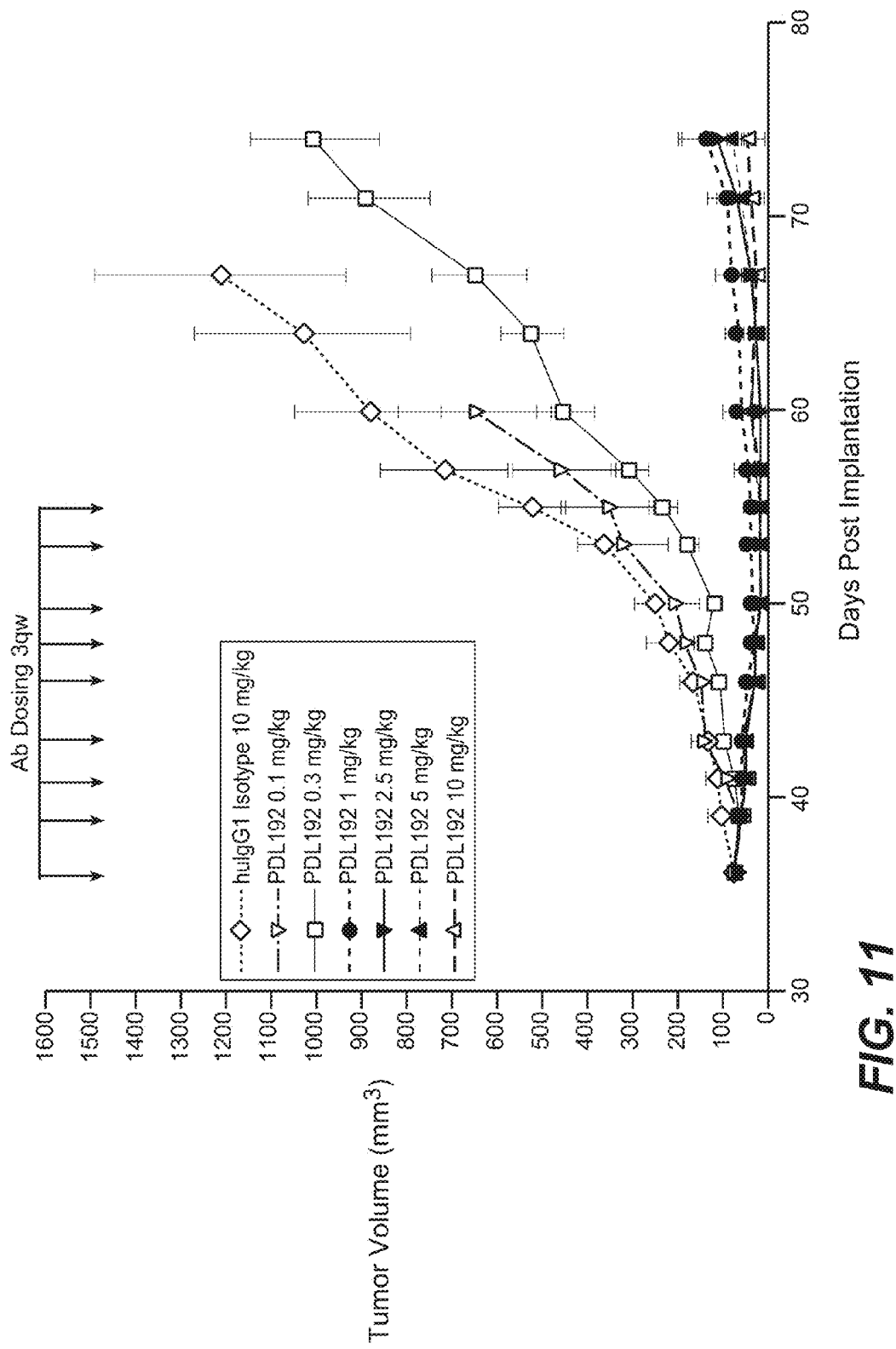
Figure 12:
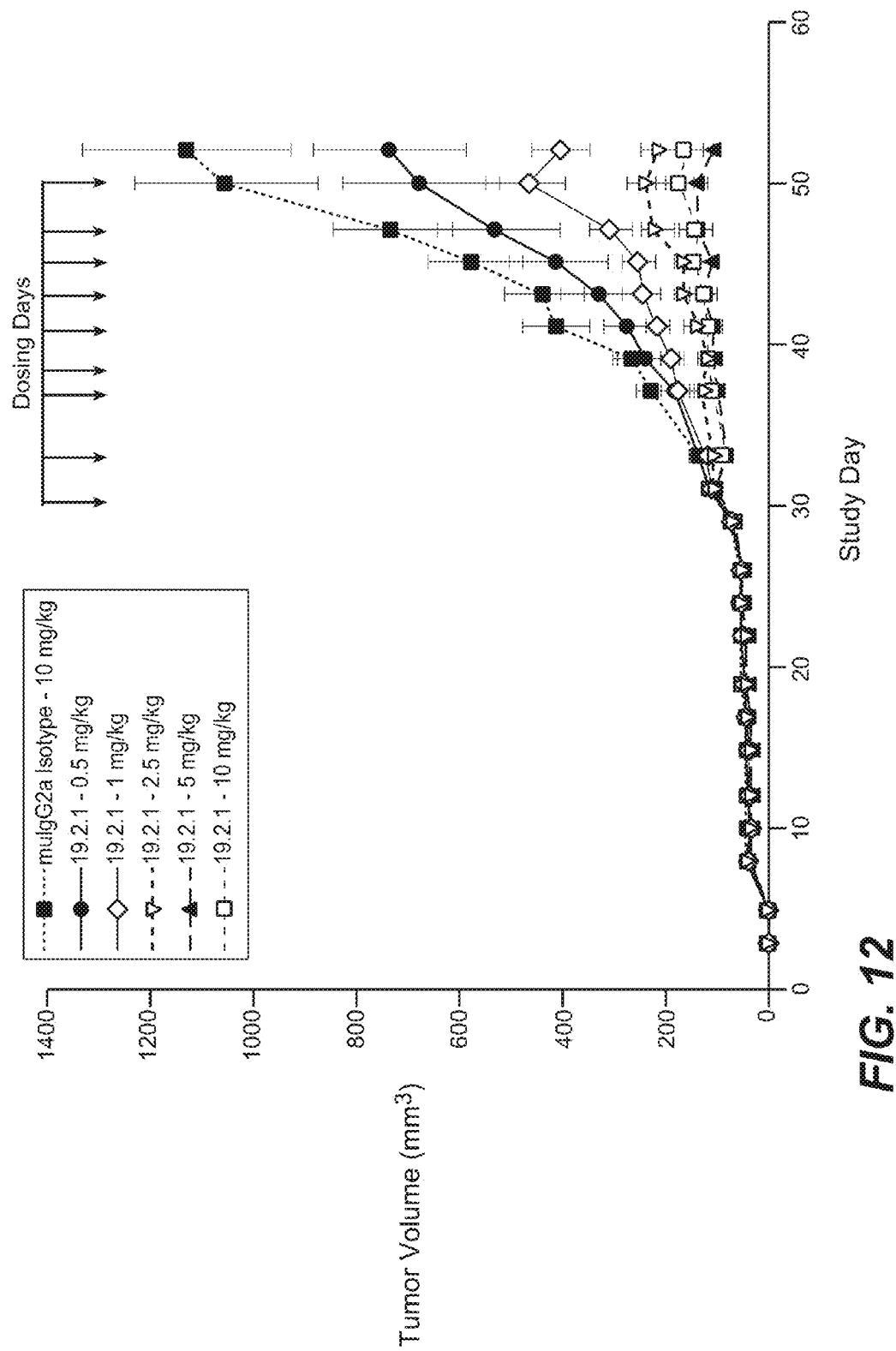
Figure 13:
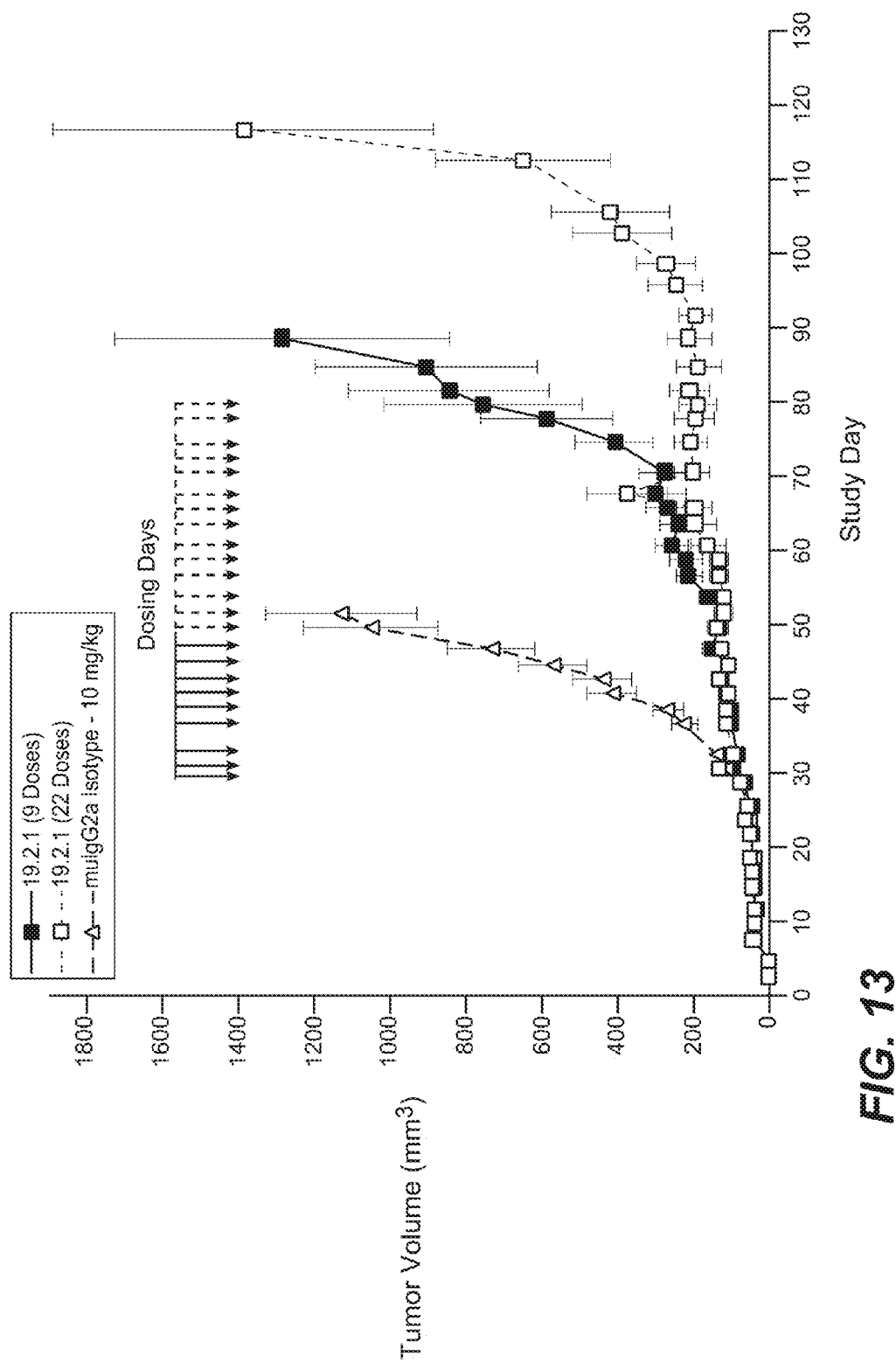
Figure 14:
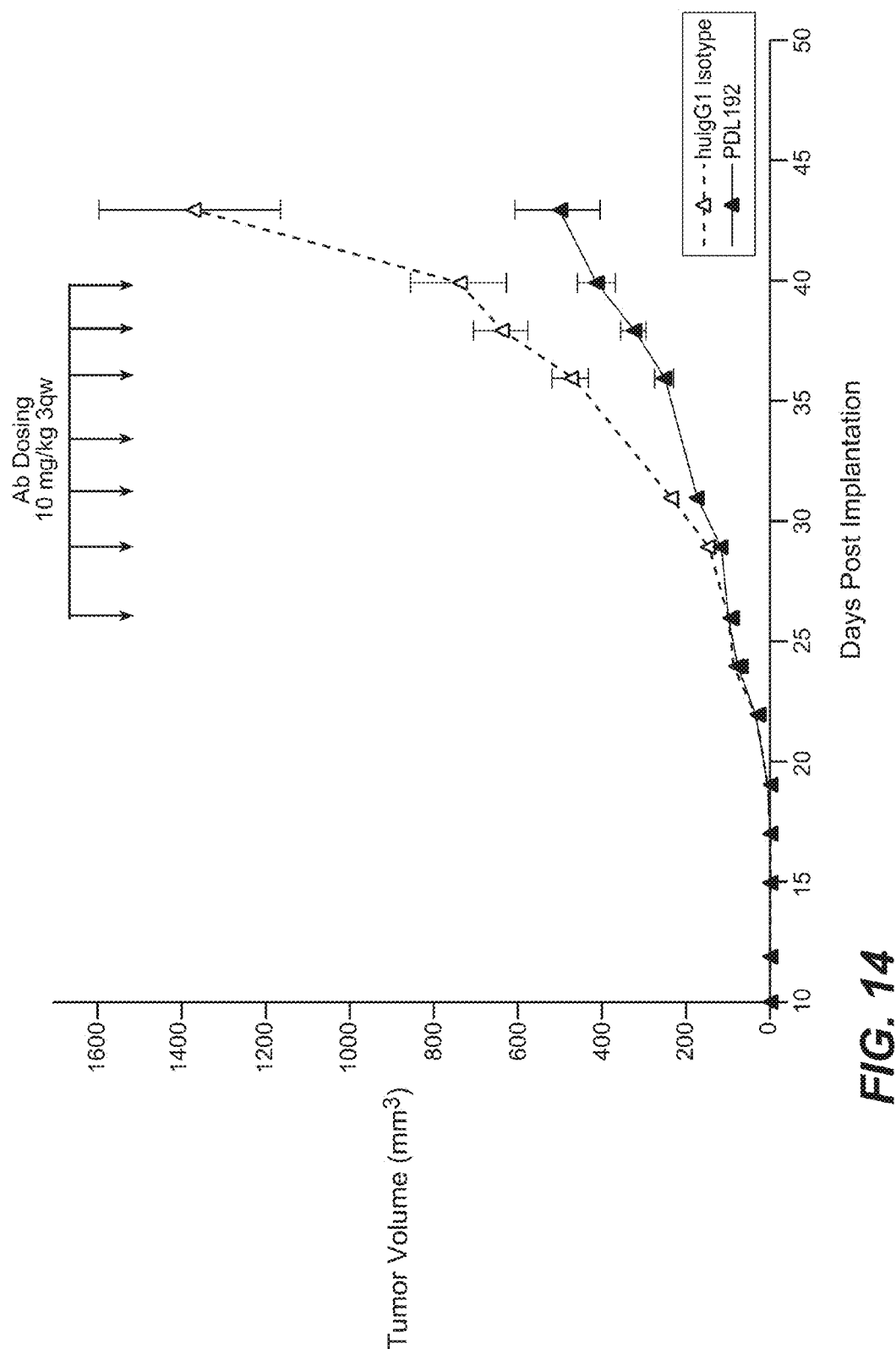
Figure 15:
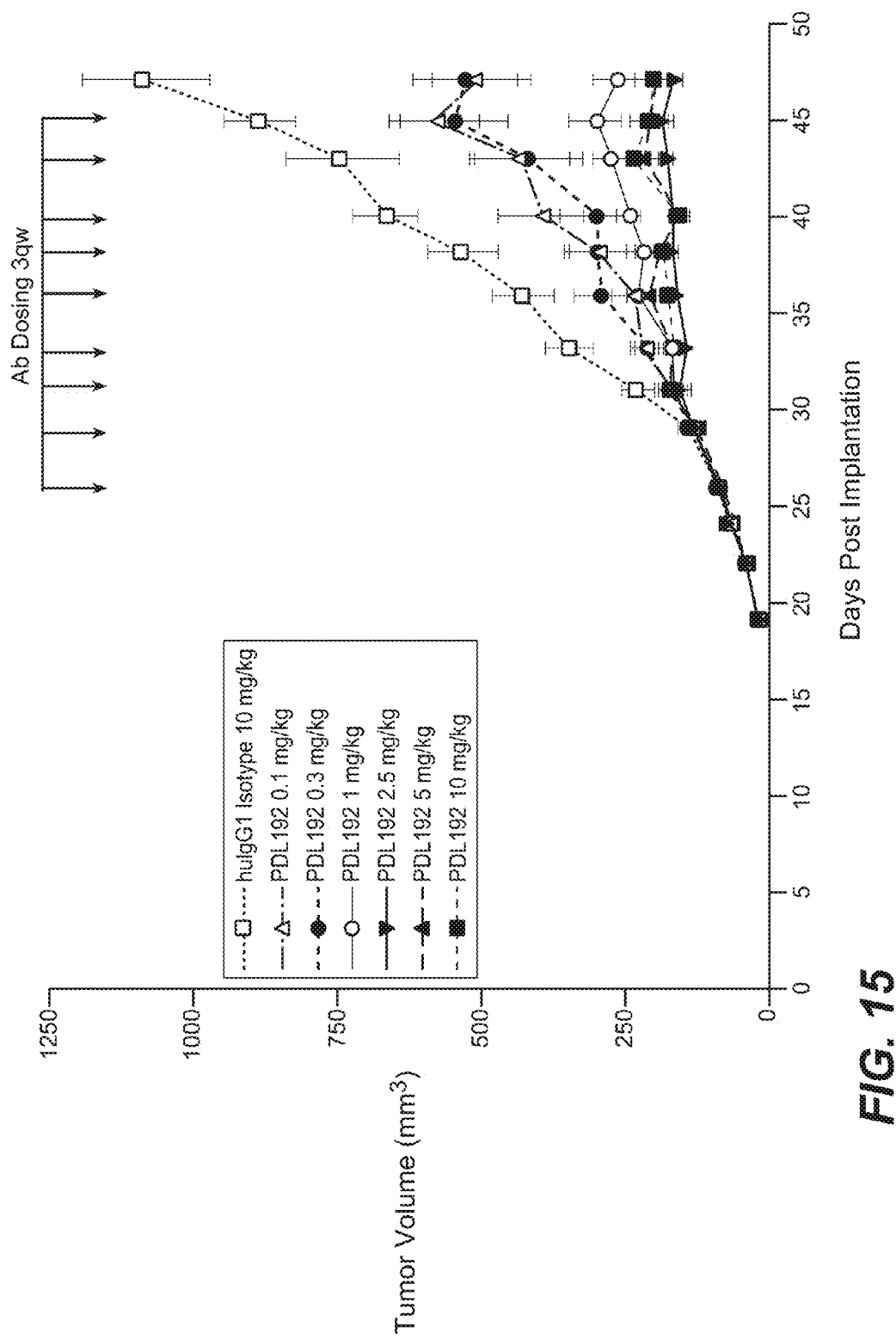
Figure 16:
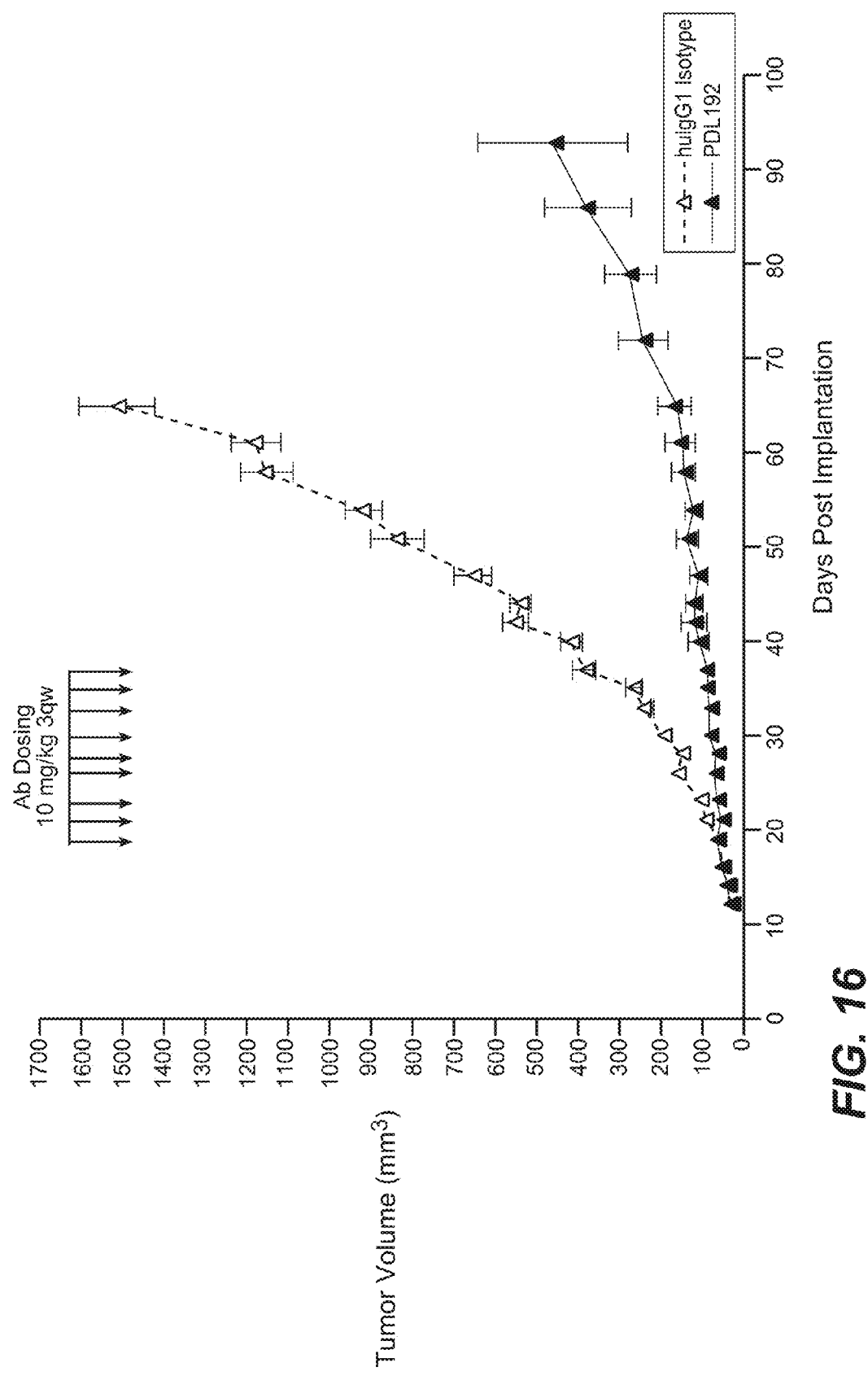
Figure 17:
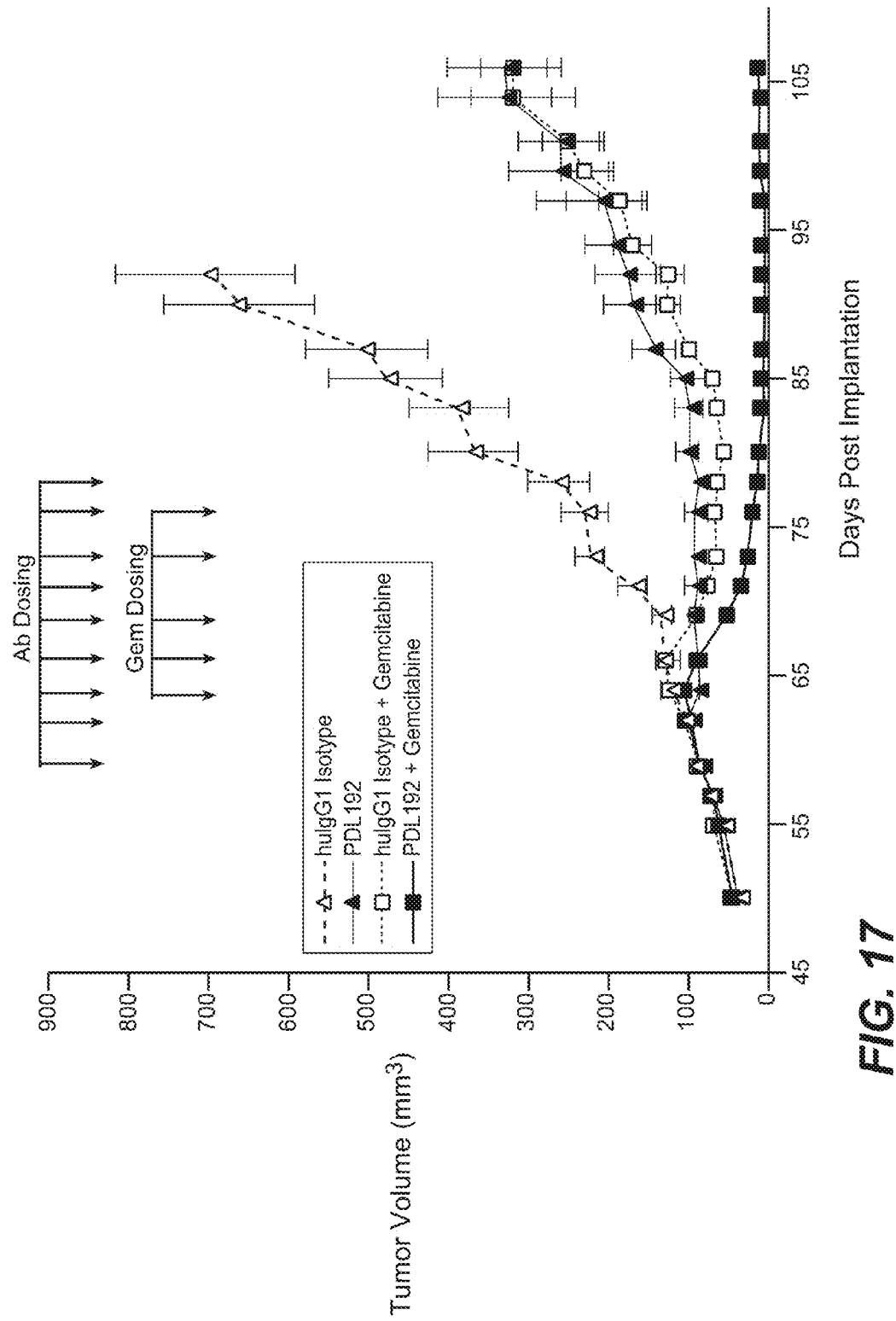
Figure 18A:
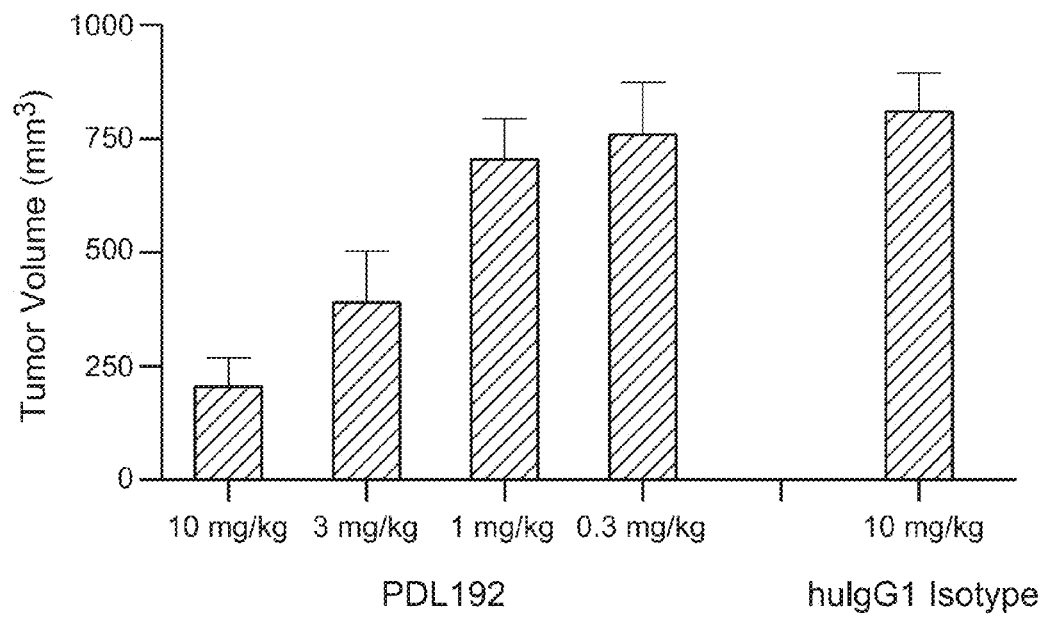
Figure 18B:
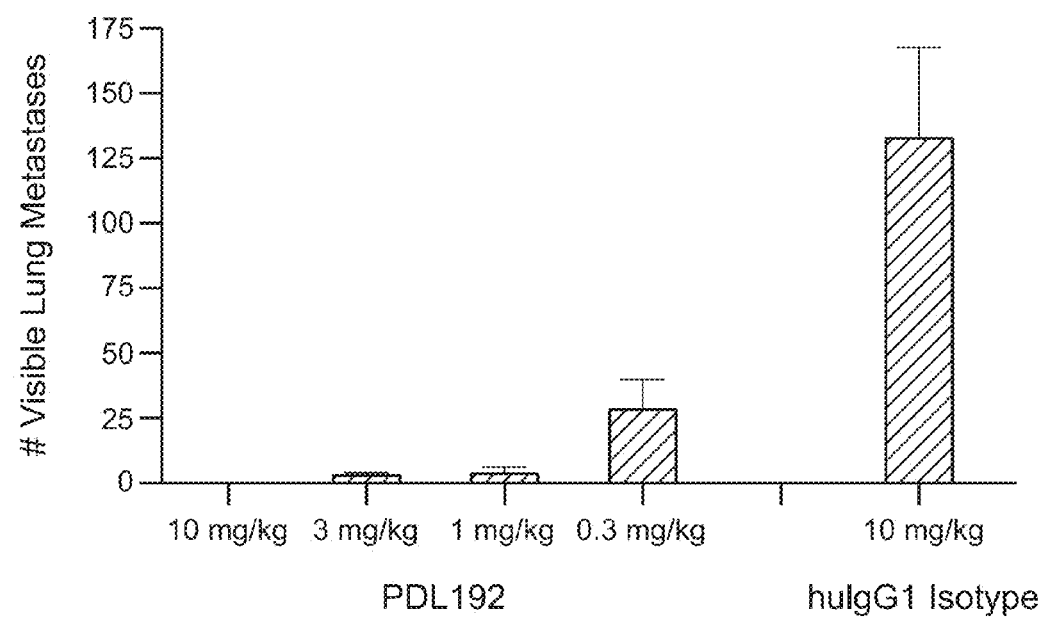
Figure 19A:
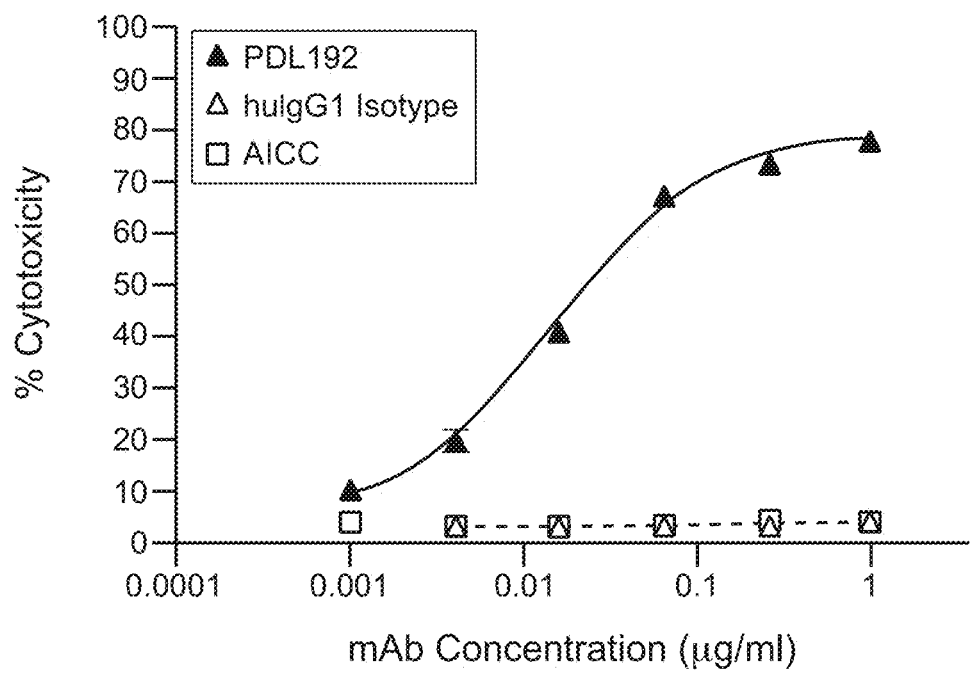
Figure 19B:
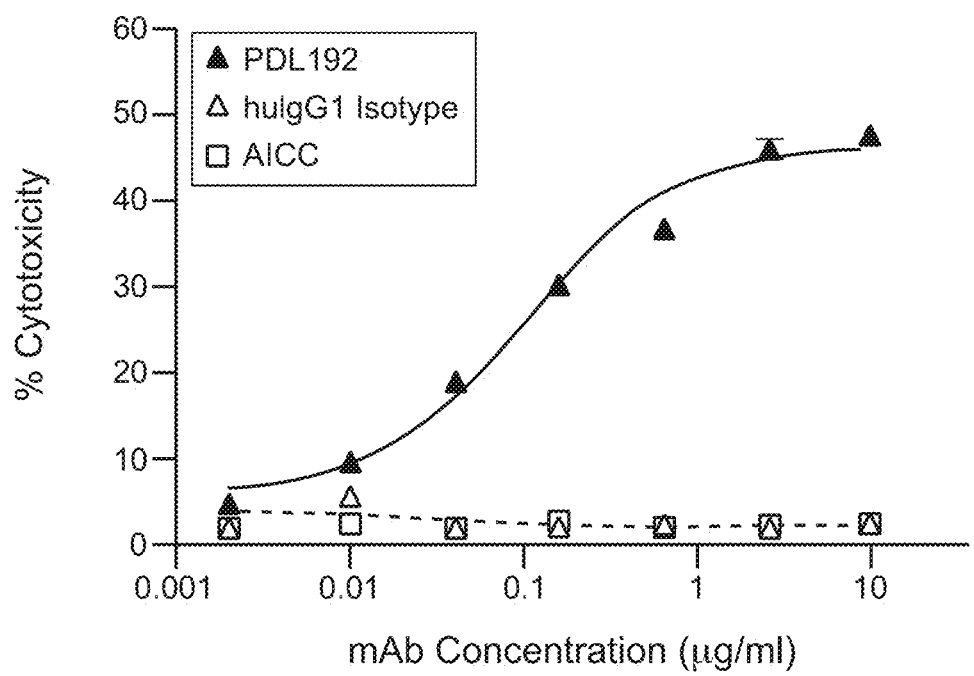
Figure 19C:
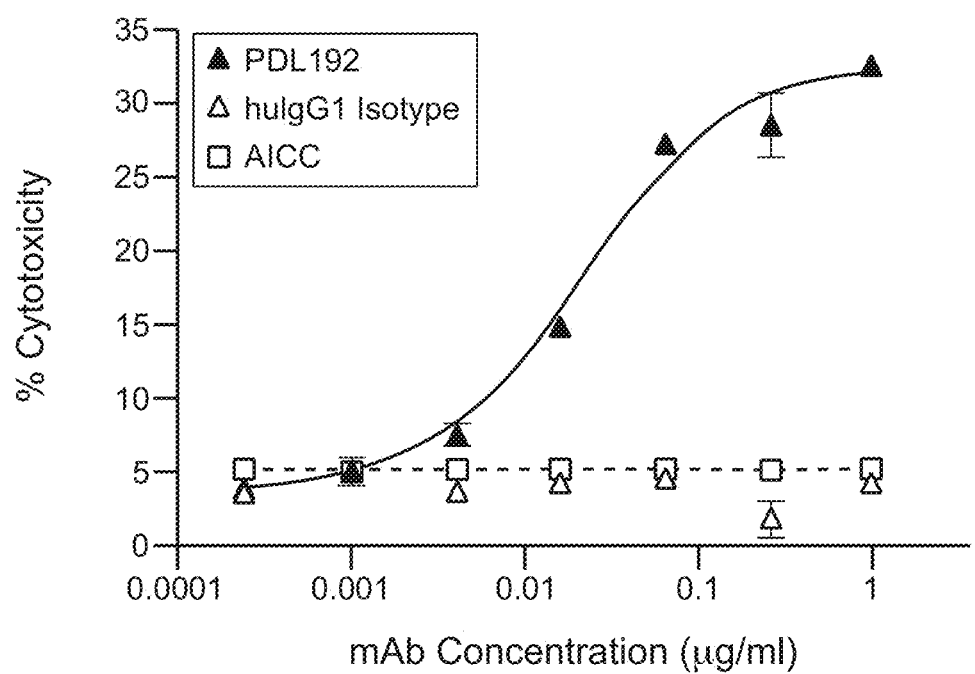
Figure 20A:
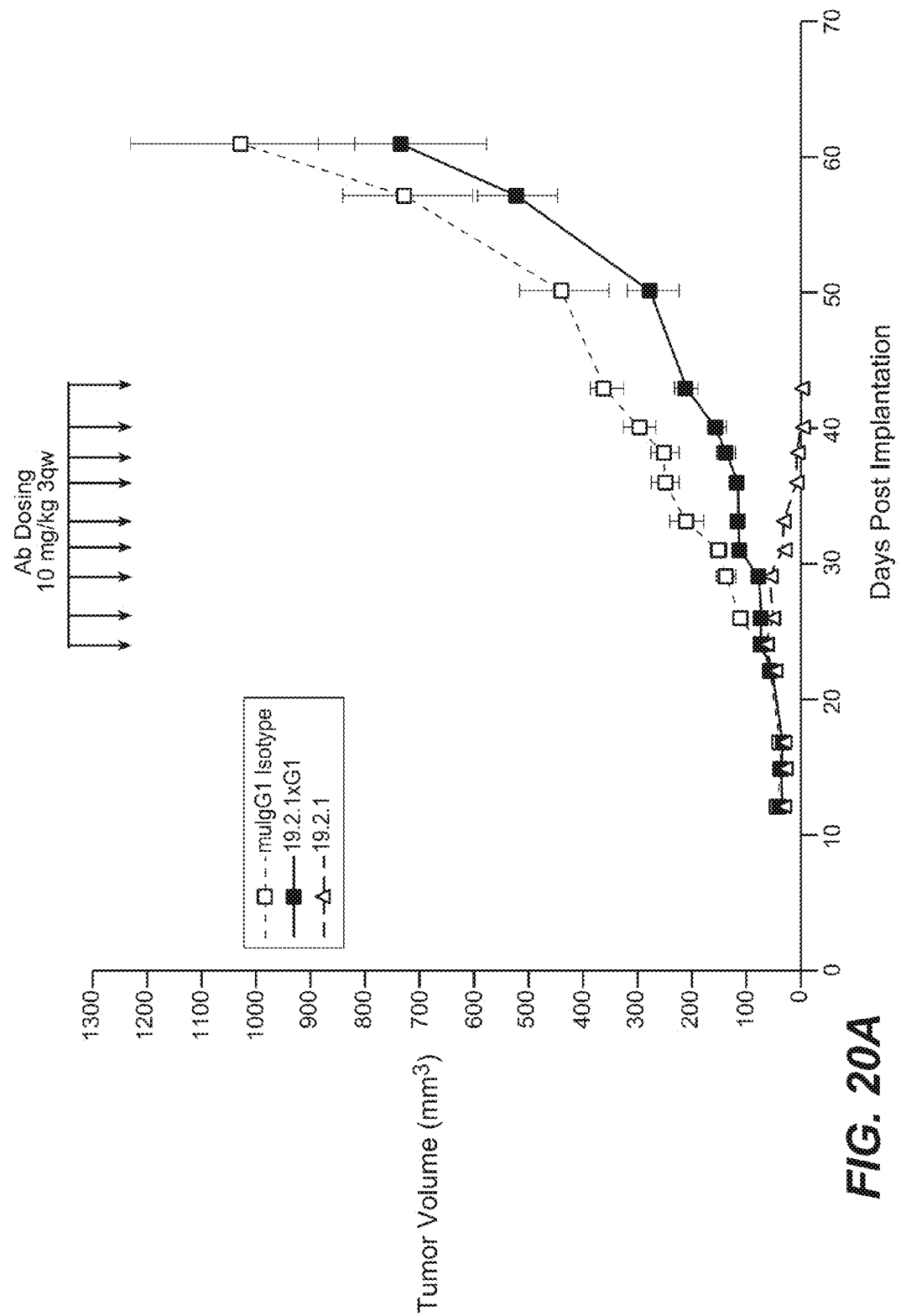
Figure 20B:
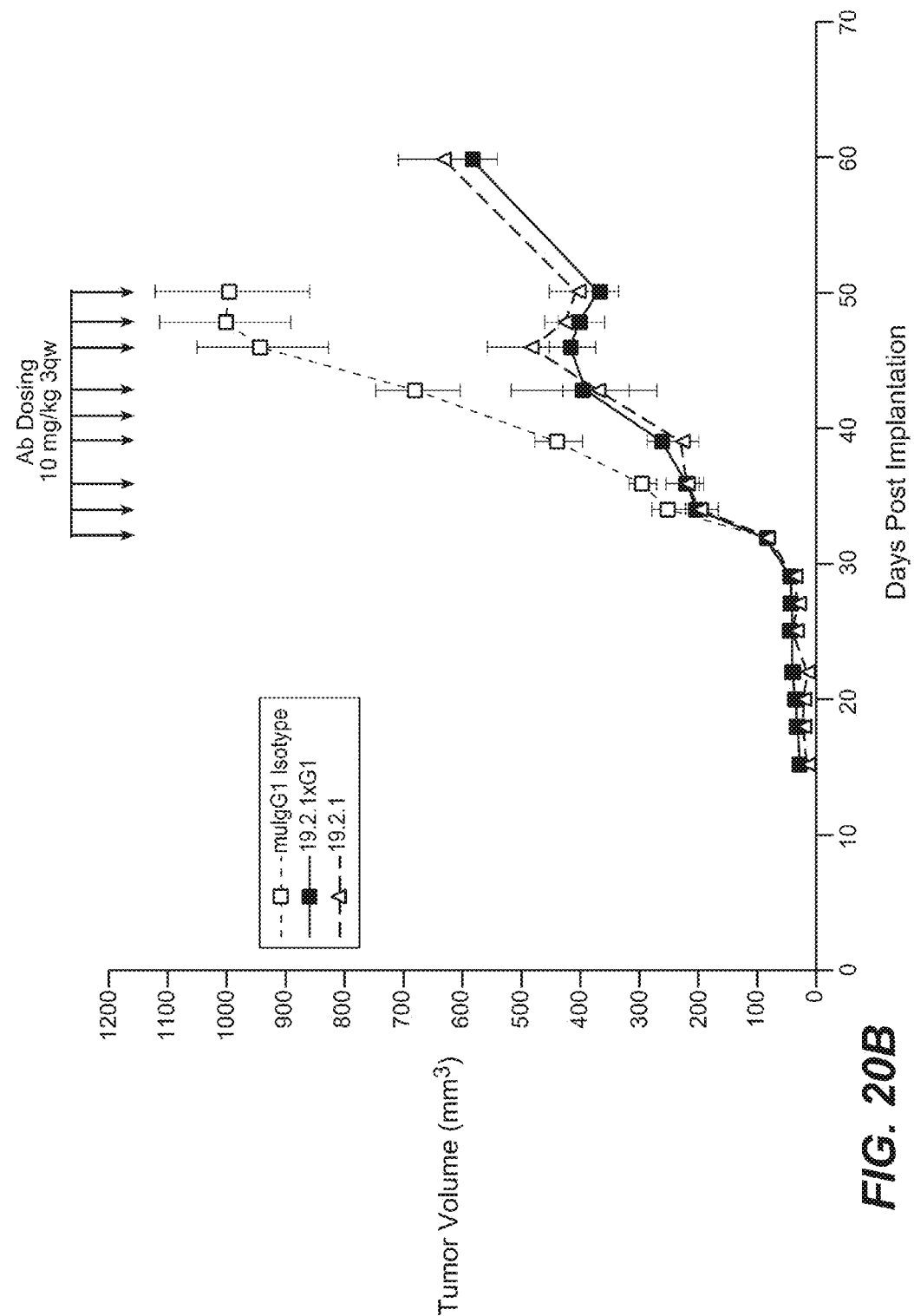

FIGS. 10A-10B provide exemplary examples by which the anti-TweakR antibodies PDL192 (FIG. 10A) and 136.1 (10B) inhibit cell growth by inducing apoptosis through caspase activation;

FIG. 11 depicts anti-tumor activity of PDL192 in the SN12C renal cell xenograft model;

FIG. 12 depicts a dose-range finding study with 19.2.1 in the A253 xenograft model of head and neck cancer;

FIG. 13 depicts anti-tumor activity using 19.2.1 in a chronic dosing regimen in the A253 model of head and neck cancer;

FIG. 14 depicts anti-tumor activity of PDL192 in the HT1376 urinary bladder xenograft model;

FIG. 15 depicts anti-tumor activity in a dose-range finding study with PDL192 in the A375 melanoma xenograft model;

FIG. 16 depicts the anti-tumor activity of PDL192 in the CSOC ovarian xenograft model;

FIG. 17 depicts the anti-tumor activity of PDL192± gemcitabine in the Panc1 xenograft model;

FIGS. 18A-18B depict the anti-tumor and anti-metastatic activity of PDL192 in a model of breast cancer using the MDA-MB-231 variant xenograft;

FIGS. 19A-19B depict the ADCC activity of the anti-TweakR antibody PDL192 on TweakR transfectants (FIG. 19A) and SN12C renal cancer cells (FIG. 19B) using human PBMCs as effector cells;

FIG. 19C depicts the ADCC activity of the anti-TweakR antibody PDL192 on TweakR transfectants using mouse splenocytes as effector cells; and FIGS. 20A-20B depict the anti-tumor activity of a murine IgG1 isotype (19.2.1×G1) and murine IgG2a isotype (19.2.1) in the SN12C renal xenograft model (FIG. 20A) and in the A375 xenograft melanoma xenograft model (FIG. 20B).

6. DETAILED DESCRIPTION

It is to be understood that both the foregoing general description and the following detailed description are exemplary and explanatory only and are not restrictive of the compositions and methods described herein. In this application, the use of the singular includes the plural unless specifically state otherwise. Also, the use of "or" means "and/or" unless state otherwise. Similarly, "comprise," "comprises," "comprising," "include," "includes" and "including" are not intended to be limiting.

6.2 Definitions

As used herein, the following terms are intended to have the following meanings:

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab').sub.2, Fab, Fv and rIgG). See also, Pierce Catalog and Handbook, 1994-1995 (Pierce Chemical Co., Rockford, Ill.). See also, e.g., Kuby, J., Immunology, 3.sup.rd Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow and Lane, "Antibodies: A Laboratory Manual," Cold Spring Harbor Laboratory Press, New York (1988); Hammerling et al., in: "Monoclonal Antibodies and T-Cell Hybridomas," Elsevier, N.Y. (1981), pp. 563 681 (both of which are incorporated herein by reference in their entireties).

An antibody immunologically reactive with a particular antigen can be generated by recombinant methods such as selection of libraries of recombinant antibodies in phage or similar vectors, see, e.g., Huse et al., Science 246:1275-1281 (1989); Ward et al., Nature 341:544-546 (1989); and Vaughan et al., Nature Biotech. 14:309-314 (1996), or by immunizing an animal with the antigen or with DNA encoding the antigen. Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well-known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Typically, an immunoglobulin has a heavy and light chain. Each heavy and light chain contains a constant region and a variable region, (the regions are also known as "domains"). Light and heavy chain variable regions contain four "framework" regions interrupted by three hypervariable regions, also called "complementarity-determining regions" or "CDRs". The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" refer to the variable region of an immunoglobulin heavy chain of an antibody, including the heavy chain of an Fv, scFv, or Fab. References to "$V_L$" refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Any of the anti-TweakR antibodies described herein can be chimeric.

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85%, at least 90%, and at least 95% identical. Hence, all parts of a humanized immunoglobulin, except possibly the CDRs, are substantially identical to corresponding parts of one or more native human immunoglobulin sequences. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. Nos. 5,530,101; 5,585,089; 5,693,761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519, 596; Padlan, Mol. Immunol., 28:489 498 (1991); Studnicka et al., Prot. Eng. 7:805 814 (1994); Roguska et al., Proc. Natl. Acad. Sci. 91:969 973 (1994), and chain shuffling (U.S. Pat. No. 5,565,332), all of which are hereby incorporated by reference in their entireties. The anti-TweakR antibodies described herein include humanized antibodies, such as mouse humanized antibodies, fully human antibodies, and mouse antibodies.

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The determination of whether two antibodies bind substantially to the same epitope is accomplished by the methods known in the art, such as a competition assay. In conducting an antibody competition study between a control antibody (for example, one of the anti-TweakR antibodies described herein) and any test antibody, one may first label the control antibody with a detectable label, such as, biotin, enzymatic, radioactive label, or fluorescent label to enable the subsequent identification. The intensity of the bound label is measured. If the labeled antibody competes with the unlabeled antibody by binding to an overlapping epitope, the intensity will be decreased relative to the binding by negative control unlabeled antibody.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. In some embodiments, it means that the nucleic acid or protein is at least 85% pure, at least 95% pure, and at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Conservative substitutions for one another typically include e.g.: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The radioisotope may be, for example, 3H, 14C, 32P, 35S, or 125I. In some embodiments, radioisotopes are used as toxic moieties.

The labels may be incorporated into the antibodies at any position. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982). The lifetime of radiolabeled peptides or radiolabeled antibody compositions can be extended by the addition of substances that stablize the radiolabeled peptide or antibody and protect it from degradation. Any substance or combination of substances that stablize the radiolabeled peptide or antibody may be used including those substances disclosed in U.S. Pat. No. 5,961,955.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background.

6.3 DETAILED DESCRIPTION

The compositions described herein are based upon the identification of monoclonal and humanized anti-TweakR antibodies capable of triggering apoptosis and/or stimulating ADCC in cells expressing TweakR. In particular, these antibodies find use in pharmaceutical compositions used to treat cancer.

6.4 TweakR ANTIBODIES

The anti-TweakR antibodies described herein specifically bind to TweakR proteins. By "specifically bind" herein is meant that the antibodies bind to the protein with a $K_D$ of at least about 1 µM, at least about 0.1 µM or better, at least about 0.01 µM, and at least about 0.001 µM or better. In some embodiments, the antibodies described herein are capable of selectively binding to the specific target and not to related sequences.

By "TweakR proteins", herein is meant that the anti-TweakR antibodies can bind a protein comprising an amino acid sequence encoded by SEQ ID NO: 1, or encoded by a nucleic acid sequence which can hybridize to SEQ ID NO: 1, or which comprises the amino acid sequence of SEQ ID NO: 2.

The anti-TweakR antibodies described herein are capable of modulating the activity of a TweakR or ligand gene. In general, the antibodies exhibit at least one of the properties associated with agonists and antagonists of TweakR. By "agonist" herein is meant an antibody that is capable of promoting one or more biological activities associated with TweakR. By "antagonistic" herein is meant an antibody that is capable of inhibiting one or more biological activities associated with TweakR and/or TweakR-ligand interaction. Biological properties associated with the TweakR, include, but are not limited to, pro-apoptosis, pro-proliferation, pro-migration and pro-inflammatory activity (see, e.g., Wiley, et al., 2001, Immunity, 15:837-846, Wiley and Winkles, 2003, Cytokine & Growth Factor Review, 14:241-249; and Winkles, et al., 2006, Cancer Letters, 235(1):11-7). Accordingly, the anti-TweakR antibodies described here can exhibit between 0% to 100% agonist activity. For example, in some embodiments, the anti-TweakR antibodies can exhibit at least about 0% agonist activity, at least about 10% agonist activity, at least about 20% agonist activity, at least about 30% agonist activity, at least about 40% agonist activity, at least about 50% agonist activity, at least about 60% agonist activity, at least about 70% agonist activity, at least about 80% agonist activity, at least about 90% agonist activity, at least about 100% agonist activity. In some embodiments, the anti-TweakR antibodies described herein can exhibit greater than 100% agonist activity.

Agonist/antagonist activity can be determined by measuring the release of cytokines and/or chemokines in an in vitro cell growth assay. For example, as set forth in the EXAMPLES, in a typical assay the cells are incubated in vitro with an anti-TweakR antibody±TWEAK ligand. Twenty four hours later, the cell supernatant is assessed for the presence of cytokines and/or chemokines using an ELISA assay or a commercial fluorescent bead-based multiplex assay (e.g., Luminex®, Upstate).

In some embodiments, an IL-8 release assay is used to characterize the agonist/antagonistic activity of the various anti-TweakR antibodies described herein (see e.g., FIGS. 8A-8E and Example 2). Using the data generated from an IL-8 assay, the percent agonist activity can be calculated using the formula: % agonist activity=(a−c)/(b−c). The percent antagonist activity can be calculated using the formula: % antagonist=(b−d)/(b−a); in which a=quantity of IL8 released from cells treated with antibody at 10 μg/ml, b=quantity of IL8 released from cells treated with TWEAK at 300 ng/ml, c=quantity of IL8 released from untreated cells, and d=quantity of IL8 released from cells treated with TWEAK at 300 ng/ml and antibody at 10 μg/ml.

Figure 8A:
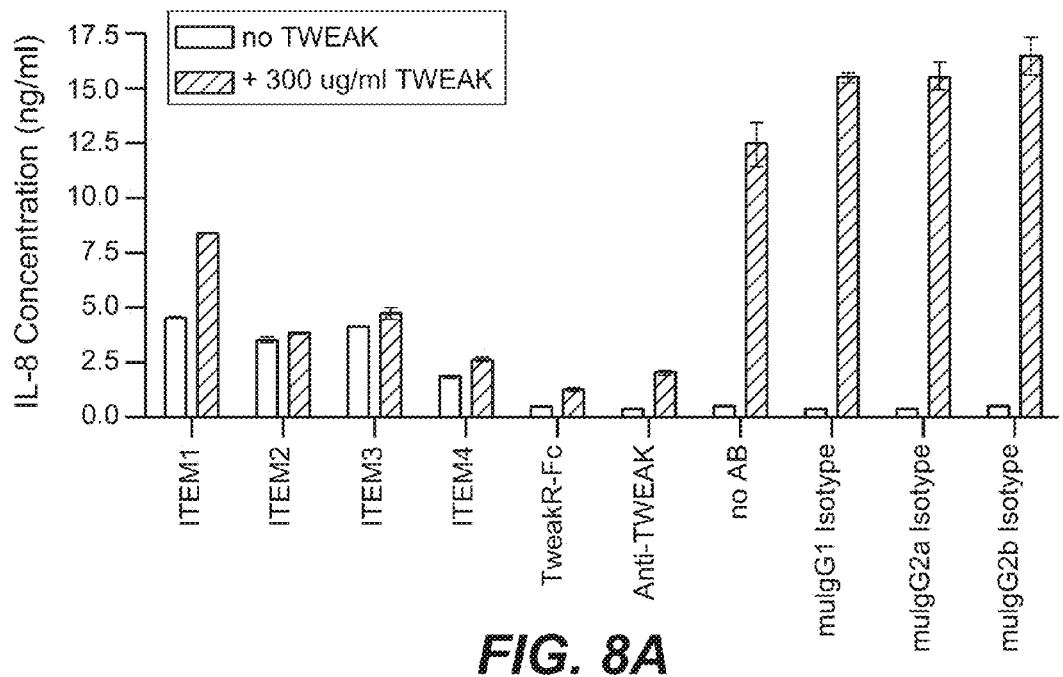
FIG. 8A depicts the release of IL-8 by the anti-Tweak R antibodies ITEM1, ITEM2, ITEM3, ITEM4 and isotype controls.
Figure 8B:
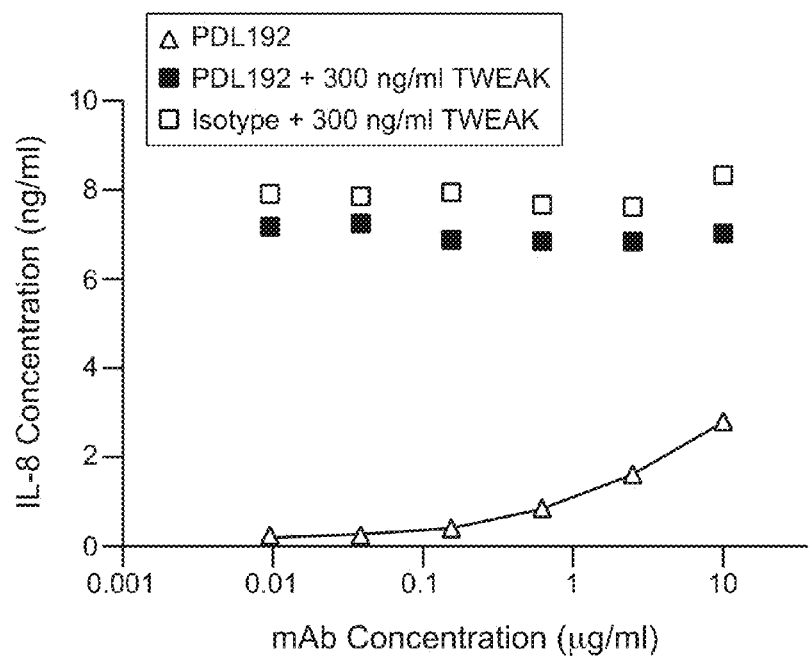
FIG. 8B depicts the release of IL-8 by the anti-Tweak R antibody PDL192.
Figure 8C:
FIG. 8C depicts the release of IL-8 by the anti-Tweak R antibody 18.3.3.
Figure 8D:
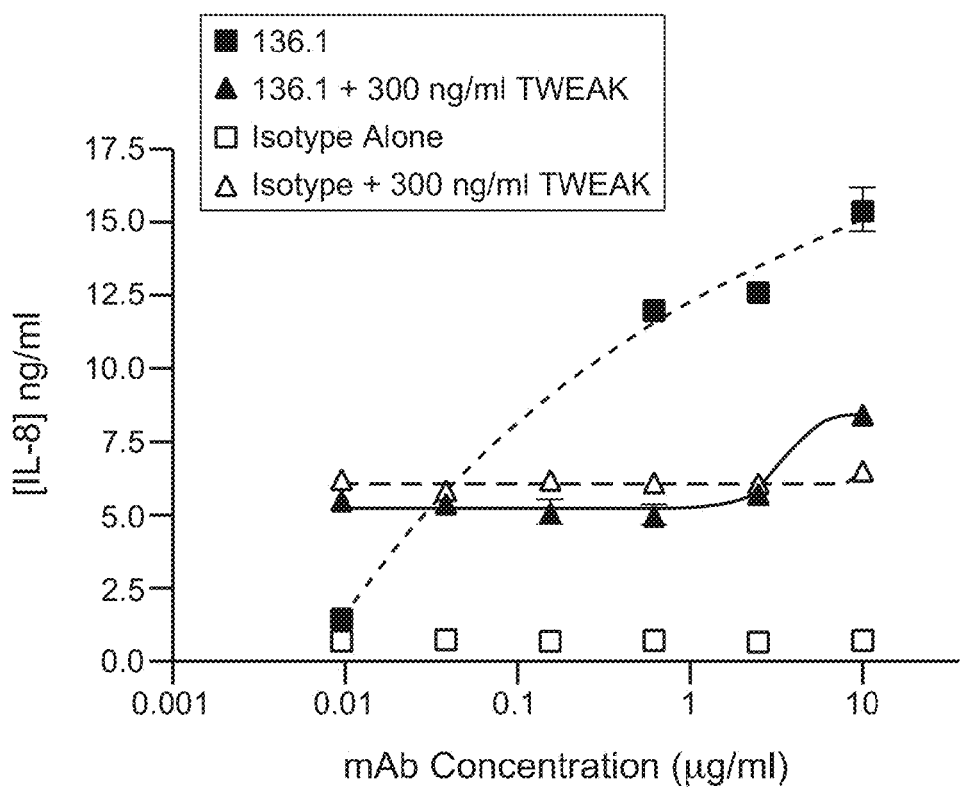
FIG. 8D depicts the release of IL-8 by the anti-Tweak R antibody 136.1.
Figure 8E:
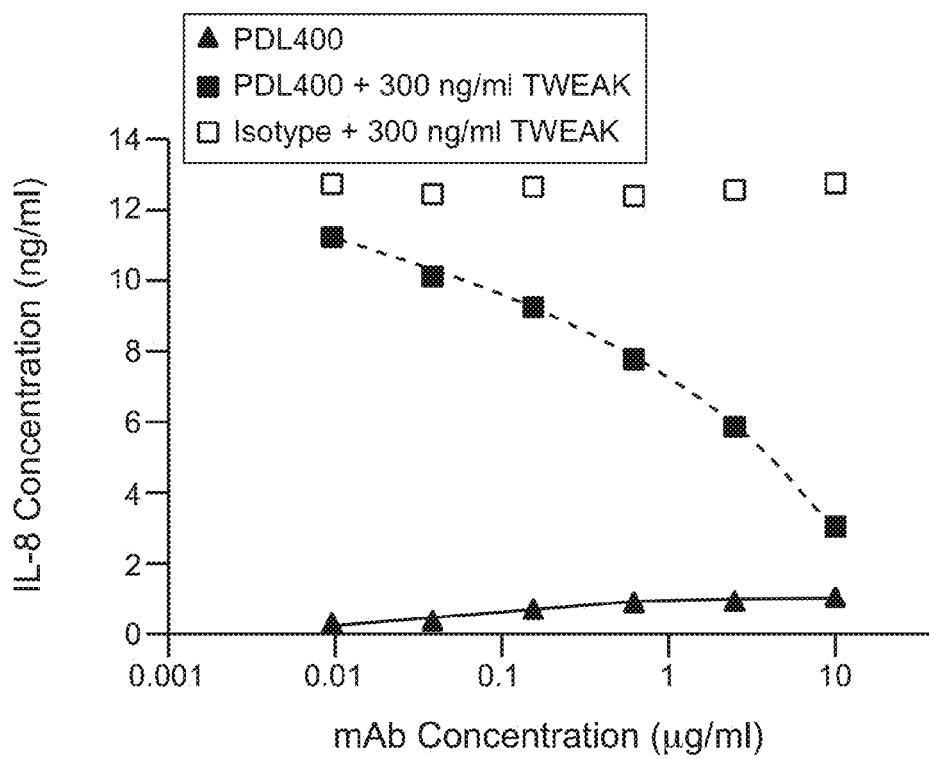
FIG. 8E depicts the release of IL-8 by the anti-Tweak R antibody PDL400.

FIGS. 8A-8E depict exemplary embodiments of IL-8 release using the anti-TweakR antibodies PDL192 (FIG. 8B), 18.3.3 (FIG. 8C), 136.1 (FIG. 8D), PDL400 (FIG. 8E), as well as the previously identified anti-TweakR antibodies, ITEM1, ITEM2, ITEM3, and ITEM4 (FIG. 8A; Nakayama, et al., 2003, Biochem Biophy Res Comm, 306:819-825). Based on the results of two or more experiments, ITEM1 exhibits approximately 25% agonist activity, ITEM2 exhibits approximately 28% agonist activity, ITEM3 exhibits approximately 37% agonist activity, ITEM4 exhibits approximately 12% agonist activity, PDL192 exhibits approximately 25% agonist activity, 19.2.1 exhibits approximately 39% agonist activity, 18.3.3 exhibits approximately 14% agonist activity, 136.1 exhibits approximately 278% agonist activity, and PDL400 exhibits approximately 8% agonist activity.

In some embodiments, anti-TweakR antibodies induce apoptosis in cells expressing TweakR. Assays for apoptosis may be performed by terminal deoxynucleotidyl transferase-mediated digoxigenin-11-dUTP nick end labeling (TUNEL) assay (Lazebnik et al., Nature: 371, 346 (1994). For example, as illustrated in FIGS. 10A-10B, anti-TweakR antibodies are capable of inhibiting the growth of tumor cells via the induction of apoptosis. In the exemplary examples provided in FIGS. 10A-10B, induction of apoptosis is postulated to occur through caspase activation.

In some embodiments, anti-TweakR antibodies stimulate antibody-dependent cellular cytotoxicity (ADCC) in cells expressing TweakR. Typically, anti-TweakR antibodies bind antigens on the surface of target cells (cells that express TweakR) in the presence of effector cells (such as natural killer cells or macrophages). Fc receptors on effector cells recognize bound antibodies. The cross-linking of Fc receptors signals the effector cells to kill the target cells by cytolysis or apoptosis. Cytolysis can be detected via detection of the release of label or lactate dehydrogenase from the lysed cells. Cytotoxicity can be detected directly by detection kits known in the art, such as Cytotoxicity Detection Kit from Roche Applied Science (Indianapolis, Ind.).

In some embodiments, antibody-associated ADCC activity is monitored and quantified through measurement of lactate dehydrogenase (LDH) release in the supernatant, which is rapidly released upon damage to the plasma membrane. To determine the percentage of cell-mediated cytotoxicity, the average absorbance of a sample is calculated and background controls subtracted using the following equation:

$$\text{Cytotoxicity }(\%) = \frac{LDH release_{sample} - SR_{effector} - SR_{target}}{MR_{target} - SR_{target}} \times 100$$

SR refers to spontaneous release and MR refers to maximum release. See also, the methods disclosed in US Patent Application Pub. No. 2005/0025763; the disclosure of which is incorporated herein in its entirety.

In some embodiments, the anti-Tweak R antibodies induce at least 10%, 20%, 30%, 40%, 50%, 60%, or 80% cytotoxicity of the target cells. The anti-TweakR antibodies described herein can have any one of the defined agonist and/or antagonist activities and any one of the defined cytotoxicities.

In the exemplary examples provided in FIGS. 19A-19C, the anti-TweakR antibody, PDL192 induces ADCC activity in SN12C renal cells, as well as TweakR transfectant cell lines using either human peripheral blood mononuclear cells or mouse splenocytes as effector cells. Induction of ADCC by anti-TweakR antibodies was not observed in cells that did not express TweakR (data not shown).

Biological pathways associated with the death of tumor cells in vivo include apoptosis and cytolysis of cells via ADCC. The contributions of apoptosis and ADCC to the anti-tumor activity of anti-Tweak R antibodies was measured in vivo using two anti-TweakR murine antibodies with differing ADCC activities in vitro (data not shown). Murine anti-TweakR 19.2.1, an IgG2a antibody exhibiting strong ADCC activity in vitro, had significant anti-tumor activity in the SN12C renal xenograft model (FIG. 20A) and in the A375 melanoma xenograft model (FIG. 20B). The murine anti-TweakR antibody 19.2.1×G1, which exhibits weak ADCC activity in vitro, had negligible anti-tumor activity in the SN12C renal xenograft model (FIG. 20A) and anti-tumor activity comparable to 19.2.1 in the A375 melanoma xenograft model (FIG. 20B). Accordingly, the anti-TweakR antibodies described herein are capable of reducing or inhibiting tumor cell growth via the induction of one or more biological pathways associated with the killing of cancer cells in vivo.

Antibodies useful in the compositions and methods described herein include anti-TweakR antibodies that specifically bind to the same epitope or epitopes as PDL192, 18.3.3, or 136.1. The epitope bound by the antibodies described herein can be the same, overlapping, or distinct. For example, the specific binding of PDL192 and 19.2.1 to the human TweakR protein is eliminated by changing a single amino acid at position 56, i.e., R56P, of its amino acid sequence (SEQ ID NO:2; data not shown). When R56 is changed to P56, the anti-TweakR antibodies 18.3.3, ITEM1 and ITEM3 antibodies are still capable of binding the human TweakR sequence (data not shown). In addition, anti-TweakR antibodies 18.3.3, ITEM1, and ITEM3 bind the mouse TweakR protein, which comprises a proline at position 56 of its amino acid sequence. However, the anti-TweakR antibodies PDL192 and 19.2.1 do not bind the mouse TweakR protein (data not shown). These results suggest that PDL192 and 19.2.1 bind an epitope that is distinct from the epitope bound by 18.3.3, ITEM1, and ITEM3.

Other antibodies useful in the compositions and methods described herein include, but are not limited to, anti-TweakR antibodies comprising a variable region, at least one framework region, or at least one CDR amino acid sequence that shares 100% identity with, or which is substantially identical to, those selected from the group of SEQ ID NOs: 3-119. The extent of the variable regions, framework regions and CDRs are well-known to those of ordinary skill in the art (see e.g., Kabat, et al., "Sequences of Proteins of Immunological Interest", 5.sup.th ed., National Institutes of Health, Bethesda, Md. (1991)).

As described herein, anti-TweakR antibodies capable of specifically binding TweakR can comprise various combinations of heavy and/or light chain CDRs and/or framework regions. In some embodiments, the anti-TweakR antibodies comprise a heavy and/or a light chain variable region. In other embodiments, the anti-TweakR antibodies described herein comprise one, two, or all three CDRs of a heavy and/or light chain variable. In other embodiments, the anti-TweakR antibodies described herein comprise one, two, three, or all four framework regions. In other embodiments, the anti-TweakR antibodies comprise CDRs of both the heavy and light chain variable regions. In other embodiments, the anti-TweakR antibodies comprise CDRs and framework regions of both the heavy and light chain variable regions. As is apparent from the foregoing description, anti-TweakR antibodies useful in the compositions and methods described herein can comprise any combination of CDR and framework regions provided that the resulting antibodies are capable of specifically binding TweakR and killing cancer cells. The anti-TweakR antibodies can be monoclonal, chimeric, humanized, or fully human.

In some embodiments, the anti-TweakR antibodies can comprise one or more CDRs of a heavy and/or light chain variable region comprising a consensus sequence selected from the group consisting of SEQ ID NOs: 120-123 and 127-129 and various combinations of one or more framework regions of a heavy and/or light chain variable region comprising a consensus sequence selected from the group consisting of SEQ ID NOs: 123-126 and SEQ ID NOs: 130-133.

For example, an anti-TweakR antibody or an antigen binding fragment thereof, can be selected from the group consisting of: a heavy chain CDR1 encoded by an amino acid sequence comprising the formula XaaYWMXaa (SEQ ID NO 120), wherein Xaa at position 1 is S, N, or K and Xaa at position 5 is S or N; a heavy chain CDR2 encoded by an amino acid sequence comprising the formula EIRLKSDN-YATHYAESXaaKG (SEQ ID NO 121), wherein Xaa at position 17 is A or V; a heavy chain CDR3 encoded by an amino acid sequence comprising the formula XaaXaaADXaaX-aaDY (SEQ ID NO 122), wherein Xaa at position 1 is G, T, or Y, Xaa at position 2 is F or Y, Xaa at position 5 is A, T, or Y, and Xaa position 6 is F or M; a light chain CDR1 encoded by an amino acid sequence comprising the formula XaaASQS-VSTSXaaYSYMXaa (SEQ ID NO 127), wherein Xaa at position is 1 is R or K, Xaa at position 10 is S or T and Xaa at position 15 is H or Q; a light chain CDR2 encoded by an amino acid sequence comprising the formula YAXaaXaaLX-aaS (SEQ ID NO 128), wherein Xaa at position 3 is S or T, Xaa at position 4 is N or K, Xaa at position 6 is E or D; a light chain CDR3 encoded by an amino acid sequence comprising the formula QHSWEXaaPYT (SEQ ID NO 129), wherein Xaa at position 6 is I or L; a heavy chain FR1 encoded by an amino acid sequence comprising the formula EVXaaLX-aaESGGGLVQPGGSXaaXaaLSCXaaASGFXaaFXaa (SEQ ID NO 123), wherein Xaa at position 3 is Q or K, wherein Xaa at position 5 is E, V or G, Xaa at position 18 is L or M, Xaa at position 19 is R or K, Xaa at position 23 is A or V, Xaa at position 28 is T or P, and Xaa at position 30 is S, N or T; a heavy chain FR2 encoded by an amino acid sequence comprising the formula WVRQXaaPXaaKGLEWXaaA (SEQ ID NO 124), wherein Xaa at position 5 is A or S, Xaa at position 7 is E or G, Xaa at position 13 is V or L; a heavy chain FR3 encoded by an amino acid sequence comprising the formula XaaFTISRDXaaXaaXaaXaaXaaXaaY-LQMNXaaLRAEXaaTXaaXaaYYCXaaXaa (SEQ ID NO 125), wherein Xaa at position 1 is R or K, Xaa at position 8 is D or N, Xaa at postion 9 is S or A, Xaa at position 10 is K or R, Xaa at position 11 is N or S, Xaa at position 12 is S, R, or T, Xaa at position 13 is L or V, Xaa at position 19 is S or N, Xaa at position 24 is D or N, Xaa at position 26 is A or G, Xaa at position 27 is I or V, Xaa at position 31 is T, S or A, and Xaa at position 32 is G, P, or R; a heavy chain FR4 encoded by an amino acid sequence comprising the formula WGQGTXaa-aaTVSS (SEQ ID NO 126), wherein Xaa at position 6 is L, S or T and Xaa at position 7 is V or L; a light chain FR1 encoded by an amino acid sequence comprising the formula XaaIX-aaXaaTQSPXaaSLXaaXaaSXaaGXaaRXaaTIXaaC(SEQ ID NO 130), wherein Xaa at position 1 is D or E, Xaa at position is 3 is Q or V, Xaa at position 4 is M or L, Xaa at position 9 is G, S or A, Xaa at position 12 is S, A or T, Xaa at position 13 is A, L, or V, Xaa at position 15 is P, V, or L, Xaa at position 17 is D, E, or Q, Xaa at position 19 is V or A, and Xaa at position 22 is T or S; a light chain FR2 encoded by an amino acid sequence comprising the formula WYQQX-aaPGXaaXaaPKLLIK (SEQ ID NO 131), wherein Xaa at 5 position is R or K, Xaa at position 8 is K or Q, and Xaa at position 9 is A, P or S; a light chain FR3 encoded by an amino acid sequence comprising the formula GXaaPXaaRF-SGSGSGTDFTLXaaIXaaXaaXaaXaaX-aaEDXaaAXaaYYC (SEQ ID NO 132), wherein Xaa at position 2 is V or I, Xaa at position 4 is S, D, or A, Xaa at position 18 is T or N, Xaa at position 20 is S or H, Xaa at position 21 is S, R, or P, Xaa at position 22 is L or V, Xaa at position 23 is Q or E, Xaa at position 24 is P or E, Xaa at position 27 is F, T or A and Xaa at position 29 is T or V; and/or a light chain FR4 encoded by an amino acid sequence comprising formula FGXaaGTXaaXaaEIKR (SEQ ID NO 133), wherein Xaa at position 3 is G or Q, Xaa at position 6 is K or R, and Xaa at position 7 is V or L.

By way of another example, an anti-TweakR antibody can comprise a heavy chain CDR1 encoded by an amino acid sequence comprising the formula XaaYWMXaa (SEQ ID NO 120), wherein Xaa at position 1 is S, N, or K and Xaa at position 5 is S or N, a heavy chain CDR2 encoded by an amino acid sequence comprising the formula EIRLKSDN-YATHYAESXaaKG (SEQ ID NO 121), wherein Xaa at position 17 is A or V; and, a heavy chain CDR3 encoded by an amino acid sequence comprising the formula XaaXaaADX-aaXaaDY (SEQ ID NO 122), wherein Xaa at position 1 is G, T, or Y, Xaa at position 2 is F or Y, Xaa at position 5 is A, T, or Y, and Xaa position 6 is F or M.

By way of another example, an anti-TweakR antibody can comprise a light chain CDR1 encoded by an amino acid sequence comprising the formula XaaASQSVSTSXaaY-SYMXaa (SEQ ID NO 127), wherein Xaa at position is 1 is R or K, Xaa at position 10 is S or T and Xaa at position 15 is H or Q, a light chain CDR2 encoded by an amino acid sequence comprising the formula YAXaaXaaLXaaS (SEQ ID NO 128), wherein Xaa at position 3 is S or T, Xaa at position 4 is N or K, Xaa at position 6 is E or D, and, a light chain CDR3 encoded by an amino acid sequence comprising the formula QHSWEXaaPYT (SEQ ID NO 129), wherein Xaa at position 6 is I or L.

In yet other embodiments an anti-TweakR antibody can comprise a heavy chain CDR1 encoded by an amino acid sequence comprising the formula XaaYWMXaa (SEQ ID NO 120), wherein Xaa at position 1 is S, N, or K and Xaa at position 5 is S or N, a heavy chain CDR2 encoded by an amino acid sequence comprising the formula EIRLKSDN-YATHYAESXaaKG (SEQ ID NO 121), wherein Xaa at position 17 is A or V; a heavy chain CDR3 encoded by an amino acid sequence comprising the formula XaaXaaADXaaX-aaDY (SEQ ID NO 122), wherein Xaa at position 1 is G, T, or Y, Xaa at position 2 is F or Y, Xaa at position 5 is A, T, or Y, and Xaa position 6 is F or M, a light chain CDR1 encoded by an amino acid sequence comprising the formula XaaASQS-VSTSXaaYSYMXaa (SEQ ID NO 127), wherein Xaa at position is 1 is R or K, Xaa at position 10 is S or T and Xaa at position 15 is H or Q, a light chain CDR2 encoded by an amino acid sequence comprising the formula YAXaaXaaLX-aaS (SEQ ID NO 128), wherein Xaa at position 3 is S or T, Xaa at position 4 is N or K, Xaa at position 6 is E or D, and, a light chain CDR3 encoded by an amino acid sequence comprising the formula QHSWEXaaPYT (SEQ ID NO 129), wherein Xaa at position 6 is I or L. In addition to the embodiments described for the heavy and/or light chain CDRs, the anti-TweakR antibodies can comprise other combinations of heavy and/or light chain CDRs, provided that the resulting antibodies are capable of specifically binding TweakR and killing cancer cells.

In other embodiments, an anti-TweakR antibody can comprise a heavy chain CDR1 encoded by an amino acid sequence comprising the formula XaaYWMXaa (SEQ ID NO 120), wherein Xaa at position 1 is S, N, or K and Xaa at position 5 is S or N, a heavy chain CDR2 encoded by an amino acid sequence comprising the formula EIRLKSDN-YATHYAESXaaKG (SEQ ID NO 121), wherein Xaa at position 17 is A or V; a heavy chain CDR3 encoded by an amino acid sequence comprising the formula XaaXaaADXaaXaaDY (SEQ ID NO 122), wherein Xaa at position 1 is G, T, or Y, Xaa at position 2 is F or Y, Xaa at position 5 is A, T, or Y, and Xaa position 6 is F or M, a light chain CDR1 encoded by an amino acid sequence comprising the formula XaaASQS-VSTSXaaYSYMXaa (SEQ ID NO 127), wherein Xaa at position is 1 is R or K, Xaa at position 10 is S or T and Xaa at position 15 is H or Q, a light chain CDR2 encoded by an amino acid sequence comprising the formula YAXaaXaaLXaaS (SEQ ID NO 128), wherein Xaa at position 3 is S or T, Xaa at position 4 is N or K, Xaa at position 6 is E or D, a light chain CDR3 encoded by an amino acid sequence comprising the formula QHSWEXaaPYT (SEQ ID NO 129), wherein Xaa at position 6 is I or L, a heavy chain FR1 encoded by an amino acid sequence comprising the formula EVXaaLXaaESGGGLVQPGGSXaaXaaLSCXaaASGFXaaFXaa (SEQ ID NO 123), wherein Xaa at position 3 is Q or K, wherein Xaa at position 5 is E, V or G, Xaa at position 18 is L or M, Xaa at position 19 is R or K, Xaa at position 23 is A or V, Xaa at position 28 is T or P, and Xaa at position 30 is S, N or T, a heavy chain FR2 encoded by an amino acid sequence comprising the formula WVRQXaaPXaaKGLEWXaaA (SEQ ID NO 124), wherein Xaa at position 5 is A or S, Xaa at position 7 is E or G, Xaa at position 13 is V or L, a heavy chain FR3 encoded by an amino acid sequence comprising the formula XaaFTISRDXaaXaaXaaXaaXaaXaaY-LQMNXaaLRAEXaaTXaaXaaYYCXaaXaa (SEQ ID NO 125), wherein Xaa at position 1 is R or K, Xaa at position 8 is D or N, Xaa at postion 9 is S or A, Xaa at position 10 is K or R, Xaa at position 11 is N or S, Xaa at position 12 is S, R, or T, Xaa at position 13 is L or V, Xaa at position 19 is S or N, Xaa at position 24 is D or N, Xaa at position 26 is A or G, Xaa at position 27 is I or V, Xaa at position 31 is T, S or A, and Xaa at position 32 is G, P, or R, and a heavy chain FR4 encoded by an amino acid sequence comprising the formula WGQGTXaaXaaTVSS (SEQ ID NO 126), wherein Xaa at position 6 is L, S or T and Xaa at position 7 is V or L.

By way of another example, an anti-TweakR antibody can comprise a heavy chain CDR1 encoded by an amino acid sequence comprising the formula XaaYWMXaa (SEQ ID NO 120), wherein Xaa at position 1 is S, N, or K and Xaa at position 5 is S or N, a heavy chain CDR2 encoded by an amino acid sequence comprising the formula EIRLKSDN-YATHYAESXaaKG (SEQ ID NO 121), wherein Xaa at position 17 is A or V; a heavy chain CDR3 encoded by an amino acid sequence comprising the formula XaaXaaADXaaXaaDY (SEQ ID NO 122), wherein Xaa at position 1 is G, T, or Y, Xaa at position 2 is F or Y, Xaa at position 5 is A, T, or Y, and Xaa position 6 is F or M, a light chain CDR1 encoded by an amino acid sequence comprising the formula XaaASQS-VSTSXaaYSYMXaa (SEQ ID NO 127), wherein Xaa at position is 1 is R or K, Xaa at position 10 is S or T and Xaa at position 15 is H or Q, a light chain CDR2 encoded by an amino acid sequence comprising the formula YAXaaXaaLXaaS (SEQ ID NO 128), wherein Xaa at position 3 is S or T, Xaa at position 4 is N or K, Xaa at position 6 is E or D, a light chain CDR3 encoded by an amino acid sequence comprising the formula QHSWEXaaPYT (SEQ ID NO 129), wherein Xaa at position 6 is I or L, a heavy chain FR1 encoded by an amino acid sequence comprising the formula EVXaaLXaaESGGGLVQPGGSXaaXaaLSCXaaASGFXaaFXaa (SEQ ID NO 123), wherein Xaa at position 3 is Q or K, wherein Xaa at position 5 is E, V or G, Xaa at position 18 is L or M, Xaa at position 19 is R or K, Xaa at position 23 is A or V, Xaa at position 28 is T or P, and Xaa at position 30 is S, N or T, a heavy chain FR2 encoded by an amino acid sequence comprising the formula WVRQXaaPXaaKGLEWXaaA (SEQ ID NO 124), wherein Xaa at position 5 is A or S, Xaa at position 7 is E or G, Xaa at position 13 is V or L, a heavy chain FR3 encoded by an amino acid sequence comprising the formula XaaFTISRDXaaXaaXaaXaaXaaXaaY-LQMNXaaLRAEXaaTXaaXaaYYCXaaXaa (SEQ ID NO 125), wherein Xaa at position 1 is R or K, Xaa at position 8 is D or N, Xaa at postion 9 is S or A, Xaa at position 10 is K or R, Xaa at position 11 is N or S, Xaa at position 12 is S, R, or T, Xaa at position 13 is L or V, Xaa at position 19 is S or N, Xaa at position 24 is D or N, Xaa at position 26 is A or G, Xaa at position 27 is I or V, Xaa at position 31 is T, S or A, and Xaa at position 32 is G, P, or R, a heavy chain FR4 encoded by an amino acid sequence comprising the formula WGQGTXaaXaaTVSS (SEQ ID NO 126), wherein Xaa at position 6 is L, S or T and Xaa at position 7 is V or L, a light chain FR1 encoded by an amino acid sequence comprising the formula XaaIXaaXaaTQSPXaaSLXaaXaaSXaaGXaaRXaaTIXaaC (SEQ ID NO 130), wherein Xaa at position 1 is D or E, Xaa at position is 3 is Q or V, Xaa at position 4 is M or L, Xaa at position 9 is G, S or A, Xaa at position 12 is S, A or T, Xaa at position 13 is A, L, or V, Xaa at position 15 is P, V, or L, Xaa at position 17 is D, E, or Q, Xaa at position 19 is V or A, and Xaa at position 22 is T or S, a light chain FR2 encoded by an amino acid sequence comprising the formula WYQQXaaPGXaaXaaPKLLIK (SEQ ID NO 131), wherein Xaa at 5 position is R or K, Xaa at position 8 is K or Q, and Xaa at position 9 is A, P or S, a light chain FR3 encoded by an amino acid sequence comprising the formula GXaaPXaaRF-SGSGSGTDFTLXaaIXaaXaaXaaXaaXaaEDXaaAXaaYYC (SEQ ID NO 132), wherein Xaa at position 2 is V or I, Xaa at position 4 is S, D, or A, Xaa at position 18 is T or N, Xaa at position 20 is S or H, Xaa at position 21 is S, R, or P, Xaa at position 22 is L or V, Xaa at position 23 is Q or E, Xaa at position 24 is P or E, Xaa at position 27 is F, T or A and Xaa at position 29 is T or V, and a light chain FR4 encoded by an amino acid sequence comprising formula FGXaaGTXaaXaaEIKR (SEQ ID NO 133), wherein Xaa at position 3 is G or Q, Xaa at position 6 is K or R, and Xaa at position 7 is V or L.

In addition to comprising various combinations of consensus sequences for the heavy and/or light chain CDRs and framework regions described above, the anti-TweakR antibodies described herein can comprise various combinations of heavy and/or light chain CDRs and framework regions selected from the group consisting of SEQ ID NOs: 13, 19, 25, 66, 72, 78, 31, 40, 49, 58, 84, 93, 102 and 111.

By way of example and not limitation, an anti-TweakR antibody can comprise a heavy chain CDR1 encoded by the amino acid sequence comprising SYWMS (SEQ ID NO: 13), a heavy chain CDR2 encoded by the amino acid sequence comprising EIRLKSDNYATHYAESVKG (SEQ ID NO: 19), and a heavy chain CDR3 encoded by the amino acid sequence comprising the formula YYADAMDY (SEQ ID NO: 25).

By way of another example, an anti-TweakR antibody can comprise a light chain CDR1 encoded by the amino acid sequence comprising RASQSVSTSSYSYMH (SEQ ID NO 66), a light chain CDR2 encoded by the amino acid sequence comprising YASNLES (SEQ ID NO 72), and a light chain CDR3 encoded by the amino acid sequence comprising the formula QHSWEIPYT (SEQ ID NO 78).

In other embodiments, an anti-TweakR antibody can comprise all three CDRs from both the heavy and light chain, e.g., a heavy chain CDR1 encoded by the amino acid sequence comprising SYWMS (SEQ ID NO: 13), a heavy chain CDR2 encoded by the amino acid sequence comprising EIRLKSDNYATHYAESVKG (SEQ ID NO: 19), a heavy chain CDR3 encoded by the amino acid sequence comprising the formula YYADAMDY (SEQ ID NO: 25), a light chain CDR1 encoded by the amino acid sequence comprising RASQSVSTSSYSYMH (SEQ ID NO 66), a light chain CDR2 encoded by the amino acid sequence comprising YASNLES (SEQ ID NO 72), and a light chain CDR3 encoded by the amino acid sequence comprising the formula QHSWEIPYT (SEQ ID NO 78). In addition to the embodiments described for the heavy and/or light chain CDRs, the anti-TweakR antibodies can comprise other combinations of heavy and/or light chain CDRs, provided that the resulting antibodies are capable of binding TweakR and killing cancer cells.

By way of another example, an anti-TweakR antibody can comprise a heavy chain FR1 encoded by the amino acid sequence comprising EVQLVESGGGLVQPGGSLRLSCAASGFTFS (SEQ ID NO 31), a heavy chain FR2 encoded by the amino acid sequence comprising WVRQAPGKGLEWVA (SEQ ID NO 40), a heavy chain FR3 encoded by the amino acid sequence comprising RFTISRDDSKNSLYLQMNSLRAEDTAVYYCTG (SEQ ID NO 49), and a heavy chain FR4 encoded by the amino acid sequence comprising WGQGTLVTVSS (SEQ ID NO 58). As will be appreciated by those skilled in the art, in addition to the heavy chain framework regions encoded by SEQ ID NOs; 31, 40, 49, and 58, the anti-TweakR antibodies described herein can comprise one or more heavy chain CDR sequences, e.g., SEQ ID NOs: 13, 19 and 25 and/or one more light chain CDR sequences, e.g., SEQ ID NOs: 66, 72, and 78. In addition to the embodiments described for the heavy and/or light chain CDRs, provided that the resulting antibodies are capable of binding TweakR and killing cancer cells.

By way of another example, an anti-TweakR antibody can comprise a light chain FR1 encoded by the amino acid sequence comprising DIQMTQSPSSLSASVGDRVTITC (SEQ ID NO 84), a light chain FR2 encoded by the amino acid sequence comprising WYQQKPGKAPKLLIK (SEQ ID NO 93), a light chain FR3 encoded by the amino acid sequence comprising GVPSRFSGSGSGTDFTLTISSLQPEDFATYYC (SEQ ID NO 102), and a light chain FR4 encoded by the amino acid sequence comprising FGGGTKVEIKR (SEQ ID NO 111). As will be appreciated by those skilled in the art, in addition to the light chain framework regions encoded by SEQ ID NOs; 84, 93, 102, and 111, the anti-TweakR antibodies described herein can comprise one or more heavy chain CDR sequences, e.g., SEQ ID NOs: 13, 19 and 25 and/or one more light chain CDR sequences, e.g., SEQ ID NOs: 66, 72, and 78, and/or one or more heavy chain framework regions encoded by SEQ ID NOs; 31, 40, 49 and 58. Thus, the anti-TweakR antibodies can comprise other combinations of heavy and/or light chain CDRs and framework regions, provided that the resulting antibodies are capable of binding TweakR and killing cancer cells.

A "substantially identical" variable, constant, framework region, or CDR refers to an antibody region wherein at least about 85-90%, and preferably at least 95% of the amino acid sequence is identical to a natural or unaltered antibody variable or constant region. The terms "identical" or percent "identity," in the context of two or more amino acid or nucleotide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., description of BLAST at the National Center for Biotechnology Information (NCBI) web site).

Identical or substantially identical sequences include sequences having deletions and/or additions, as well as those that have substitutions, as well as naturally occurring, e.g., polymorphic or allelic variants, and man-made variants such as conservatively modified variants. The well-known algorithms for measuring sequence identity can account for gaps and the like. Preferably, sequence identity exists over a region that is at least about 25 amino acids or nucleotides in length, or more preferably over a region that is 50-100 amino acids or nucleotides in length.

The amino acid sequences of the anti-TweakR antibodies useful in the methods described herein are not confined to the sequences found in natural antibodies; antibodies can be redesigned to obtain desired characteristics using well-known recombinant DNA techniques. Such "genetically altered antibodies" include those where the amino acid sequence has been varied from that of a parent (i.e., unaltered) antibody. The possible variations range from the changing of just one or a few amino acids to the complete redesign of, for example, the variable or constant region. Changes, by site-directed mutation, in the constant region may be made in order to improve or alter the functional characteristics of a therapeutic antibody such as immunogenicity, pharmacokinetic characteristics (e.g., serum half-life), complement fixation, interaction with membranes and other effector functions. Generally, changes to the antibody variable region may be made in order to improve the antigen binding characteristics.

Nucleic acids that encode the anti-TweakR antibodies and amino acid sequences described herein, as well as molecules which hybridize to said nucleic acid sequences and which encode anti-TweakR antibodies, such antibodies having the functional properties described herein can be used in the methods disclosed herein.

The anti-TweakR antibodies can be of any of the recognized isotypes. In some embodiments, anti-TweakR antibodies are one of the four human IgG isotypes, i.e., IgG1, IgG2, IgG3 and IgG4, or one of the four mouse IgG isotypes, i.e., murine IgG1, murine IgG2a, murine IgG2b, or murine IgG3. In other embodiments, the anti-TweakR antibodies are of the human IgG1 isotype.

In another embodiment, the antibodies have low levels or lack fucose. Antibodies lacking fucose have been correlated with enhanced ADCC (antibody-dependent cellular cytotoxicity) activity, especially at low doses of antibody. Shields, R. L., et al., (2002) J. Biol. Chem. 277:26733-26740; Shinkawa, T. et al., (2003), J. Biol. Chem. 278:3466. Methods of preparing fucose-less antibodies include growth in rat myeloma YB2/0 cells (ATCC CRL 1662). YB2/0 cells express low levels of FUT8 mRNA, which encodes an enzyme (α 1,6-fucosyltransferase) necessary for fucosylation of polypeptides.

Alternative methods for increasing ADCC activity include mutations in the Fc portion of an anti-TweakR antibody, particularly mutations which increase antibody affinity for an FcγR receptor. A correlation between increased FcγR binding with mutated Fc has been demonstrated using targeted cytoxicity cell-based assays. Shields, R. L. et al. (2001) J. Biol. Chem 276:6591-6604; Presta et al. (2002), Biochem Soc. Trans. 30:487-490. Other methods for increasing ADCC activity include the generation of specific Fc region mutations as described in US Patent Appl. Pub. No. 2005/0025763; the disclosure of which is incorporated herein in its entirety.

Other types of antibodies that can be used in the compositions and methods described herein include, but are not limited to, any immunoglobulin molecule that binds (preferably, immunospecifically, i.e., competes off non-specific binding, as determined by immunoassays well known in the art for assaying specific antigen-antibody binding) an antigen. Such antibodies include, but are not limited to, polyclonal, monoclonal, bi-specific, multi-specific, human, humanized, chimeric antibodies, single chain antibodies, Fab fragments, $F(ab')_2$ fragments, disulfide-linked Fvs, and fragments containing either a $V_L$ or $V_H$ domain or even a complementary determining region (CDR) that specifically binds an antigen, in certain cases, engineered to contain or fused to an Fc binding domain.

6.5 DETECTION OF TweakR SEQUENCES FOR DIAGNOSTIC APPLICATIONS

Expression levels of genes in normal tissue (e.g., not undergoing a disorder) and in diseased tissue (and in some cases, for varying severities of disorders that relate to prognosis, as outlined below) are evaluated to provide expression profiles. A gene expression profile of a particular cell state or point of development is essentially a "fingerprint" of the state of the cell. While two states may have a particular gene similarly expressed, the evaluation of a number of genes simultaneously allows the generation of a gene expression profile that is reflective of the state of the cell. By comparing expression profiles of cells in different states, information regarding which genes are important (including both up- and down-regulation of genes) in each of these states is obtained. Then, diagnosis may be performed or confirmed to determine whether a tissue sample has the gene expression profile of normal or diseased tissue. This will provide for molecular diagnosis of related conditions.

"Differential expression," or grammatical equivalents as used herein, refers to qualitative or quantitative differences in the temporal and/or cellular gene expression patterns within and among cells and tissue. Thus, a differentially expressed gene can qualitatively have its expression altered, including an activation or inactivation, in, e.g., normal versus diseased tissue. Genes may be turned on or turned off in a particular state, relative to another state thus permitting comparison of two or more states. A qualitatively regulated gene will exhibit an expression pattern within a state or cell type which is detectable by standard techniques. Some genes will be expressed in one state or cell type, but not in both. Alternatively, the difference in expression may be quantitative, e.g., in that expression is increased or decreased; e.g., gene expression is either upregulated, resulting in an increased amount of transcript, or downregulated, resulting in a decreased amount of transcript. The degree to which expression differs need only be large enough to quantify via standard characterization techniques as outlined below, such as by use of Affymetrix GENECHIP® (DNA microchip array) expression arrays. See, Lockhart (1996) Nature Biotechnology 14:1675-1680. Other techniques include, but are not limited to, quantitative reverse transcriptase PCR, northern analysis, and RNase protection. As outlined above, preferably the change in expression (e.g., upregulation or downregulation) is at least about 50%, more preferably at least about 100%, more preferably at least about 150%, more preferably at least about 200%, with from 300 to at least 1000% being especially preferred.

Evaluation may be at the gene transcript or the protein level. The amount of gene expression may be monitored using nucleic acid probes to the RNA or DNA equivalent of the gene transcript, and the quantification of gene expression levels, or, alternatively, the final gene product itself (protein) can be monitored, e.g., with antibodies to TweakR protein and standard immunoassays (ELISAs, etc.) or other techniques, including mass spectroscopy assays, 2D gel electrophoresis assays, etc. Proteins corresponding to TweakR, e.g., those identified as being important in a disease phenotype, can be evaluated in a disease diagnostic test. In another embodiment, gene expression monitoring is performed simultaneously on a number of genes. Multiple protein expression monitoring can be performed as well.

Accordingly, in some embodiments, TweakR nucleic acid probes are attached to biochips for the detection and quantification of TweakR sequences in a particular cell. The assays are further described below in the example. PCR techniques can be used to provide greater sensitivity.

In other embodiments, nucleic acids encoding TweakR are detected. Although DNA or RNA encoding TweakR protein may be detected, of particular interest are methods wherein an mRNA encoding a TweakR protein is detected. Probes to detect mRNA can be a nucleotide/deoxynucleotide probe that is complementary to and hybridizes with the mRNA and includes, but is not limited to, oligonucleotides, cDNA, or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method, detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a myelomaprotein is detected by binding the digoxygenin with an anti-digoxygenin secondary antibody and developed with nitro blue tetrazolium and 5-bromo-4-chloro-3-indoyl phosphate.

In other embodiments, TweakR proteins, antibodies, nucleic acids, modified proteins, and cells containing TweakR sequences are used in diagnostic assays. These assays can be performed on an individual gene or corresponding polypeptide level. In one embodiment, the expression profiles are used, preferably in conjunction with high throughput screening techniques to allow monitoring for expression profile genes and/or corresponding polypeptides.

As described and defined herein, TweakR protein finds use as a disease marker of cancerous conditions, including, but are not limited to, bladder cancer, breast cancer, colorectal cancer, lung cancer, melanoma, pancreatic cancer, head and neck cancer, ovarian cancer, stomach cancer, uterine cancer, cervical cancer, esophageal cancer, renal cell carcinoma, glioblastoma, and sarcomas. Additionally, TweakR finds use as a marker for prognostic or diagnostic purposes. Detection of these proteins in putative diseased tissue and/or circulating tumor cells allows for detection, prognosis, or diagnosis of such conditions, and for selection of therapeutic strategy. In one embodiment, antibodies are used to detect TweakR. A preferred method separates proteins from a sample by electrophoresis on a gel (typically a denaturing and reducing protein gel, but may be another type of gel, including isoelectric focusing gels and the like). Following separation of proteins, TweakR is detected, e.g., by immunoblotting with antibodies raised against TweakR.

In another method, antibodies to TweakR find use in in situ imaging techniques, e.g., in histology. See, e.g., Asai, et al. (eds. 1993) Methods in Cell Biology: Antibodies in Cell Biology (vol. 37) Academic Press. In this method, cells are contacted with from one to many antibodies to TweakR protein(s). Following washing to remove non-specific antibody binding, the presence of the antibody or antibodies is detected. In one embodiment the antibody is detected by incubating with a secondary antibody that contains a detectable label. In another method the primary antibody to TweakR contains a detectable label, e.g., an enzyme marker that can act on a substrate. In another embodiment each one of multiple primary antibodies contains a distinct and detectable label. This method finds particular use in simultaneous screening for TweakR along with other markers of the aforementioned conditions. Many other histological imaging techniques are also provided by the invention.

In one embodiment the label is detected in a fluorometer which has the ability to detect and distinguish emissions of different wavelengths. In addition, a fluorescence activated cell sorter (FACS) can be used in the method.

In another embodiment, antibodies find use in diagnosing cancer from blood, serum, plasma, stool, and other samples. Antibodies can be used to detect TweakR by previously described immunoassay techniques including ELISA, immunoblotting (Western blotting), immunoprecipitation, BIA-CORE technology and the like.

In another embodiment, in situ hybridization of labeled TweakR nucleic acid probes to tissue arrays is done. For example, arrays of tissue samples, including diseased tissue and/or normal tissue, are made. In situ hybridization (see, e.g., Ausubel, supra) is then performed. When comparing the fingerprints between an individual and a standard, a diagnosis, a prognosis, or a prediction may be based on the findings. It is further understood that the genes which indicate the diagnosis may differ from those which indicate the prognosis and molecular profiling of the condition of the cells may lead to distinctions between responsive or refractory conditions or may be predictive of outcomes.

In one embodiment, TweakR proteins, antibodies, nucleic acids, modified proteins, and cells containing TweakR sequences are used in prognosis assays. As above, gene expression profiles can be generated that correlate to a disease state, clinical, pathological, or other information, in terms of long term prognosis. Again, this may be done on either a protein or gene level, with the use of genes being preferred. Single or multiple genes may be useful in various combinations. As above, TweakR probes may be attached to biochips for the detection and quantification of TweakR sequences in a tissue or patient. The assays proceed as outlined above for diagnosis. PCR method may provide more sensitive and accurate quantification.

6.6 TREATMENT OF CANCER

The antibodies described herein can be used for the prevention or treatment of abnormal cell proliferation. As used herein, abnormal cell proliferation can be manifested as tumors or as metastases. The term "tumor," as used herein, refers to all neoplastic cell growth and proliferation, whether malignant or benign, and all pre-cancerous and cancerous cells and tissues. The term "metastasis" is used herein in the broadest sense and refers to the spread of tumor, e.g. cancer from one part of the body to another. Tumors formed from cells that have spread are called secondary tumors, and contain the same type of cells as the original (primary) tumor. Thus prostate cancer that has metastasized to liver or bone is not liver or bone cancer, rather metastasized prostate cancer, as it still contains prostate cancer cells, regardless of their location.

Accordingly, in some embodiments, administration of anti-TweakR antibodies can trigger killing of cancer cells. The cancer cells can be present within a solid tumor, the lymph system, or in the bloodstream. As used herein "cancer" includes all malignant neoplasms, including, but not limited to, carcinoma, lymphoma, blastoma, sarcoma, and leukemia. Examples of cancers that may be targeted using the methods disclosed herein include, but are not limited to, bladder cancer, breast cancer, colon cancer, lung cancer, melanoma, pancreatic cancer, ovarian cancer, renal cancer, head and neck cancer, esophageal cancer, uterine cancer, stomach cancer, cervical cancer, glioblastoma, and sarcomas. The therapeutic methods described herein are usually applied to human patients, but can be applied to other mammals.

In some embodiments, administration of anti-TweakR antibodies induces apoptosis or cytolysis of cells expressing TweakR. In some embodiments, induction of cytolysis is achieved via antibody-dependent cellular cytotoxicity (ADCC). For example, the anti-Tweak R antibodies can induce between 10% to greater than 80% cytotoxicity of cells expressing TweakR. In some embodiments, administration of the anti-TweakR antibodies induces at least 10%, 20%, 30%, 40%, 50%, 60%, or 80% or more cytotoxicity of cells expressing TweakR.

In some embodiments, administration of the anti-TweakR antibodies can reduce the size of a solid tumor by targeting TweakR on the cancer cell's surface with one or more of the antibodies described herein. The tumor can be a primary tumor or a secondary tumor. By way of example, administration of the anti-TweakR antibodies can reduce the size of a solid tumor by at least 10%, 20%, 30%, 40%, 50%, 60%, or 80% or more. In other embodiments, administration of the anti-TweakR antibodies can completely inhibit or prevent the growth of a solid tumor.

It will be appreciated that a range of different cytotoxicities and a range of reductions in tumor size are described for the anti-TweakR antibodies disclosed herein. The skilled person will appreciate that the anti-TweakR antibodies can have any one of the described cytotoxicities and any one of the described reductions in tumor size.

In some embodiments, the methods can employ an anti-TweakR antibody conjugated to an effector moiety. The effector moiety may be any number of molecules, including labeling moieties such as radioactive labels or fluorescent labels, or preferably may be a therapeutic moiety. The effector moiety (or "effector component") may be bound (or linked, or conjugated), to the anti-TweakR antibody either covalently, through a linker or a chemical bond, or noncovalently, through ionic, van der Waals, electrostatic, or hydrogen bonds.

The therapeutic moiety can be a small molecule that modulates the activity TweakR. In another aspect, the therapeutic moiety affects the activity of molecules or cells associated with or in close proximity to TweakR. For example, the therapeutic moiety may be a cytotoxic agent. The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof. Suitable toxins and their corresponding fragments include diphtheria A chain, exotoxin A chain, ricin A chain, abrin A chain, curcin, crotin, phenomycin, enomycin, auristatins (e.g., auristatin E, or auristatin F), and the like. Targeting the therapeutic moiety to the TweakR expressed on the surface of a cancer cell not only serves to increase the local concentration of therapeutic moiety in the afflicted area, but also serves to reduce deleterious side effects that may be associated with the therapeutic moiety.

In other embodiments, the anti-TweakR antibodies can be used in combination with conventional therapeutic agents used to treat a particular cancer. The conventional standard of care for a particular cancer is known to those skilled in the art and thus, one of skill in the art will be able to select one or more therapeutic agents to combine with the anti-TweakR antibodies described herein. By way of example, pancreatic cancer is currently treated using the therapeutic agent gemcitabine with or without erlotinib (Tarceva®). Thus, the anti-TweakR antibodies can be used in combination with gemcitabine and/or erlotinib to treat pancreatic cancer.

Examples of other therapeutic agents that are presently used to treat cancer, and thus can be used in combination with the anti-TweakR antibodies described herein, include, but are not limited to, targeted agents, conventional chemotherapy agents, and hormonal therapy agents.

In some embodiments, the anti-TweakR antibodies described herein can be used in combination with targeted agents. Targeted agents include, but are not limited to, anti-angiogenic agents (such as bevacizumab, sunitinib, sorafenib, temsirolimus, 2-methoxyestradiol or 2ME2, finasunate, PTK787, and vandetanib), EGFR inhibitors (such as erlotinib, cetuximab, panitumumab, gefinitib, lapatinib, and trastuzumab), immunomodulators (such as rituximab, alemtuzumab, and aldesleukine), proteasome inhibitors (such as bortezomib, PR-171, and NPI-052), integrin inhibitors (such as natalizumab, volociximab, etaracizumab, and cilengitide), pro-apoptotic agents (such as mapatumumab, lexatumumab, AMG951, ABT-737, oblimersen, and plitidepsin), and agents with other mechanisms of action (such as imatinib, dasatinib, lenalidomide, thalidomide, aldesleukin, and interferon alpha).

In some embodiments, the anti-TweakR antibodies described herein can be used in combination with conventional chemotherapy agents. Conventional chemotherapy agents include, but are not limited to, alkylating agents (such as oxaliplatin, carboplatin, cisplatin, cyclophosphamide, melphalan, ifosfamide, uramustine, chlorambucil, mechloethamine, thiotepa, busulfan, temozolomide, and dacarbazine), anti-metabolites (gemcitabine, cytosine arabinoside, Ara-C, capecitabine, 5FU (5-fluorouracil), azathioprine, mercaptopurine (6-MP), 6-thioguanine, aminopterin, pemetrexed, and methotrexate), plant alkaloids and terpenoids (such as docetaxel, paclitaxel, protein-bound paclitaxel, vincristine, vinblastin, vinorelbine, vindesine, etoposide, VP-16, teniposide, irinotecan, and topotecan), and anti-tumor antibiotics (such as dactinomycin, doxorubicin, liposomal doxorubicin, daunorubicin, daunomycin, epirubicin, mitoxantrone, adriamycin, bleomycin, plicamycin, mitomycin C, carminomycin, and esperamicins).

In some embodiments, the anti-TweakR antibodies described herein can be used in combination with hormonal therapy agents (such as anastrozole, letrozole, goserelin, and tamoxifen).

Accordingly, the anti-TweakR antibodies described herein can be used as a monotherapy or in combination with other therapeutic agents. In some embodiments, the anti-TweakR antibodies described herein are useful as monotherapeutic agents or as part of a combination therapy regime for the treatment of cancer patients that have become resistant to anti-EGFR antibodies. Resistance to anti-EGFR antibodies has been hypothesized to be associated with mutations that result in constitutive activation of EGFR-mediated signaling (see, e.g., Jhawer, et al., 2008, Cancer Res., 68(6):1953-1961). Several recent studies have shown a link between K-Ras mutation status and cetuximab response, with tumors wild type for K-Ras showing improved response to this agent (Lievre, et al., 2008, J. Clin. Oncology, 26(3):374-379). Colon cancer cell lines with activating PIK3CA mutations or loss of PTEN expression were found to be more resistant to cetuximab than PIK3CA wild type/PTEN expressing cell lines (Jhawer, et al., 2008, Cancer Res., 68(6):1953-1961). Mutations activating the RAS/RAF signaling pathway have been shown to be predictive and prognostic indicators in colorectal cancer patients (Benvenuti, et al., 2007, Cancer Res., 67(6):2643-2648).

Many of the xenograft models used to test the efficacy of anti-TweakR antibodies carry BRAF, KRAS, PTEN, and PIK3CA mutations, including NW231 (breast adenocarcinoma), HT29 (colorectal adenocarcinoma), A375 (melanoma), Calu6 (lung anaplastic carcinoma), A549 (lung carcinoma), 786-0 (renal clear cell carcinoma), and HCT116 (colorectal adenocarcinoma). In some of these models, i.e., NW231, HT29, and A375, the anti-TweakR antibody PDL192 was effective at reducing and/or inhibiting the growth of the tumor (see Table 2), suggesting that anti-TweakR antibodies can be used to treat cancer patients that do not respond to, or have become resistant to, EGFR inhibitors, such as anti-EGFR antibodies.

In the HT29 xenograft model, PDL192 was shown to enhance the anti-tumor activity of cetuximab/irinotecan combination in HT29 (data not shown). These results provide a rationale for combining anti-TweakR antibodies with agents that target different pathways as part of a treatment regime for patients who do not respond to, or become resistant to, EGFR inhibitors, such as anti-EGFR antibodies.

Thus, in some embodiments, anti-TweakR antibodies are administered to cancer patients that do not respond to, or become resistant to treatment with anti-epidermal growth factor receptor (EGFR) antibodies such as cetuximab and panitumumab. The anti-TweakR antibodies can be administered alone or in combination with other therapeutic agents, including, but not limited to, targeted agents, conventional chemotherapy agents and hormonal therapy agents.

In some embodiments, cancer patients that are resistant to or do not respond to anti-EGFR antibodies are screened for BRAF, KRAS, PTEN, and PIK3CA mutations as described in Benvenuti, et al. 2007, Cancer Res., 67(6):2643-2648. Patients that have mutations in one or more of these genes are identified and treated with anti-TweakR antibodies alone or in combination with other therapeutic agents, including, but not limited to, targeted agents, conventional chemotherapy agents and hormonal therapy agents.

One or more of the above therapeutic agents, can be administered concurrently, prior to, or following administration of an anti-TweakR antibody. The agents can be administered separately or combined in a cocktail and administered together as a single composition. The composition(s) can be administered by any means known in the art.

Other useful treatments that can be used in combination with the anti-TweakR antibodies, include radiation therapy.

The anti-TweakR antibodies can be formulated into a pharmaceutical composition that is administered to a subject in a therapeutically effective amount. As used herein, "therapeutically effective amount" refers to the amount of a pharmaceutical formulation or composition that is sufficient to cure, alleviate, attenuate or at least partially arrest the cancer and/or its symptoms, and/or complications. Clinical methods for determining the therapeutically effective amount of an anti-TweakR antibody for treatment of cancer are well-known to those of ordinary skill in the art and may be determined empirically using routine experimentation. For example, in the context of cancer treatment, a "therapeutically effective amount" is an amount capable of invoking one or more of the following effects: (1) inhibition, to some extent, of tumor growth, including, slowing down and complete growth arrest; (2) reduction in the number of cancer cells; (3) reduction in tumor size; (4) inhibition (i.e., reduction, slowing down or complete stopping) of cancer cell infiltration into peripheral organs; (5) inhibition (i.e., reduction, slowing down or complete stopping) of cancer cell metastasis; (6) enhancement of anti-cancer immune response, which may, but does not have to, result in the regression or rejection of a tumor; and/or (7) relief, to some extent, of one or more symptoms associated with the disorder.

The concentration of an antibody in these formulations varies widely from about 0.1 to 100 mg/ml, but is often in the range 1 to 20 mg/ml. For the purpose of treatment of disease, the appropriate dosage of the antibody will depend on the severity and course of disease, the patient's clinical history and response, the toxicity of the antibodies, and the discretion of the attending physician. The antibodies are suitably administered to the patient at one time or over a series of treatments. The proper dosage and treatment regimen can be established by monitoring the progress of therapy using conventional techniques known to the people skilled of the art.

Typically, the compositions described herein are administered to a patient intravenously as a bolus or by continuous infusion over a period of time; or by intramuscular, subcutaneous, intraperitoneal, or intra-cerebrospinal routes. Methods for preparing parentally administrable compositions are known or apparent to those skilled in the art and are described in more detail in, for example, Remington's Pharmaceutical Science (15th Ed., Mack Publishing Company, Easton, Pa., 1980), which is incorporated herein by reference.

As disclosed herein, compositions formulated for pharmaceutical use comprise one or more of the anti-TweakR antibodies described herein. The compositions optionally further comprise a carrier. The pharmaceutical compositions described herein typically comprise an anti-TweakR antibody and a pharmaceutical carrier, and, commonly they comprise a solution of an anti-TweakR antibody, or a cocktail thereof, dissolved in an acceptable carrier, preferably an aqueous carrier. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc. to make isotonic. The carrier can also contain excipients such as human serum albumin, polysorbate 80, sugars or amino acids to protect the active protein.

For use in diagnostic and research applications suggested above, kits are also provided herein. In diagnostic and research applications, such kits may include at least one of the following: assay reagents, buffers, TweakR-specific nucleic acids or antibodies, hybridization probes and/or primers, antisense polynucleotides, ribozymes, dominant negative TweakR polypeptides or polynucleotides, and/or small molecule inhibitors of TweakR-associated sequences.

In addition, the kits may include instructional materials containing instructions (e.g., protocols) for the practice of the methods of this invention. While the instructional materials typically comprise written or printed materials, they are not limited to such. A medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

Thus, the anti-TweakR antibodies and antigen binding fragments disclosed herein, and the compositions and kits comprising these antibodies and antigen binding fragments, can be used for therapy, and in particular for treatment of any of the diseases described herein.

7. EXAMPLES

Example 1

TweakR Expression in Primary Tumors

Gene expression profiling was used to detect the expression of TweakR mRNA in a variety of primary solid tumors, including lung, pancreatic, renal, breast and head and neck cancers. mRNA was isolated from various cancers and 347 normal adult tissues and was hybridized to Eos Hu03, a customized Affymetrix gene chip containing approximately 59,000 probesets representing 46,000 genes, EST clusters, and predicted exons.

Significant TweakR expression was detected in 31 of 44 lung adenocarcinomas, 27 of 56 lung squamous cell carcinomas, 37 of 47 pancreatic tumors, 14 of 23 tumors of head and neck origin, 48 of 66 ovarian cancers, 190 of 253 primary and metastatic colorectal cancers, 11 of 11 esophageal cancers, 16 of 35 melanomas, 15 of 20 renal cancers, 29 of 39 stomach cancers, 25 of 43 uterine cancers, 7 of 14 cervical cancers, 8 of 26 sarcomas, 23 of 93 bladder cancers, and 16 of 27 glioblastomas (data not shown). In breast cancers, 24 of 47 primary tumor samples from 45 patients showed significant TweakR expression, and 7 of 10 metastatic tumors to the spinal column expressed TweakR (data not shown).

Figure 6:
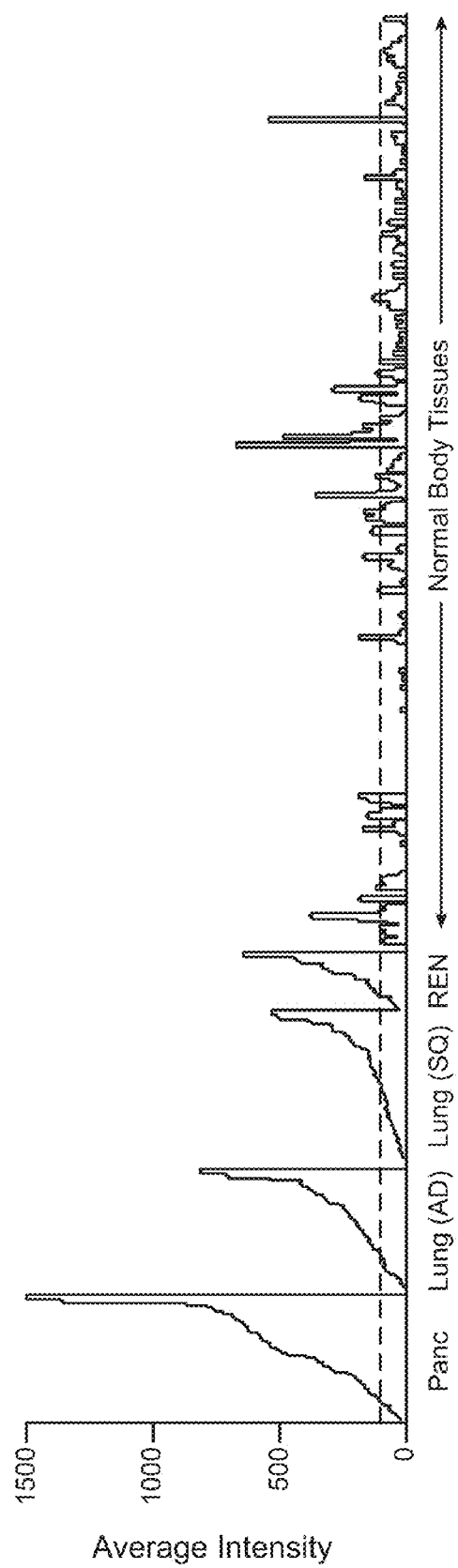

In FIG. 6, cDNA array expression levels of TweakR in pancreatic, lung (adenocarcinoma and squamous cell carcinoma), and renal cancers are compared to a range of normal body tissues. The samples are displayed along on the X-axis, with the height of each sample reflecting the average intensity or expression level of TweakR. Samples with expression levels above the horizontal dashed line at 100 are considered positive for TweakR expression.

Immunohistochemical staining using anti-TweakR antibodies was also used to examine TweakR expression in solid tumors from lung adenocarcinoma, lung squamous cell carcinoma, and pancreatic cancer. Cryopreserved tumor specimens were incubated with the anti-TweakR antibody, 29.T10 (5 µg/ml). A horseradish peroxidase-conjugated secondary antibody was added, followed by color development with diaminobenzidine (DAB).

The immunohistochemical staining was in agreement with the gene chip results. Using antibodies to TweakR (29.T10, 374.2, and 349.2), TweakR protein was detected on lung adenocarcinomas, lung squamous cell carcinomas, pancreatic adenocarcinomas, renal cell carcinomas, breast ductal carcinomas, colorectal adenocarcinomas, ovarian carcinomas, stomach adenocarcinomas, bladder cancers, and cancers of head and neck origin cancers. FIG. 7A-7D is a typical example of TweakR protein staining using antibody 29.T10 on solid tumors.

Example 2

Generation and Characterization of Anti-TweakR Antibodies

Generation of Anti-TweakR Antibodies
Monoclonal Antibodies
Monoclonal antibodies were generated by immunizing Balb/c mice intraperitoneally with mouse 3T12 cells overexpressing human TweakR. Spleens were harvested, and splenocytes were fused with the multiple myeloma cell line, NS0. Hybridomas were selected using aminopterin. Hybridomas expressing anti-TweakR antibodies of interest were subcloned several times to isolate individual clones.

Humanization of 19.2.1 to Create PDL192
Humanization of 19.2.1 was carried out essentially according to the procedure of Queen, C. et al. (Proc. Natl. Acad. Sci. USA 86: 10029-10033 (1989)). First, human VH and VL segments with high homology to the 19.2.1 VH and VL amino acid sequences, respectively, were identified. Next, the CDR sequences together with framework amino acids important for maintaining the structures of the CDRs were grafted into the selected human framework sequences. The resulting humanized monoclonal antibody (PDL192) was expressed in the mouse myeloma cell line NS0.

Cloning and Sequencing of 19.2.1 Variable Region cDNAs
Total RNA was extracted from approximately $5\times10^7$ hybridoma cells producing 19.2.1 using TRIzol reagent (Life Technologies, Inc., Rockville, Md.). Double-stranded cDNA was synthesized using the SMART RACE cDNA Amplification Kit (BD Biosciences Clontech, Palo Alto, Calif.) following the supplier's protocol. The variable region cDNAs for the heavy and light chains were amplified by polymerase chain reaction (PCR) using 3' primers that anneal respectively to the mouse gamma and kappa chain C regions, and a 5' universal primer provided in the SMART RACE cDNA Amplification Kit. The VH and VL cDNAs were subcloned into the pCR4Blunt-TOPO vector (Invitrogen Corporation, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instructions. Multiple plasmid clones were sequenced for each of the heavy and light chains variable regions.

Design of PDL192 V Regions
Humanization of the antibody V regions was carried out as outlined by Queen, C. et al. (Proc. Natl. Acad. Sci. USA 86: 10029-10033 (1989)). First, a molecular model of the 19.2.1 variable regions was constructed with the aid of the computer programs ABMOD and ENCAD (Levitt, M., J. Mol. Biol. 168: 595-620 (1983)). Next, based on a homology search against human antibody cDNA sequences, appropriate human VH, VL, and J segment sequences were selected to provide the frameworks for the PDL192 variable regions.

At framework positions in which the computer model suggested significant contact with the CDRs, the amino acids from the 19.2.1 V regions were substituted for the original human framework amino acids. This was done at residues 73, 74, 93, and 94 of the heavy chain. For the light chain, replacement was made at residue 49. Note that the numbering system used here is that of Kabat (Sequences of Proteins of Immunological Interest, 5th ed., National Institutes of Health, Bethesda, Md. (1991)).

Construction of PDL192 VH and VL Genes
DNA segments encoding each of PDL192 VH and VL were designed as a mini-exons including a signal peptide, a splice donor signal, and appropriate restriction enzyme sites for subsequent cloning into a mammalian expression vector. The 19.2.1 VH and VL mini-exons were constructed by extension of overlapping synthetic oligonucleotides ranging in length from 33 to 43 bases and PCR amplification (Stemmer et al, Gene 164:49-53 (1995)). The PCR-amplified fragments were purified by Qiaquick PCR purification kit (Qiagen), digested with appropriate restriction enzymes, cloned into a vector for expression containing human IgG1 and kappa constant domains, and expressed in mouse NS0 cells.

Humanization of PDL400 from ITEM4 was similar to the process described above for PDL192, except that different framework substitutions were selected based on the computer model.

Binding Affinities
The relative binding affinities of various mouse and humanized anti-TweakR antibodies were assessed in a Biacore assay using a soluble form of the extracellular domain of human TweakR. Briefly, goat anti-mouse Fc antibody or goat anti-human Fc was first immobilized to the biosensor surface followed by capture of antibody on the test surface. Subsequently, the soluble form of the extracellular domain of human TweakR was injected to measure binding to, and dissociation from, antibody. The relative binding affinities of various mouse antibodies, including 19.2.1, 136.1, and 18.3.3, and various humanized antibodies, including PDL192 and PDL400 are shown in Table 1.

TABLE 1

| Anti-TweakR Antibodies | Binding Affinity ($K_D$) |
|---|---|
| PDL192 | 5.5 nM |
| 19.2.1 | 7.12 nM |
| 136.1 | 0.68 nM |
| 18.3.3 | 0.23 nM |
| PDL400 | 0.58 nM |

As shown in Table 1, the affinity of PDL192 was similar to that of the murine parental antibody, 19.2.1. Thus, the humanization process did not significantly alter the antibody binding affinity.

Agonist/Antagonistic Activities
TWEAK, the ligand for TweakR, activates multiple signaling pathways, resulting in pleiotropic effects on cells, including increasing the expression of cytokines and chemokines, stimulation of angiogenesis, and induction of apoptosis in cancer cells. The anti-TweakR antibodies were assessed for their abilities to exert biological activities attributed to TWEAK using several in vitro assays designed to measure the effects of the anti-TweakR antibodies on cell growth, stimulation of angiogenesis and expression of cytokines and chemokines.

In the cell growth assays, human umbilical vein endothelial cells (HUVEC), coronary artery smooth muscle cells, lung fibroblasts, or hepatocytes were incubated for 3 days in the presence of 100 ng/ml TWEAK or 10 ng/ml isotype control antibody or the anti-TweakR antibody, 19.2.1. Cell viability was assessed using alamar blue. Compared to isotype-treated cells, HUVEC growth was stimulated by TWEAK or 19.2.1 (data not shown). On these cells, TWEAK enhanced growth by 2.4-fold, while 19.2.1 stimulated a 1.6-fold increase in growth. Neither TWEAK nor 19.2.1 had any effect on growth of coronary artery smooth muscle cells, aortic smooth muscle cells, lung fibroblasts, or hepatocytes.

Anti-TweakR antibodies were assessed for their abilities to promote the formation of endothelial tubes in vitro. HUVEC cells were incubated in a fibrin matrix in the presence of 200 ng/ml TWEAK, 10 μg/ml isotype control antibody or 10 μg/ml 19.2.1. After 6 days, the length of the tubes generated was quantified. Both TWEAK and 19.2.1 stimulated endothelial tube formation, with TWEAK showing an approximately 3.5-fold increase in total tube length, and 19.2.1 stimulating a 2.5-fold increase (data not shown).

The ability of anti-TweakR antibodies to stimulate cytokine and chemokine expression was tested on a number of cancer cell lines and also normal primary human cells, including endothelial cells, hepatocytes, lung fibroblasts, and coronary artery smooth muscle cells. Cells were incubated in vitro for 24 hours with TWEAK at 100 ng/ml or with an anti-TweakR antibody at 10 μg/ml. Twenty four hours later, the cell supernatant was assessed for the presence of up to 15 different cytokines and chemokines using a commercial fluorescent bead-based multiplex (Luminex®; Upstate) assay.

Each cell type released a unique set of cytokines/chemokines in response to TWEAK. Some of the anti-TweakR antibodies, such as 19.2.1 and PDL192 induced secretion of the same subset of cytokines/chemokines (e.g., IL-8, IL-6, GM-CSF, MCP-1, RANTES, and IP-10) as TWEAK, but at lower concentrations. TWEAK, 19.2.1, and PDL192 did not stimulate the release of IFNγ, TNFα, TNFβ, IL-2, IL-4, IL-5, IL-10, IL-12, or IL-13 from any cell type examined (data not shown).

Based on the above results, release of IL-8 from A375 melanoma cells by anti-TweakR antibodies was used as the assay of choice to characterize the agonist/antagonistic activity of the various antibodies, as well as previously identified anti-TweakR antibodies, including ITEM1, ITEM2, ITEM3, and ITEM 4 (Nakayama, et al., 2003, Biochem Biophysical Res Comm., 306:819-825). FIG. 8 depicts the release of IL-8 by ITEM1, ITEM2, ITEM3, and ITEM 4 (all used at 10 μg/ml), as well as various isotype controls. As illustrated in FIG. 8, all of the ITEM antibodies have agonist activity, in that they induce some IL-8 expression when incubated with A375 cells. In addition, all of the ITEM antibodies have some antagonist activity, in that when A375 cells are incubated with TWEAK ligand (300 ng/ml) plus the antibodies, the amount of IL-8 released is less than that observed with TWEAK treatment alone. Agents with pure antagonist activity, a soluble form of TweakR extracellular domain (TweakR-Fc) and a neutralizing anti-TWEAK antibody, are shown for comparison.

Representative IL-8 release assays for the anti-TweakR antibodies PDL192, 18.3.3, 136.1 and PDL 400 are shown in FIGS. 8B, 8C, 8D, and 8E, respectively. As shown in FIGS. 8B-8E, the agonist/antagonist activities differ between the antibodies described herein. For example, PDL192 (FIG. 8B) and 19.2.1 (data not shown) have virtually no antagonistic activity, i.e., they do not block IL-8 release induced by TWEAK. PDL 400 (FIG. 8E) and 18.3.3 (FIG. 8C) have agonist and antagonist activities. The anti-TweakR antibody 136.1 (FIG. 8D) has very high agonist activity, which precludes assessment of its antagonist activity in this assay.

In Vitro Anti-Tumor Activity

Figure 9:
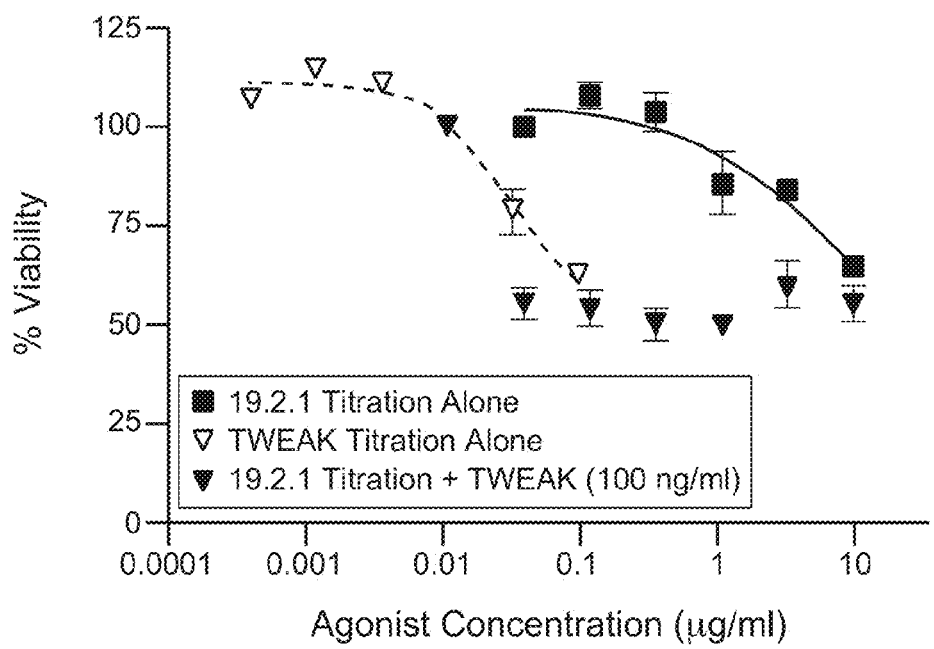
FIG. 9 depicts a typical anti-proliferative assay using the anti-TweakR antibody, 19.2.1.

Two assays were employed to assess the anti-proliferative effects of anti-TweakR antibodies in vitro, an anchorage-dependent assay (a proliferation assay), and an anchorage-independent assay (a colony formation assay). A typical anti-proliferative assay using 19.2.1 on A375 melanoma cells is shown in FIG. 9. Overall, PDL192 and 19.2.1 decreased the proliferation of 15 of 40 TweakR-expressing cancer cell lines and reduced the colony formation potential of 9 of 33 TweakR-expressing cancer cell lines (data not shown)

The anti-TweakR antibodies, PDL192, 19.2.1, and 136.1 were tested for the ability to decrease or inhibit the growth of the cancer cells by inducing apoptosis through caspase activation. IFNγ-treated HT29 colon cancers cells were incubated with titrations of the three antibodies. Within 1-2 days of antibody treatment, the cells were assessed for activation of caspase 3/7. As shown in FIGS. 10A-10B, PDL192 and 136.1 were capable of inducing apoptosis through caspase activation in HT29. 19.2.1 had a similar effect (data not shown). In other cancer cell lines, apoptosis does not appear to be the mechanism by which the anti-TweakR antibodies inhibits proliferation; in these cell lines, the antibodies are postulated to mediate activity through an alternate mechanism(s) that causes a reduction in proliferation in a longer-term 7-10 day growth assay (data not shown).

Example 3

In Vivo Tumor Activity of Anti-TweakR Antibodies

Treatment with anti-TweakR antibodies in vivo was performed on xenograft models generated from a number of cancer cell lines. As shown in Table 2, anti-TweakR antibodies were effective in reducing and/or inhibiting the growth of a number of different cancers.

TABLE 2

Summary of anti-tumor activity in xenograft models

| Tumor Tissue Type | Xenograft Model | Percent Inhibition by[1] | | | |
|---|---|---|---|---|---|
| | | 19.2.1 | PDL192 | 18.3.3 | PDL400 |
| Renal cell carcinoma | SN12C | 98% | 95% | nt[2] | 95% |
| | 786-0 | nt | NS[3] | nt | nt |
| Breast adenocarcinoma | MDA-MB-231 variant | 42% | 81% | nt | nt |
| | MDA-MB-453 | nt | NS | nt | nt |
| Colorectal adenocarcinoma | HT29 | nt | 78% | nt | nt |
| | Lovo | nt | NS | nt | nt |
| | VACO9P | nt | NS | nt | nt |
| | HCT116 | NS | nt | nt | nt |
| Melanoma | A375 | 65% | 69% | 69% | nt |
| | LOX | nt | 60% | nt | nt |
| Ovarian carcinoma | CSOC882-2 | nt | 89% | nt | nt |
| | ES2 | nt | 75% | nt | nt |
| | SK-OV-3 | nt | NS | nt | nt |

TABLE 2-continued

Summary of anti-tumor activity in xenograft models

| Tumor Tissue Type | Xenograft Model | Percent Inhibition by[1] | | | |
|---|---|---|---|---|---|
| | | 19.2.1 | PDL192 | 18.3.3 | PDL400 |
| Pancreatic adenocarcinoma | Panc1 | nt | 79% | nt | nt |
| | BxPC3 | NS | nt | nt | nt |
| Salivary gland carcinoma | A253 | 86% | 73% | 54% | 70% |
| Urinary bladder carcinoma | HT1376 | 36% | 48% | nt | 56% |
| Glioblastoma | U118 | nt | 40% | nt | nt |
| Lung carcinoma | H358 | nt | 58% | nt | nt |
| | Calu6 | 21% | 26% | nt | 29% |
| | A549 | 30% | 25% | nt | nt |
| | EKVX | NS | nt | nt | nt |

[1]Percent inhibition was calculated by comparing the average tumor volume of control animals with treated animals using measurements taken the day of sacrifice of the control animal group (when the majority of tumors were at the allowable limit).
[2]nt: not tested.
[3]NS: no significant difference between anti-TweakR antibody and isotype control treated groups.

Severe-combined immunodeficient (SCID) mice were inoculated subcutaneously with SN12C renal cancer cells. When the tumors reached approximately 100 mm$^3$, the animals were dosed intraperitoneally with PDL192, PDL400, or 19.2.1, or an isotype control antibody at 10 mg/kg, 3 times per week for 3 weeks. A dose-range finding study was also used to determine the range of efficacious dose levels with PDL192 in the SN12C model. In this model, animals were dosed with PDL192 at 10 mg/kg, 5 mg/kg, 2.5 mg/kg, 1 mg/kg, 0.3 mg/kg, or 0.1 mg/kg, or isotype control antibody at 10 mg/kg, 3 times per week for 3 weeks.

PDL192 causes tumor regression in the SN12C renal cancer xenograft model. Similar results were observed with PDL400 and 19.2.1 (data not shown). In the dose-range finding study, shown in FIG. 11, tumor regression is observed with PDL192 at doses as low as 1 mg/kg. At a lower dose of 0.3 mg/kg, regression is not achieved, but PDL192 significant anti-tumor activity is observed.

Severe-combined immunodeficient (SCID) mice were inoculated subcutaneously with A253 salivary gland cancer cells. When the tumors reached approximately 100 mm$^3$, the animals were dosed intraperitoneally with 19.2.1, PDL192, 18.3.3, and PDL400, or isotype control antibody at 10 mg/kg, 3 times per week for 3 weeks. Dose-range finding studies in the A253 model of head and neck cancer were also used with 19.2.1 to determine the minimum concentration of circulating antibody that shows biological activity (minimum effective serum concentration). Severe-combined immunodeficient (SCID) mice were inoculated subcutaneously with A253 salivary gland cancer cells. When the tumors reached approximately 100 mm$^3$, the animals were dosed intraperitoneally with 19.2.1 at 10 mg/kg, 5 mg/kg, 2.5 mg/kg, 1 mg/kg, or 0.5 mg/kg, or isotype control antibody at 10 mg/kg, 3 times per week for 3 weeks.

As shown in FIG. 12, at the 10 mg/kg dose level, significant anti-tumor activity is observed with 19.2.1 in the A253 model of head and neck cancer. Similar results were obtained with PDL192, 18.3.3, and PDL400 (data not shown). In the dose-range finding study depicted in FIG. 12, the maximal anti-tumor activity with 19.2.1 in the A253 model of head and neck cancer is achieved at 5 mg/kg, and minimal activity is observed at 0.5 mg/kg. In a separate study, the serum concentrations of 19.2.1 were assessed at these same dose levels. The 5 mg/kg dose level, where maximal anti-tumor activity was observed, correlated with circulating antibody concentrations of 20-120 ng/ml. Minimal biological activity, observed at the 0.5 mg/kg dose level, correlated with an antibody concentration of 1-7 μg/ml (data not shown). This dose range characterizes the potential therapeutic window for anti-TweakR antibodies.

Severe-combined immunodeficient (SCID) mice were inoculated subcutaneously with A253 salivary gland carcinoma cells. When the tumors reached approximately 100 mm$^3$, the animals were dosed intraperitoneally with 19.2.1 at 5 mg/kg or isotype control antibody at 10 mg/kg, 3 times per week for 3 weeks (9 doses) or for 7 weeks (22 doses) (19.2.1 only).

In the A253 xenograft model of head and neck cancer, 19.2.1 significantly inhibited tumor growth. The efficacy of 19.2.1 was assessed in mice receiving 9 doses at 5 mg/kg over 3 weeks or 22 doses at 5 mg/kg over the course of 7 weeks (FIG. 13). For both dosing groups, tumor growth was significantly inhibited during the dosing period and for approximately 3 weeks after dosing was completed (FIG. 13). This result suggests that anti-tumor activity is maintained until the circulating antibody concentration falls below the minimal level required for efficacy.

Severe-combined immunodeficient (SCID) mice were inoculated subcutaneously with HT1376 urinary bladder carcinoma cells. When the tumors reached approximately 100 mm$^3$, the animals were dosed intraperitoneally with PDL192, 19.2.1, and PDL400, or isotype control antibody at 10 mg/kg, 3 times per week for 7 doses.

In the HT1376 urinary bladder xenograft model, tumor growth was moderately inhibited. FIG. 14 depicts the reduction in tumor growth following treatment with PDL192. Similar results were obtained using 19.2.1 and PDL400 (date not shown).

Severe-combined immunodeficient (SCID) mice were inoculated subcutaneously with A375 melanoma cells. When the tumors reached approximately 100 mm$^3$, the animals were dosed intraperitoneally with PDL192, 19.2.1, and 18.3.3, or isotype control antibody at 10 mg/kg, 3 times per week for 3 weeks. A dose-range finding study was also used to determine the range of efficacious dose levels with PDL192 in the A375 model. In this study, animals were dosed with PDL192 at 10 mg/kg, 5 mg/kg, 2.5 mg/kg, 1 mg/kg, 0.3 mg/kg, or 0.1 mg/kg, or isotype control antibody at 10 mg/kg, 3 times per week (3 qw) for 3 weeks.

In the 3 qw A375 melanoma xenograft model, tumor growth was significantly inhibited using PDL192 at 10 mg/kg (FIG. 15). Similar results were obtained using 19.2.1 and 18.3.3 (data not shown). FIG. 15 depicts the reduction in tumor growth following treatment with PDL192 in the dose-range finding study, with significant anti-tumor activity observed at all dose levels, even as low as 0.1 mg/kg.

A separate dose-range finding study was conducted in the A375 xenograft model to correlate the minimal and optimal biological activities of PDL192 with circulating antibody concentrations. Severe-combined immunodeficient (SCID) mice were inoculated subcutaneously with A375 melanoma cells. When the tumors reached approximately 100 mm$^3$, the animals were dosed intraperitoneally with PDL192 at 5 mg/kg, 1 mg/kg, 0.6 mg/kg, 0.3 mg/kg, or 0.1 mg/kg, or isotype control antibody at 5 mg/kg, every three days (q3 d) for a total of 8 doses Animals were bled at various times throughout the study to measure PDL192 concentrations in the serum.

In the q3 d A375 dose-range finding study, PDL192 exhibited optimal anti-tumor activity at the 1 mg/kg and 5 mg/kg dose levels (data not shown), where trough serum concentrations of PDL192 were 2.4 and 62 ng/ml and peak serum concentrations were 5.9 and 86 ng/ml. Minimal-to-moderate anti-tumor activity was observed at the 0.1, 0.3, and 0.6 mg/kg dose levels (data not shown), where trough serum concentrations of PDL192 were 0.97 ng/ml, 4.1 ng/ml, and 27 ng/ml, respectively, and peak serum concentrations were 0.087, 1.4, and 3 ng/ml, respectively. This dose range characterizes the potential therapeutic window for anti-TweakR antibodies.

Severe-combined immunodeficient (SCID) mice were inoculated subcutaneously with CSOC ovarian cancer carcinoma cells. When the tumors reached approximately 100 mm$^3$, the animals were dosed intraperitoneally with PDL192 or isotype control antibody at 10 mg/kg, 3 times per week for 3 weeks.

In the CSOC ovarian cancer xenograft model, tumor growth was strongly inhibited by PDL192. FIG. 16 depicts the reduction in tumor growth following treatment with PDL192.

Severe-combined immunodeficient (SCID) mice were inoculated subcutaneously with Panc1 pancreatic cancer cells. When the tumors reached approximately 100 mm$^3$, the animals were dosed intraperitoneally with PDL192 at 10 mg/kg, or with isotype control antibody at 10 mg/kg, or with PDL192 at 10 mg/kg and gemcitabine at 60 mg/kg, or with isotype control antibody at 10 mg/kg and gemcitabine at 60 mg/kg. Animals received doses of antibody 3 times per week for 3 weeks and/or gemcitabine 2 times per week for 5 doses.

In the Panc1 xenograft model, tumor growth was significantly inhibited by PDL192. The combination of PDL192 and gemcitabine resulted in 100% tumor regression. FIG. 17 depicts the reduction in tumor growth following treatment with PDL192± gemcitabine.

Severe-combined immunodeficient (SCID) mice were inoculated subcutaneously with HT29 colorectal cancer cells. When the tumors reached approximately 100 mm$^3$, the animals were dosed intraperitoneally with PDL192 at 10 mg/kg or 0.5 mg/kg, with isotype control antibody at 10 mg/kg, with cetuximab at 10 mg/kg, with irinotecan at 25 mg/kg and isotype control antibody at 10 mg/kg, with irinotecan at 25 mg/kg and cetuximab at 10 mg/kg, with irinotecan at 25 mg/kg and PDL192 at 0.5 mg/kg, with PDL192 at 0.5 mg/kg and cetuximab at 10 mg/kg, or with PDL192 at 0.5 mg/kg and cetuximab at 10 mg/kg and irinotecan at 25 mg/kg. Animals received doses of antibody 3 times per week for 3 weeks and/or irinotecan 2 times per week for 3 weeks.

In the HT29 xenograft model, tumor growth was strongly inhibited by PDL192 at a dose level of 10 mg/kg (data not shown). At a lower dose of 0.5 mg/kg, PDL192 did not inhibit tumor growth alone, but did significantly enhance the anti-tumor activity of irinotecan (data not shown).

HT29 colorectal cancer cells are mutant for B-raf. In contrast to the potent anti-tumor activity of PDL192 at 10 mg/kg in the HT29 xenograft model, cetuximab at 10 mg/kg showed no inhibition of tumor growth. However, combining cetuximab at 10 mg/kg with a low dose of PDL192 at 0.5 mg/kg, resulted in statistically significant tumor growth inhibition (data not shown).

In the HT29 xenograft model, treatment of the combination of cetuximab and irinotecan resulted in significant tumor growth inhibition. At a low dose of 0.5 mg/kg, while PDL192 alone did not inhibit tumor growth, it enhanced the anti-tumor activity of the cetuximab/irinotecan combination (data not shown).

Severe-combined immunodeficient (SCID) mice were inoculated orthotopically in the mammary fat pad with a variant of the MDA-MB-231 breast cancer cell line. When the tumors reached approximately 100 mm$^3$, the animals were dosed intraperitoneally with PDL192 or 19.2.1, or isotype control antibody at 10 mg/kg, 3 times per week for 3 weeks. A dose-range finding study was also used to determine the range of efficacious dose levels with PDL192 in this model. In this study, animals were dosed with PDL192 at 10 mg/kg, 3 mg/kg, 1 mg/kg, or 0.3 mg/kg, or isotype control antibody at 10 mg/kg, 3 times per week for 3 weeks.

In the MDA-MB-231 variant model, PDL192 significantly inhibited primary tumor growth. FIG. 18A depicts the reduction in primary tumor size following treatment with PDL192. Similar results were obtained using 19.2.1 (data not shown). The MDA-MB-231 variant model exhibits metastatic growth in the lungs of tumor-bearing mice. Quantification of the lung metastases revealed that PDL192 significantly reduced the establishment and growth of lung metastases in treated mice. FIG. 18B depicts the inhibition of lung metastases. Metastatic growth was more sensitive to PDL192 treatment than was the growth of primary tumors.

Example 4

In Vitro ADCC Activity

The in vivo anti-tumor activities of the anti-TweakR antibodies is likely due, in part, to the ability of the antibodies to stimulate antibody-dependent cellular cytotoxicity (ADCC) through the Fc portion of the antibody molecule. To determine if ADCC was involved in the anti-tumor activities of the anti-TweakR antibodies, including PDL192, 19.2.1, PDL400, 136.1 and 18.3.3, the antibodies were incubated in vitro with: 1) TweakR transfectant cells in the presence of healthy human peripheral blood mononuclear cells (PBMCs), 2) cancer cell lines in the presence of PBMCs, 3) TweakR transfectant cells in the presence of mouse splenocytes, or 4) cancer cell lines in the presence of mouse splenocytes.

A TweakR transfectant cell line was labeled with $^{51}$Cr and incubated with human PBMCs at a 50:1 ratio of effector cells:target cells in the presence of a titration of PDL192, 19.2.1, PDL400, and 18.3.3, or isotype-control antibodies. ADCC activity was observed with all four antibodies on the TweakR transfectant with human PBMCs. FIG. 19A depicts a typical experiment using PDL192. Similar results were obtained with the other three antibodies (data not shown).

The SN12C renal cancer cell line was labeled with $^{51}$Cr and incubated with human PBMCs at a 50:1 ratio of effector cells:target cells in the presence of a titration of PDL192 and PDL400, or isotype-control antibodies. ADCC activity was observed with both antibodies against SN12C cells with human PBMCs. FIG. 19B depicts a typical experiment using PDL192. Similar results were obtained with PDL400 (data not shown).

A TweakR transfectant cell line was labeled with $^{51}$Cr and incubated with mouse splenocytes at a 50:1 ratio of effector cells:target cells in the presence of a titration of PDL192, 19.2.1, PDL400, 136.1 and 18.3.3, or isotype-control antibodies. ADCC activity was observed with all five antibodies on the TweakR transfectant with mouse splenocytes. FIG. 19C depicts a typical experiment using PDL192. Similar results were obtained with the other four antibodies (data not shown).

Example 5

Anti-Tumor Activity In Vivo Through Multiple Mechanisms Action

The Fc region of 19.2.1 was changed from a murine IgG2a to murine IgG1, generating 19.2.1×G1. In in vitro assays, 19.2.1 and 19.2.1×G1 exhibited similar binding to TweakR-expressing cells, and both antibodies killed HT29 colon cancer cells in a dose-dependent manner. However, while 19.2.1 potently induced ADCC on a TweakR transfectant, 19.2.1× G1 exhibited weak ADCC activity.

Severe-combined immunodeficient (SCID) mice were inoculated subcutaneously with SN12C renal cancer cells or A375 melanoma cells. When the tumors reached approximately 100 mm$^3$, the animals were dosed intraperitoneally with 19.2.1, 19.2.1×G1, or a murine IgG1 isotype control antibody at 10 mg/kg, 3 times per week for 3 weeks.

In the SN12C renal cancer xenograft model, 19.2.1 treatment resulted in complete tumor regression. In contrast, 19.2.1×G1 exhibited minimal anti-tumor activity (FIG. 19A). In the A375 xenograft model of melanoma, both isotypes of 19.2.1 exhibited equally potent anti-tumor activity (FIG. 20B).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A monoclonal anti-TweakR antibody or an antigen binding fragment thereof, comprising the following six CDRs:
$V_H$ CDR #1 is: S Y W M S (SEQ ID NO:13);
$V_H$ CDR #2 is: E I R L K S D N Y A T H Y A E S V K G (SEQ ID NO:19);
$V_H$ CDR #3 is: Y Y A D A M D Y (SEQ ID NO:25);
$V_L$ CDR #1 is: A A S Q S V S T S S Y S Y M H (SEQ ID NO:66);
$V_L$ CDR #2 is: Y A S N L E S (SEQ ID NO:72); and
$V_L$ CDR #3 is: Q H S W E I P Y T (SEQ ID NO:78).

2. The monoclonal anti-TweakR antibody or antigen binding fragment of claim 1, which comprises a $V_H$ region comprising SEQ ID NO:3 and a $V_L$ region comprising SEQ ID NO:4.

3. The monoclonal anti-TweakR antibody or antigen binding fragment of claim 2, which is an $IgG_1$.

4. The monoclonal anti-TweakR antibody or antigen binding fragment of claim 1, which comprises a $V_H$ region comprising SEQ ID NO:5 and a $V_L$ region comprising SEQ ID NO:6.

5. The monoclonal anti-TweakR antibody or antigen binding fragment of claim 1 which is conjugated to an effector moiety and/or a detectable label.

6. The monoclonal anti-TweakR antibody or antigen binding fragment of claim 5 which is conjugated to a detectable label.

7. The monoclonal anti-TweakR antibody or antigen binding fragment of claim 6, wherein the detectable label is a radioactive compound, a fluorescent compound, an enzyme, a substrate or an epitope tag.

8. The monoclonal anti-TweakR antibody or antigen binding fragment of claim 5, which is conjugated to an effector moiety.

9. The monoclonal anti-TweakR antibody or antigen binding fragment of claim 8, wherein the effector moiety is a cytotoxic agent.

10. The monoclonal anti-TweakR antibody or antigen binding fragment of claim 9, wherein the cytotoxic agent is a toxin, a chemotherapeutic agent, an immune modulator, or a radioisotope.

11. The monoclonal anti-TweakR antibody or antigen binding fragment of claim 1 which is humanized.

12. A pharmaceutical composition comprising the antibody of claim 1 and a pharmaceutically acceptable carrier or diluent.

13. A method of treating a subject having a solid tumor, comprising administering to the subject a therapeutically effective amount of the pharmaceutical composition of claim 12.

14. The method of claim 13, further comprising administering to the subject a second therapeutic agent selected from the group consisting of a targeted therapeutic agent, a conventional chemotherapy agent, and a hormonal therapy agent.

15. The method of claim 14, wherein the second therapeutic agent is a conventional chemotherapy agent.

16. The method of claim 13, wherein the solid tumor is a bladder cancer, a breast cancer, a colorectal cancer, a lung cancer, a melanoma, a pancreatic cancer, an ovarian cancer, a renal cancer, a head and neck cancer, an esophageal cancer, a uterine cancer, a stomach cancer, a cervical cancer, a glioblastoma, or a sarcoma.

17. The method of claim 16, wherein the solid tumor is a colorectal cancer.

18. The method of claim 16, wherein the solid tumor is a pancreatic cancer.

19. The method of claim 16, wherein the solid tumor is a breast cancer.

20. The method of claim 13, in which the solid tumor has a mutation in a gene selected from the group consisting of BRAF, KRAS, PTEN, and PIK3CA.

21. The method of claim 20, in which the solid tumor has a mutation in PIK3 CA.

* * * * *